US011452847B1

(12) United States Patent
Cook

(10) Patent No.: US 11,452,847 B1
(45) Date of Patent: *Sep. 27, 2022

(54) BLOOD COLLECTION DEVICES, SYSTEMS, AND METHODS

(71) Applicant: AVIA VASCULAR, LLC, Salt Lake City, UT (US)

(72) Inventor: Kevin Jerry Cook, Kaysville, UT (US)

(73) Assignee: Avia Vascular, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/841,956

(22) Filed: Jun. 16, 2022

Related U.S. Application Data

(63) Continuation of application No. 17/676,964, filed on Feb. 22, 2022, now Pat. No. 11,389,624, which is a
(Continued)

(51) Int. Cl.
*A61M 25/06* (2006.01)
*A61B 5/15* (2006.01)

(52) U.S. Cl.
CPC ..... *A61M 25/0606* (2013.01); *A61B 5/15003* (2013.01); *A61B 5/150992* (2013.01)

(58) Field of Classification Search
CPC .......... A61M 25/0606; A61M 25/0113; A61M 2025/0681; A61M 2025/0004;
(Continued)

(56) References Cited

U.S. PATENT DOCUMENTS

| 3,262,448 A | 7/1966 | Ring et al. |
| 3,515,137 A | 6/1970 | Santiomieri |

(Continued)

FOREIGN PATENT DOCUMENTS

| CN | 101884823 A | 11/2010 |
| DE | 3401452 A1 | 8/1985 |

(Continued)

OTHER PUBLICATIONS

International Searching Authority, International Search Report and Written Opinion of the International Searching Authority in Patent Cooperation Treaty International Application No. PCT/US2021/060888, dated Feb. 28, 2022, 17 pages.

(Continued)

*Primary Examiner* — Dung T Ulsh
(74) *Attorney, Agent, or Firm* — Med Venture Management, LLC; Daniel C. Higgs

(57) ABSTRACT

In certain instances, an access system can include a connector to couple with a catheter assembly, a reinforcement member fixedly secured to the connector, and a cannula movable relative to the reinforcement member. The cannula can include a polymeric tube and a support tube that encompasses a portion of and is stiffer than the polymeric tube. The support tube can define an inner diameter that is marginally larger than an outer diameter of the polymeric tube to prevent kinking of the polymeric tube and can be in a fixed relationship with the polymeric tube. A distal edge of the support tube is proximally spaced from a distal tip of the polymeric tube and is within the reinforcement member when the distal tip of the polymeric tube is first positioned distal of and external to the reinforcement member as the cannula is advanced.

20 Claims, 45 Drawing Sheets

Related U.S. Application Data continuation of application No. 17/535,821, filed on Nov. 26, 2021.

(60) Provisional application No. 63/118,679, filed on Nov. 26, 2020, provisional application No. 63/225,992, filed on Jul. 27, 2021, provisional application No. 63/256,625, filed on Oct. 17, 2021.

(58) Field of Classification Search
CPC .......... A61M 39/02; A61M 2039/0202; A61B 5/15003; A61B 5/150992
See application file for complete search history.

(56) References Cited

U.S. PATENT DOCUMENTS

| | | |
|---|---|---|
| 3,565,074 A | 2/1971 | Foti |
| 3,584,624 A | 6/1971 | de Ciutiis |
| 3,633,579 A | 1/1972 | Alley et al. |
| 3,739,778 A | 6/1973 | Monestere, Jr. et al. |
| 3,757,771 A | 9/1973 | Ruegg et al. |
| 3,766,913 A | 10/1973 | Balin |
| 3,782,381 A | 1/1974 | Winnie |
| 3,825,001 A | 7/1974 | Bennet et al. |
| 4,037,600 A | 7/1977 | Poncy et al. |
| 4,068,659 A | 1/1978 | Moorehead |
| 4,068,660 A | 1/1978 | Beck |
| 4,192,319 A | 3/1980 | Hargens et al. |
| 4,205,675 A | 6/1980 | Vaillancourt |
| 4,235,232 A | 11/1980 | Spaven et al. |
| 4,304,231 A | 12/1981 | Bodicky et al. |
| 4,314,555 A | 2/1982 | Sagae |
| 4,326,520 A | 4/1982 | Alley |
| 4,333,455 A | 6/1982 | Bodicky |
| 4,417,886 A | 11/1983 | Frankhouser et al. |
| 4,451,256 A | 5/1984 | Weikl et al. |
| 4,464,171 A | 8/1984 | Garwin |
| 4,464,176 A | 8/1984 | Wijayarathna |
| 4,613,329 A | 9/1986 | Bodicky |
| 4,636,272 A | 1/1987 | Riggs |
| 4,705,511 A | 11/1987 | Kocak |
| 4,767,409 A | 8/1988 | Brooks |
| 4,790,830 A | 12/1988 | Hamacher |
| 4,803,999 A | 2/1989 | Liegner |
| 4,808,158 A | 2/1989 | Kreuzer et al. |
| 4,808,165 A | 2/1989 | Carr |
| 4,935,010 A | 6/1990 | Cox et al. |
| 4,976,697 A | 12/1990 | Walder et al. |
| 5,013,304 A | 5/1991 | Russel et al. |
| 5,047,018 A | 9/1991 | Gay et al. |
| 5,057,092 A | 10/1991 | Webster, Jr. |
| 5,069,674 A | 12/1991 | Fearnot et al. |
| 5,100,390 A | 3/1992 | Lubeck et al. |
| 5,125,902 A | 6/1992 | Berry et al. |
| 5,135,502 A | 8/1992 | Koenig, Jr. et al. |
| 5,147,334 A | 9/1992 | Moss |
| 5,156,594 A | 10/1992 | Keith |
| 5,195,979 A | 3/1993 | Schinkel et al. |
| 5,199,950 A | 4/1993 | Schmitt et al. |
| 5,201,722 A | 4/1993 | Moorehead et al. |
| 5,203,771 A | 4/1993 | Melker et al. |
| 5,240,537 A | 8/1993 | Bodicky |
| 5,254,107 A | 10/1993 | Soltez |
| 5,270,003 A | 12/1993 | Bernes et al. |
| 5,360,407 A | 11/1994 | Leonard |
| 5,368,029 A | 11/1994 | Holcombe et al. |
| 5,387,193 A | 2/1995 | Miraki |
| 5,496,294 A | 3/1996 | Hergenrother et al. |
| 5,507,995 A | 4/1996 | Schweich, Jr. et al. |
| 5,552,118 A | 9/1996 | Mayer |
| 5,553,625 A | 9/1996 | Rao |
| 5,532,631 A | 10/1996 | Bogert |
| 5,601,539 A | 2/1997 | Corso, Jr. |
| 5,611,782 A | 3/1997 | Haedt |
| 5,658,263 A | 8/1997 | Dang et al. |
| 5,658,264 A | 8/1997 | Samson |
| 5,704,914 A | 1/1998 | Stocking et al. |
| 5,713,876 A | 2/1998 | Bogert et al. |
| 5,743,875 A | 4/1998 | Sirhan et al. |
| 5,749,857 A | 5/1998 | Cuppy |
| 5,755,709 A | 5/1998 | Cuppy |
| 5,772,643 A | 6/1998 | Howell et al. |
| 5,800,389 A | 9/1998 | Burney et al. |
| 5,800,410 A | 9/1998 | Gawreluk |
| 5,807,350 A | 9/1998 | Diaz |
| 5,827,229 A | 10/1998 | Auth et al. |
| 5,843,050 A | 12/1998 | Jones et al. |
| 5,848,996 A | 12/1998 | Eldor |
| 5,853,393 A | 12/1998 | Bogert |
| 5,897,537 A | 4/1999 | Berg et al. |
| 5,902,282 A | 5/1999 | Balbierz |
| 5,911,715 A | 6/1999 | Berg et al. |
| 5,944,690 A | 8/1999 | Falwell et al. |
| 5,944,695 A | 8/1999 | Johnson et al. |
| 6,007,519 A | 12/1999 | Rosselli |
| 6,036,677 A | 3/2000 | Javier, Jr. et al. |
| 6,059,759 A | 5/2000 | Mottola et al. |
| 6,063,318 A | 5/2000 | Houser et al. |
| 6,080,138 A | 6/2000 | Lemke et al. |
| 6,093,177 A | 7/2000 | Javier, Jr. et al. |
| 6,126,618 A | 10/2000 | Bischof |
| 6,190,371 B1 | 2/2001 | Maginot et al. |
| 6,197,001 B1 | 3/2001 | Wilson et al. |
| 6,213,978 B1 | 4/2001 | Voyten |
| 6,248,100 B1 | 6/2001 | de Toledo et al. |
| 6,375,774 B1 | 4/2002 | Lunn et al. |
| 6,447,477 B2 | 9/2002 | Burney et al. |
| 6,508,790 B1 | 1/2003 | Lawrence |
| 6,524,299 B1 | 2/2003 | Tran et al. |
| 6,585,703 B1 | 7/2003 | Kassel et al. |
| 6,589,251 B2 | 7/2003 | Yee et al. |
| 6,596,235 B2 | 7/2003 | Divino, Jr. et al. |
| 6,648,835 B1 | 11/2003 | Shemesh |
| 6,652,507 B2 | 11/2003 | Pepin |
| 6,685,664 B2 | 2/2004 | Levin et al. |
| 6,692,473 B2 | 2/2004 | St. Cyr et al. |
| 6,706,018 B2 | 3/2004 | Westlund et al. |
| 6,712,790 B1 | 3/2004 | Pretidge et al. |
| 6,719,726 B2 | 4/2004 | Meng et al. |
| 6,719,781 B1 | 4/2004 | Kim |
| 6,722,370 B1 | 4/2004 | Mann |
| 6,755,812 B2 | 6/2004 | Peterson et al. |
| 6,821,287 B1 | 11/2004 | Jang |
| 6,852,261 B2 | 2/2005 | Benjamin |
| 6,858,024 B1 | 2/2005 | Berg et al. |
| 6,908,459 B2 | 6/2005 | Harding et al. |
| 6,913,595 B2 | 7/2005 | Mastorakis |
| 6,994,700 B2 | 2/2006 | Elkins et al. |
| 7,008,404 B2 | 3/2006 | Nakajima |
| 7,087,047 B2 | 8/2006 | Kraus et al. |
| 7,125,396 B2 | 10/2006 | Leinsing et al. |
| 7,135,008 B2 | 11/2006 | O'Mahony et al. |
| 7,156,836 B2 | 1/2007 | Teo |
| 7,166,088 B2 | 1/2007 | Heuser |
| 7,252,654 B2 | 8/2007 | VanTassel et al. |
| 7,311,689 B2 | 12/2007 | Levin et al. |
| 7,316,678 B2 | 1/2008 | Nash et al. |
| 7,462,161 B2 | 12/2008 | O'Mahony et al. |
| 7,615,033 B2 | 11/2009 | Leong |
| 7,625,367 B2 | 12/2009 | Adams et al. |
| 7,662,110 B2 | 2/2010 | Flaherty |
| 7,670,320 B2 | 3/2010 | Iwase et al. |
| 7,691,088 B2 | 4/2010 | Howell |
| 7,713,250 B2 | 5/2010 | Harding et al. |
| 7,713,256 B2 | 5/2010 | Brimhall et al. |
| 7,713,257 B2 | 5/2010 | Brimhall et al. |
| 7,717,882 B2 | 5/2010 | Harding |
| 7,717,899 B2 | 5/2010 | Bowe et al. |
| 7,749,196 B2 | 7/2010 | Osborne et al. |
| 7,762,977 B2 | 7/2010 | Porter et al. |
| 7,766,971 B2 | 8/2010 | Gladdish, Jr. et al. |
| 7,771,394 B2 | 8/2010 | Shue et al. |
| 7,785,317 B2 | 8/2010 | Mitelberg |
| 7,892,208 B2 | 2/2011 | Schnell et al. |

(56) References Cited

U.S. PATENT DOCUMENTS

| | | |
|---|---|---|
| 7,914,492 B2 | 3/2011 | Heuser |
| 7,972,294 B2 | 7/2011 | Nash et al. |
| 8,029,472 B2 | 10/2011 | Leinsing et al. |
| 8,029,481 B2 | 10/2011 | Reavill |
| 8,048,031 B2 | 11/2011 | Shaw et al. |
| 8,062,226 B2 | 11/2011 | Moore |
| 8,066,670 B2 | 11/2011 | Cluff et al. |
| 8,092,374 B2 | 1/2012 | Smith et al. |
| 8,104,475 B2 | 1/2012 | Cheung |
| 8,105,286 B2 | 1/2012 | Anderson et al. |
| 8,114,057 B2 | 2/2012 | Gerdts et al. |
| 8,192,402 B2 | 6/2012 | Anderson et al. |
| 8,202,251 B2 | 6/2012 | Bierman et al. |
| 8,231,601 B2 | 7/2012 | Reavill |
| 8,251,978 B2 | 8/2012 | Nash et al. |
| 8,267,911 B2 | 9/2012 | Gallogly et al. |
| 8,328,759 B2 | 12/2012 | Donawick |
| 8,361,013 B2 | 1/2013 | Wood, Jr. |
| 8,361,014 B2 | 1/2013 | Wood, Jr. |
| 8,366,685 B2 | 2/2013 | Devgon |
| 8,372,032 B2 | 2/2013 | Wood, Jr. |
| 8,425,532 B2 | 4/2013 | Flom et al. |
| 8,444,605 B2 | 5/2013 | Kuracina et al. |
| 8,460,181 B2 | 6/2013 | Saadat et al. |
| 8,491,568 B2 | 7/2013 | Schertiger et al. |
| 8,523,801 B2 | 9/2013 | Nash et al. |
| 8,585,651 B2 | 11/2013 | Asai |
| 8,696,639 B2 | 4/2014 | Smith et al. |
| 8,702,658 B2 | 4/2014 | Spearman |
| 8,721,546 B2 | 5/2014 | Belson |
| 8,728,035 B2 | 5/2014 | Warring et al. |
| 8,728,058 B2 | 5/2014 | Schertiger |
| 8,740,850 B2 | 6/2014 | Leinsing et al. |
| 8,753,312 B2 | 6/2014 | Bowe et al. |
| 8,808,246 B2 | 8/2014 | Cabot |
| 8,845,547 B2 | 9/2014 | Heske et al. |
| 8,876,773 B2 | 11/2014 | Ishida |
| 8,900,192 B2 | 12/2014 | Anderson et al. |
| 8,932,259 B2 | 1/2015 | Stout et al. |
| 8,936,581 B2 | 1/2015 | Bihlmaier |
| 8,974,411 B2 | 3/2015 | McKinnon |
| 9,028,425 B2 | 5/2015 | Burkholz |
| 9,056,182 B2 | 6/2015 | Moulton et al. |
| 9,084,851 B2 | 7/2015 | Kosinski et al. |
| 9,089,474 B2 | 7/2015 | Cederschiold |
| 9,114,241 B2 | 8/2015 | Stout et al. |
| 9,126,012 B2 | 9/2015 | McKinnon et al. |
| RE45,776 E | 10/2015 | Root et al. |
| 9,149,604 B2 | 10/2015 | Nishide et al. |
| 9,155,876 B2 | 10/2015 | Sonderegger et al. |
| 9,186,100 B2 | 11/2015 | Devgon |
| 9,233,208 B2 | 1/2016 | Tekeste |
| 9,302,049 B2 | 4/2016 | Tekeste |
| 9,314,201 B2 | 4/2016 | Burkholz et al. |
| 9,352,119 B2 | 5/2016 | Burkholz et al. |
| 9,352,128 B2 | 5/2016 | Ishida |
| 9,358,335 B2 | 6/2016 | Wada et al. |
| 9,393,382 B2 | 7/2016 | Heck |
| 9,399,112 B2 | 7/2016 | Shevgoor et al. |
| 9,408,569 B2 | 8/2016 | Andreae et al. |
| 9,415,185 B2 | 8/2016 | Otter |
| 9,474,641 B2 | 11/2016 | Ivancev |
| 9,480,794 B2 | 11/2016 | Keith et al. |
| 9,522,229 B2 | 12/2016 | Sonderegger et al. |
| 9,522,237 B2 | 12/2016 | Alheidt et al. |
| 9,549,701 B2 | 1/2017 | Peterson et al. |
| 9,579,486 B2 | 2/2017 | Burkholz et al. |
| 9,592,374 B2 | 3/2017 | Muse |
| 9,616,214 B2 | 4/2017 | Stout et al. |
| 9,668,654 B2 | 6/2017 | Rajendran et al. |
| 9,706,980 B2 | 7/2017 | Heske et al. |
| 9,707,378 B2 | 7/2017 | Leinsing et al. |
| 9,737,686 B2 | 8/2017 | Trainer et al. |
| 9,744,344 B1 | 8/2017 | Devgon et al. |
| 9,750,446 B2 | 9/2017 | Devgon |
| 9,764,117 B2 | 9/2017 | Bierman et al. |
| 9,770,580 B2 | 9/2017 | Burkholz et al. |
| 9,877,675 B2 | 1/2018 | Baid |
| 9,895,092 B2 | 2/2018 | Burkholz |
| 9,907,913 B2 | 3/2018 | Kosinski et al. |
| 9,909,162 B2 | 3/2018 | Yeh |
| 9,943,676 B2 | 4/2018 | Tekeste |
| 9,980,706 B2 | 5/2018 | Heske et al. |
| 9,980,878 B2 | 5/2018 | Marici et al. |
| 9,993,634 B2 | 6/2018 | Christensen et al. |
| 10,010,685 B2 | 7/2018 | Ferreri et al. |
| 10,039,884 B2 | 8/2018 | Ferreri et al. |
| 10,046,155 B2 | 8/2018 | Carter et al. |
| 10,064,576 B2 | 9/2018 | Devgon |
| 10,065,020 B2 | 9/2018 | Gaur |
| 10,076,272 B2 | 9/2018 | Devgon et al. |
| 10,105,085 B2 | 10/2018 | Andreae et al. |
| 10,105,494 B2 | 10/2018 | Alheidt et al. |
| 10,143,411 B2 | 12/2018 | Cabot |
| 10,159,531 B2 | 12/2018 | Misener et al. |
| 10,182,753 B2 | 1/2019 | Davis et al. |
| 10,219,982 B2 | 3/2019 | Weir et al. |
| 10,232,140 B2 | 3/2019 | McKinnon |
| 10,300,247 B2 | 5/2019 | Devgon et al. |
| 10,307,571 B2 | 6/2019 | Burkholz |
| 10,391,031 B2 | 8/2019 | Yevmenenko et al. |
| 10,426,929 B2 | 10/2019 | Burkholz et al. |
| 10,441,752 B2 | 10/2019 | Bierman et al. |
| 10,441,774 B2 | 10/2019 | Kaczorowski |
| 10,525,236 B2 | 1/2020 | Belson |
| 10,576,260 B2 | 3/2020 | Kaczorowski |
| 10,674,950 B2 | 6/2020 | Devgon |
| 10,729,367 B1 | 8/2020 | Devgon |
| 10,773,056 B2 | 9/2020 | Funk et al. |
| 11,071,529 B2 | 7/2021 | Heske et al. |
| 11,083,841 B2 | 8/2021 | Mathias et al. |
| 11,097,083 B2 | 8/2021 | Burkholz et al. |
| 11,147,957 B2 | 10/2021 | Burkholz et al. |
| 11,173,277 B2 | 11/2021 | Burkholz et al. |
| 11,291,804 B2 | 4/2022 | Bierman et al. |
| 2002/0091355 A1 | 7/2002 | Hayden |
| 2002/0120215 A1 | 8/2002 | Crawford et al. |
| 2003/0009150 A1 | 1/2003 | Pepin |
| 2003/0055401 A1 | 3/2003 | Larson et al. |
| 2003/0083620 A1 | 5/2003 | Luther et al. |
| 2003/0114871 A1 | 6/2003 | Turnbull |
| 2003/0199836 A1 | 10/2003 | Tiernan et al. |
| 2004/0073171 A1 | 4/2004 | Rogers et al. |
| 2004/0092879 A1 | 5/2004 | Kraus et al. |
| 2004/0138622 A1 | 7/2004 | Palasis |
| 2004/0158229 A1 | 8/2004 | Quinn |
| 2004/0181192 A1 | 9/2004 | Cuppy |
| 2005/0015048 A1 | 1/2005 | Chiu et al. |
| 2005/0090801 A1 | 4/2005 | Racz et al. |
| 2005/0090802 A1 | 4/2005 | Conners, III et al. |
| 2005/0096609 A1 | 5/2005 | Maginot et al. |
| 2005/0119597 A1 | 6/2005 | O'Mahony et al. |
| 2005/0165355 A1 | 7/2005 | Fitgerald |
| 2005/0192558 A1 | 9/2005 | Bernard et al. |
| 2005/0251191 A1 | 11/2005 | Taylor et al. |
| 2005/0273076 A1 | 12/2005 | Beasley et al. |
| 2006/0015068 A1 | 1/2006 | Amisar et al. |
| 2006/0016478 A1 | 1/2006 | Chantalat |
| 2006/0100582 A1 | 5/2006 | Marianowicz et al. |
| 2006/0142694 A1 | 6/2006 | Bednarek et al. |
| 2006/0155209 A1 | 7/2006 | Miller et al. |
| 2006/0155244 A1 | 7/2006 | Popov |
| 2006/0293612 A1 | 12/2006 | Jenson et al. |
| 2007/0088257 A1 | 4/2007 | Fisher et al. |
| 2007/0088279 A1 | 4/2007 | Shue et al. |
| 2007/0100295 A1 | 5/2007 | Belley et al. |
| 2007/0219460 A1 | 9/2007 | Goldenberg |
| 2007/0225684 A1 | 9/2007 | Wentling et al. |
| 2007/0282280 A1 | 12/2007 | Tennican |
| 2008/0009784 A1 | 1/2008 | Leedle et al. |
| 2008/0033396 A1 | 2/2008 | Danek et al. |
| 2008/0045862 A1 | 2/2008 | Dalebout et al. |
| 2008/0051717 A1 | 2/2008 | Voss et al. |
| 2008/0077085 A1 | 3/2008 | Eidenschink et al. |

(56) References Cited

U.S. PATENT DOCUMENTS

| | | |
|---|---|---|
| 2008/0287918 A1 | 11/2008 | Rosenman et al. |
| 2008/0300574 A1 | 12/2008 | Belson et al. |
| 2008/0312671 A1 | 12/2008 | Riles et al. |
| 2008/0319386 A1 | 12/2008 | Bonnette et al. |
| 2008/0319387 A1 | 12/2008 | Amisar et al. |
| 2009/0105638 A1 | 4/2009 | Partlett et al. |
| 2009/0156963 A1 | 6/2009 | Noble et al. |
| 2009/0192496 A1 | 7/2009 | Suwito et al. |
| 2009/0209912 A1 | 8/2009 | Keyser et al. |
| 2010/0114017 A1 | 5/2010 | Lenker et al. |
| 2010/0130936 A1 | 5/2010 | Voss |
| 2010/0160863 A1 | 6/2010 | Heuser |
| 2010/0210934 A1 | 8/2010 | Belson |
| 2010/0286657 A1 | 11/2010 | Heck |
| 2010/0305519 A1 | 12/2010 | McKinnon et al. |
| 2011/0015577 A1 | 1/2011 | Baney et al. |
| 2011/0166525 A1 | 7/2011 | Tanabe et al. |
| 2012/0016307 A1 | 1/2012 | Burkholz et al. |
| 2012/0041392 A1 | 2/2012 | Donawick |
| 2012/0046648 A1 | 2/2012 | Scheckel |
| 2012/0053523 A1 | 3/2012 | Harding |
| 2012/0109079 A1 | 5/2012 | Asleson et al. |
| 2012/0157968 A1 | 6/2012 | Eldredge et al. |
| 2012/0191010 A1 | 7/2012 | Cabot |
| 2012/0197200 A1 | 8/2012 | Belson |
| 2012/0277630 A1 | 11/2012 | Devgon |
| 2012/0283640 A1 | 11/2012 | Anderson et al. |
| 2013/0121897 A1 | 5/2013 | Davis et al. |
| 2013/0131597 A1 | 5/2013 | Blaivas et al. |
| 2013/0281925 A1 | 10/2013 | Benscoter et al. |
| 2013/0289537 A1 | 10/2013 | Schertiger et al. |
| 2014/0012085 A1 | 1/2014 | Smith et al. |
| 2014/0046214 A1 | 2/2014 | Devgon |
| 2014/0107427 A1 | 4/2014 | Chow et al. |
| 2014/0107800 A1 | 4/2014 | Flom et al. |
| 2014/0128774 A1 | 5/2014 | Andreae et al. |
| 2014/0128775 A1 | 5/2014 | Andreae et al. |
| 2014/0171803 A1 | 6/2014 | Van Hoven et al. |
| 2014/0180127 A1 | 6/2014 | Meyer et al. |
| 2014/0188002 A1 | 7/2014 | Close et al. |
| 2014/0188003 A1 | 7/2014 | Belson |
| 2014/0296745 A1 | 10/2014 | Cash |
| 2014/0358120 A1 | 12/2014 | Haarala et al. |
| 2014/0364766 A1 | 12/2014 | Devgon et al. |
| 2014/0378867 A1 | 12/2014 | Belson |
| 2015/0005669 A1 | 1/2015 | Burkholz |
| 2015/0038909 A1 | 2/2015 | Christensen et al. |
| 2015/0065952 A1 | 3/2015 | Pacheco et al. |
| 2015/0119859 A1 | 4/2015 | Cajamarca et al. |
| 2015/0119863 A1 | 4/2015 | Christensen et al. |
| 2015/0123398 A1 | 5/2015 | Sanders et al. |
| 2015/0148747 A1 | 5/2015 | Whitley |
| 2015/0208973 A1 | 7/2015 | Burkholz |
| 2015/0209510 A1 | 7/2015 | Burkholz et al. |
| 2015/0297456 A1 | 10/2015 | Marici et al. |
| 2015/0306345 A1 | 10/2015 | Burkholz et al. |
| 2015/0313526 A1 | 11/2015 | Van Wieren |
| 2015/0320937 A1 | 11/2015 | Kosinski et al. |
| 2015/0360005 A1 | 12/2015 | Arellano Cabrera et al. |
| 2016/0008517 A1 | 1/2016 | Burkholz et al. |
| 2016/0015945 A1 | 1/2016 | Warrlng et al. |
| 2016/0022963 A1 | 1/2016 | Belson |
| 2016/0038067 A1 | 2/2016 | Davis et al. |
| 2016/0067391 A1 | 3/2016 | Real et al. |
| 2016/0073937 A1 | 3/2016 | Burkholz et al. |
| 2016/0166772 A1 | 6/2016 | Mirzazadeh et al. |
| 2016/0206858 A1 | 7/2016 | Ishida |
| 2016/0220786 A1 | 8/2016 | Mitchell et al. |
| 2016/0220790 A1 | 8/2016 | Borowicz |
| 2016/0220805 A1 | 8/2016 | Goral et al. |
| 2017/0043066 A1 | 2/2017 | Laub |
| 2017/0056595 A1 | 3/2017 | Alheidt et al. |
| 2017/0119997 A1 | 5/2017 | Burkholz et al. |
| 2017/0120008 A1 | 5/2017 | Burkholz et al. |
| 2017/0216564 A1 | 8/2017 | Devgon et al. |
| 2017/0265746 A1 | 9/2017 | Rajendran et al. |
| 2017/0319822 A1 | 11/2017 | Ang |
| 2017/0368315 A1 | 12/2017 | Leinsing et al. |
| 2018/0028800 A1 | 2/2018 | Devgon et al. |
| 2018/0154112 A1 | 6/2018 | Chan et al. |
| 2018/0160958 A1 | 6/2018 | Baid |
| 2018/0161546 A1 | 6/2018 | Aslam et al. |
| 2018/0272106 A1 | 9/2018 | Funk et al. |
| 2018/0272107 A1 | 9/2018 | Ehrenreich et al. |
| 2018/0317830 A1* | 11/2018 | Devgon ........... A61B 5/150946 |
| 2018/0318557 A1 | 11/2018 | Burkholz et al. |
| 2018/0339131 A1 | 11/2018 | Muse et al. |
| 2018/0344983 A1 | 12/2018 | Funk et al. |
| 2019/0001031 A1 | 1/2019 | Real et al. |
| 2019/0021640 A1 | 1/2019 | Burkholz et al. |
| 2019/0022367 A1 | 1/2019 | Burkholz et al. |
| 2019/0160275 A1 | 5/2019 | Funk et al. |
| 2019/0201668 A1 | 7/2019 | Funk et al. |
| 2019/0255294 A1 | 8/2019 | Mitchell et al. |
| 2019/0275302 A1 | 9/2019 | Devgon et al. |
| 2019/0328370 A1 | 10/2019 | Muse |
| 2020/0001044 A1 | 1/2020 | Ramanathan |
| 2020/0016374 A1 | 1/2020 | Burkholz et al. |
| 2020/0023166 A1 | 1/2020 | Burkholz et al. |
| 2020/0023176 A1 | 1/2020 | Hu et al. |
| 2020/0061343 A1 | 2/2020 | Kumar et al. |
| 2020/0078564 A1 | 3/2020 | Blanchard et al. |
| 2020/0078565 A1 | 3/2020 | Scherich et al. |
| 2020/0094016 A1 | 3/2020 | Breindel et al. |
| 2020/0100716 A1* | 4/2020 | Devgon ........... A61B 5/150732 |
| 2020/0170559 A1 | 6/2020 | Burkholz et al. |
| 2020/0230353 A1 | 7/2020 | Burkholz et al. |
| 2020/0230358 A1* | 7/2020 | Devgon ............. A61B 5/15003 |
| 2020/0352497 A1 | 11/2020 | Brewer et al. |
| 2020/0406008 A1 | 12/2020 | Funk et al. |
| 2021/0052851 A1 | 2/2021 | Devgon et al. |
| 2021/0060306 A1 | 3/2021 | Kumar |
| 2021/0068732 A1 | 3/2021 | Yan et al. |
| 2021/0085230 A1 | 3/2021 | Brewer et al. |
| 2021/0196167 A1 | 7/2021 | Vandenbrink et al. |
| 2021/0212618 A1 | 7/2021 | Burkholz et al. |
| 2021/0213245 A1 | 7/2021 | Burkholz et al. |
| 2021/0275069 A1 | 9/2021 | Ma et al. |
| 2021/0290126 A1 | 9/2021 | Burkholz et al. |
| 2021/0290264 A1 | 9/2021 | Harding et al. |
| 2021/0290897 A1 | 9/2021 | Burkholz et al. |
| 2021/0290901 A1 | 9/2021 | Burkholz et al. |
| 2021/0290906 A1 | 9/2021 | Burkholz et al. |
| 2021/0290914 A1 | 9/2021 | Burkholz et al. |
| 2021/0290926 A1 | 9/2021 | Scherich et al. |
| 2021/0299426 A1 | 9/2021 | Scherich et al. |
| 2021/0345919 A1 | 11/2021 | Brewer et al. |
| 2021/0345920 A1 | 11/2021 | Brewer et al. |
| 2021/0345921 A1 | 11/2021 | Brewer et al. |
| 2021/0345922 A1 | 11/2021 | Brewer et al. |
| 2021/0346653 A1 | 11/2021 | Burkholz et al. |
| 2022/0001161 A1 | 1/2022 | Burkholz et al. |
| 2022/0104741 A1 | 4/2022 | Brewer et al. |
| 2022/0110561 A1 | 4/2022 | Blanchard et al. |
| 2022/0161003 A1 | 5/2022 | Cook |
| 2022/0176079 A1 | 6/2022 | Cook |

FOREIGN PATENT DOCUMENTS

| | | |
|---|---|---|
| EP | 0792655 A2 | 9/1997 |
| EP | 2504054 B1 | 9/2019 |
| GB | 2016274 A | 9/1979 |
| JP | 2000254235 A | 9/2000 |
| JP | 2007029732 A | 2/2007 |
| WO | 1987007493 | 12/1987 |
| WO | 1996021393 A1 | 7/1996 |
| WO | 2000041617 A1 | 7/2000 |
| WO | 2000049939 A1 | 8/2000 |
| WO | 2001089621 A1 | 11/2001 |
| WO | 2006065949 A2 | 6/2006 |
| WO | 2006090637 A1 | 7/2008 |
| WO | 2008097949 A1 | 8/2008 |
| WO | 2008130077 A1 | 10/2008 |
| WO | 2008138351 A1 | 11/2008 |

(56) References Cited

FOREIGN PATENT DOCUMENTS

| | | |
|---|---|---|
| WO | 2009029216 A1 | 3/2009 |
| WO | 2009152470 A1 | 12/2009 |
| WO | 2010065901 A1 | 6/2010 |
| WO | 2010089154 A1 | 8/2010 |
| WO | 2010107949 A1 | 9/2010 |
| WO | 2011011436 A2 | 1/2011 |
| WO | 2011030282 A1 | 3/2011 |
| WO | 2012064786 A1 | 5/2012 |
| WO | 2012149109 A2 | 11/2012 |
| WO | 2014093472 A1 | 6/2014 |
| WO | 2016033143 A1 | 3/2016 |
| WO | 2018217781 A1 | 11/2018 |
| WO | 2018218236 A1 | 11/2018 |
| WO | 2020055582 A1 | 3/2020 |
| WO | 2020061075 A1 | 3/2020 |
| WO | 2020068759 A1 | 4/2020 |
| WO | 2020112666 A1 | 6/2020 |
| WO | 2020150503 A1 | 7/2020 |
| WO | 2021041048 A1 | 3/2021 |
| WO | 2021050603 A1 | 3/2021 |
| WO | 2021141765 A1 | 7/2021 |
| WO | 2021141766 A1 | 7/2021 |
| WO | 2021183307 A1 | 9/2021 |
| WO | 2021194757 A1 | 9/2021 |
| WO | 2021194758 A1 | 9/2021 |
| WO | 2021194759 A1 | 9/2021 |
| WO | 2021194761 A1 | 9/2021 |
| WO | 2021194785 A1 | 9/2021 |
| WO | 2021194788 A1 | 9/2021 |
| WO | 2021194789 A1 | 9/2021 |
| WO | 2021195054 A1 | 9/2021 |
| WO | 2021236530 A1 | 11/2021 |
| WO | 2022032242 A1 | 2/2022 |
| WO | 2022076640 A1 | 4/2022 |
| WO | 2022115653 A1 | 6/2022 |

OTHER PUBLICATIONS

International Searching Authority, International Search Report and Written Opinion of the International Searching Authority in Patent Cooperation Treaty International Application No. PCT/US2021/032785, dated Oct. 26, 2021, 16 pages.
International Searching Authority, International Search Report and Written Opinion of the International Searching Authority in Patent Cooperation Treaty International Application No. PCT/US2021/045290, dated Nov. 17, 2021, 12 pages.
Becton, Dickinson and Company, Connect and Protect with BD Vacutainer® Luer-Lok™ Access Device, dated 2010, 2 pages.
Jagger et al., Drawing Venous Blood With Syringes: a Risky Use of Injection Equipment, Advances in Exposure Prevention, vol. 5, No. 3, reprinted at ResearchGate, dated Jan. 2000, 5 pages.
Nursing Research Council of United Hospital, Evidence-Based Practice (EBP) Guideline: Drawing Labs from Peripheral IV Sites, dated Mar. 2009, 3 pages.
World Health Organization, WHO guidelines on drawing blood: best practices in phlebotomy, dated 2010, 125 pages.

\* cited by examiner

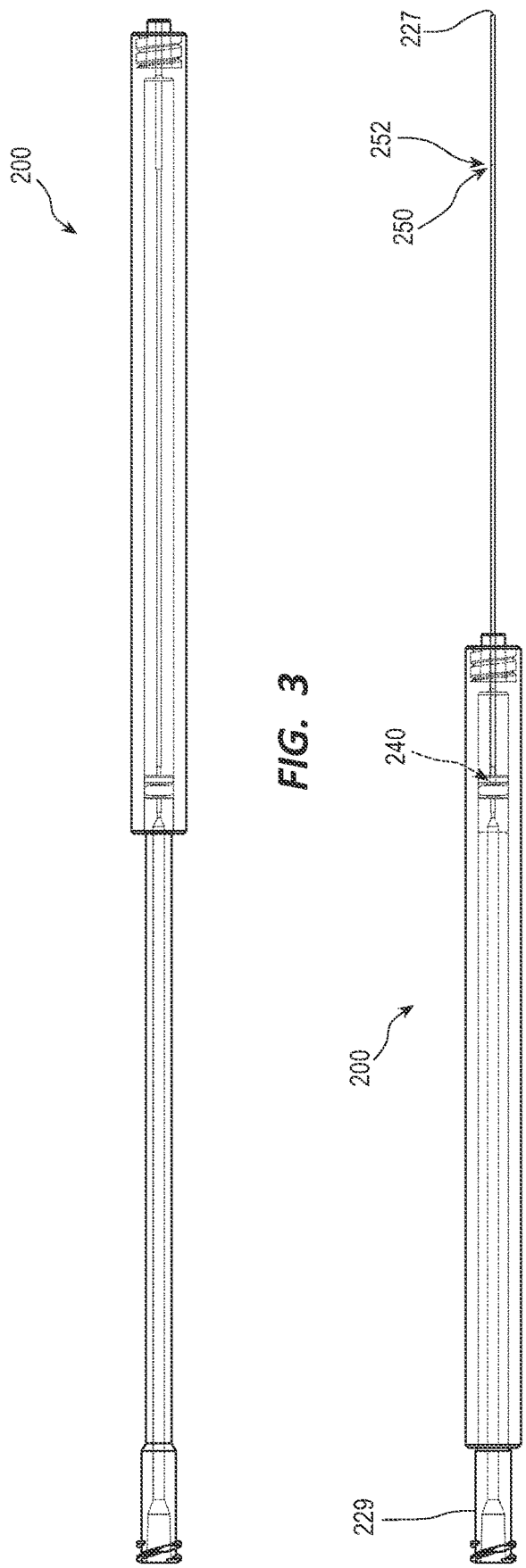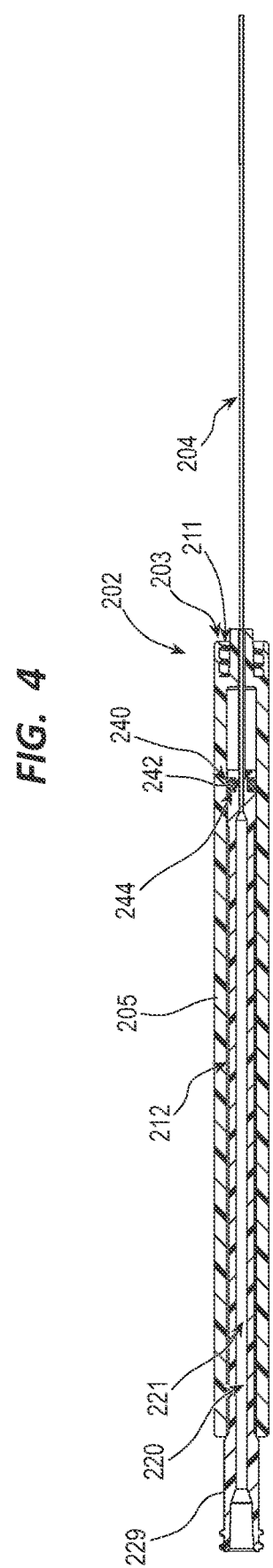
FIG. 3
FIG. 4
FIG. 5

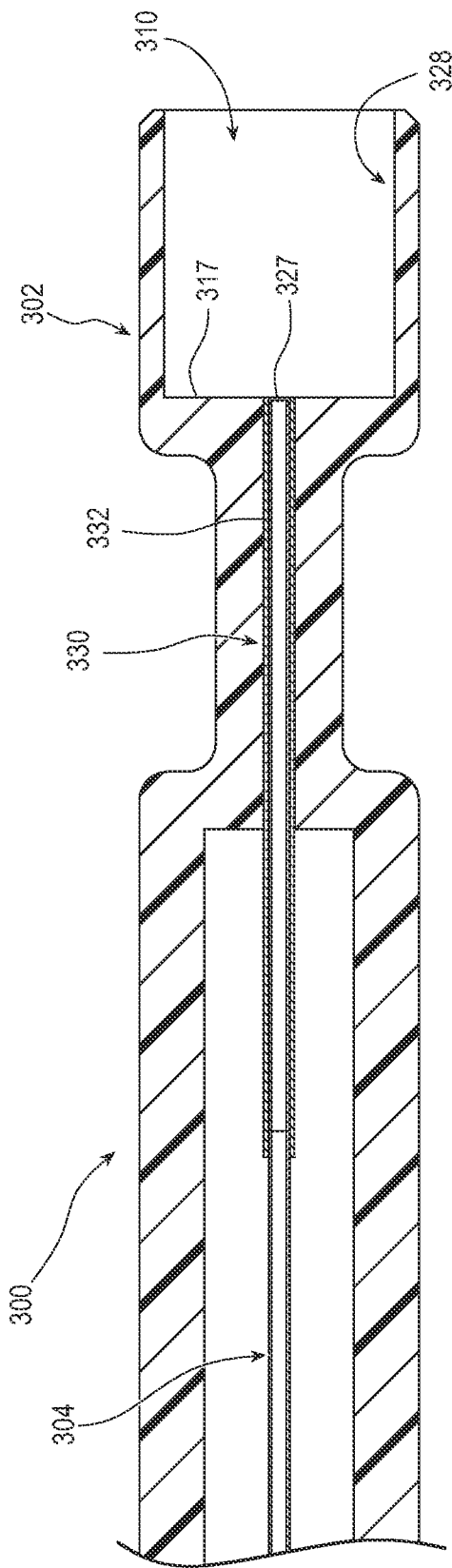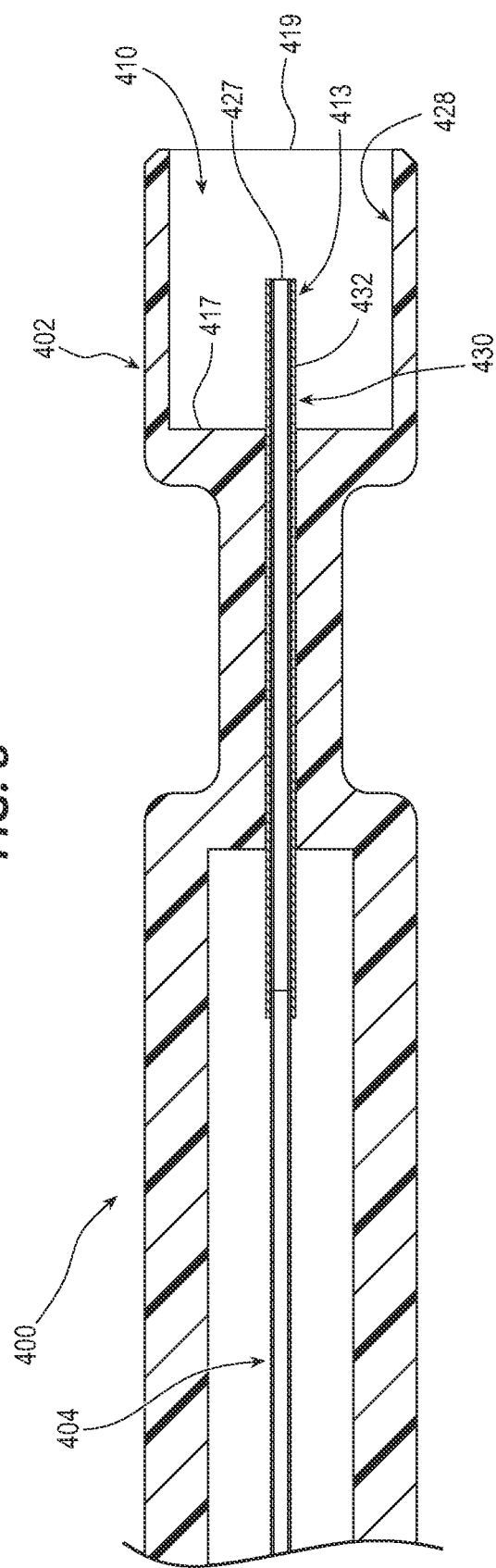

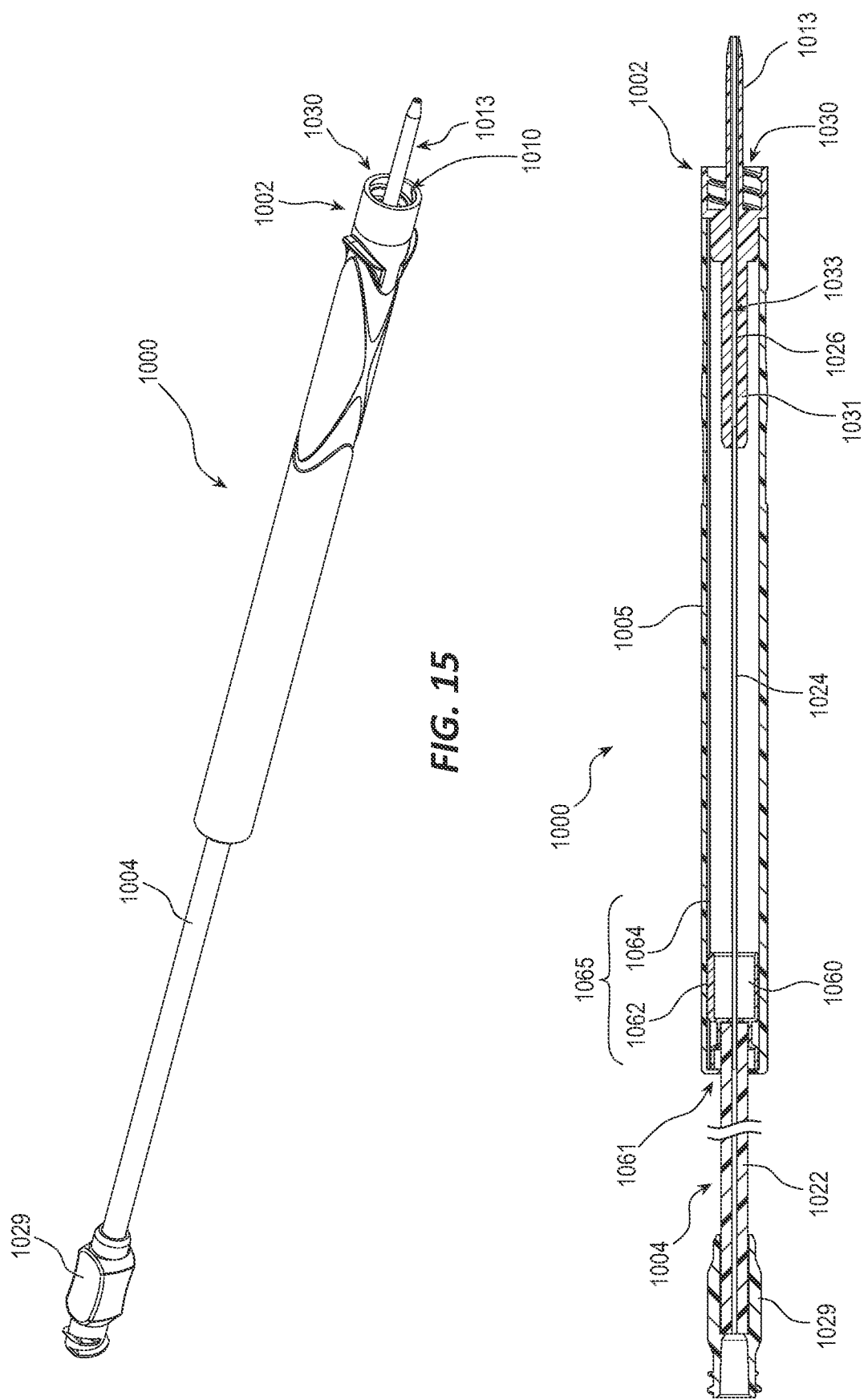

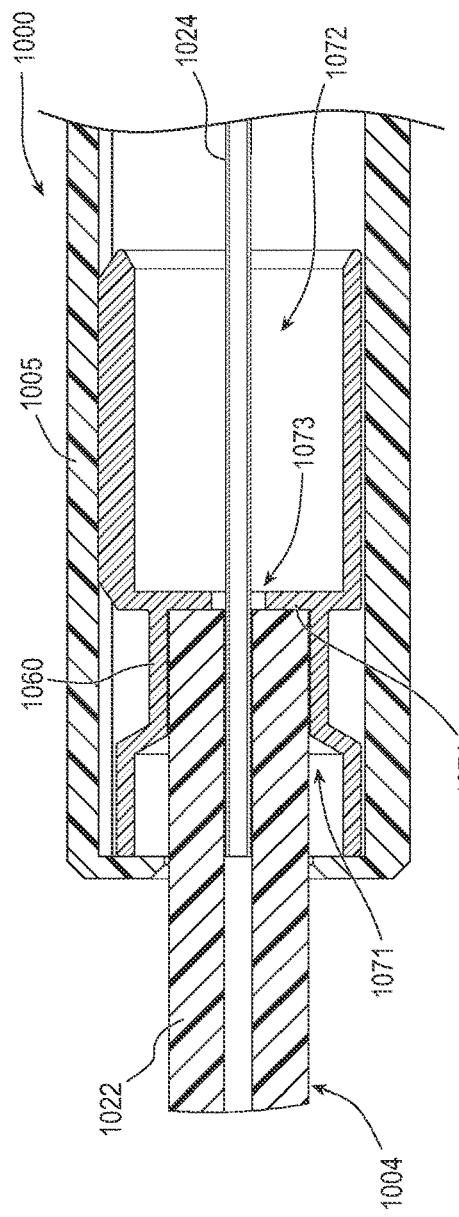
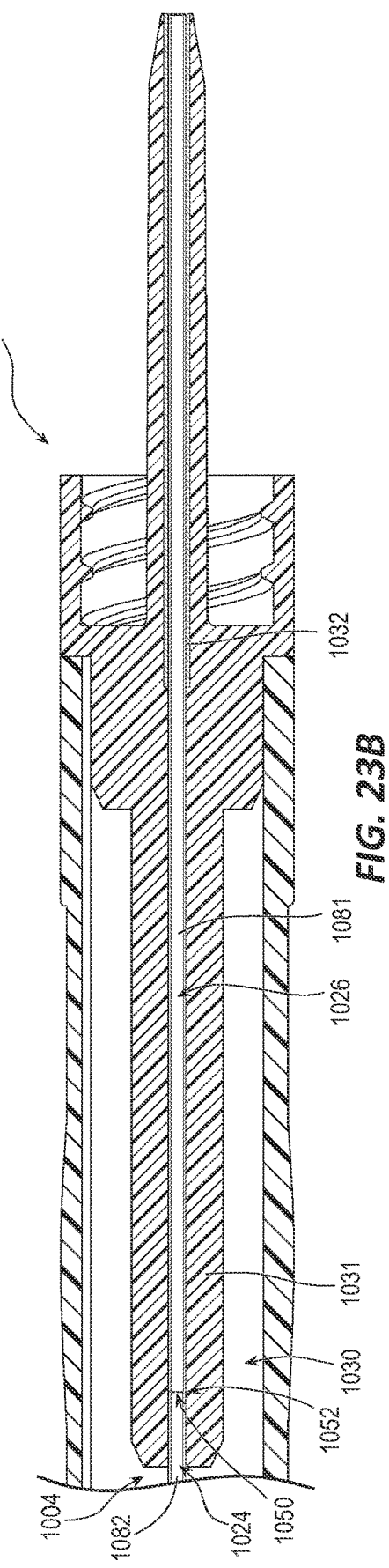
FIG. 23A
FIG. 23B

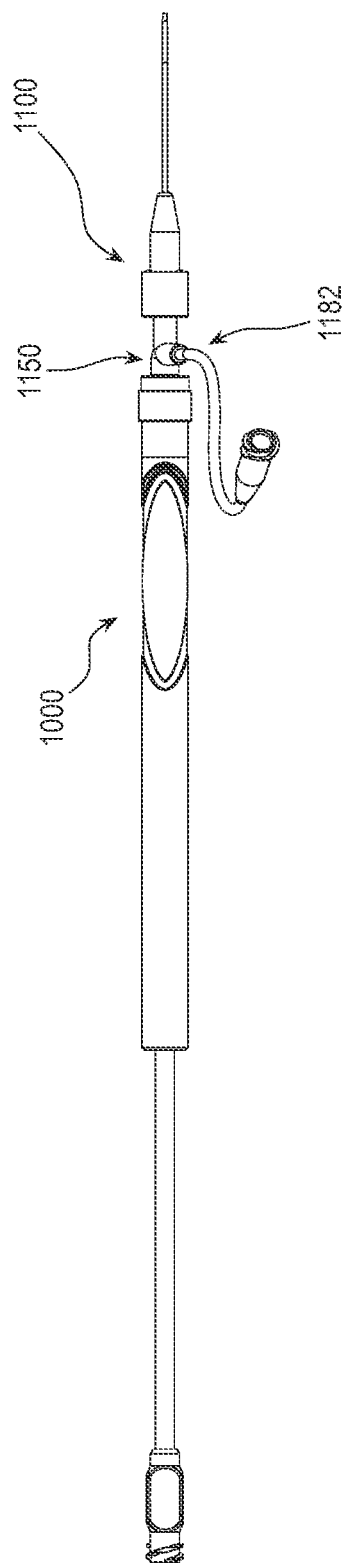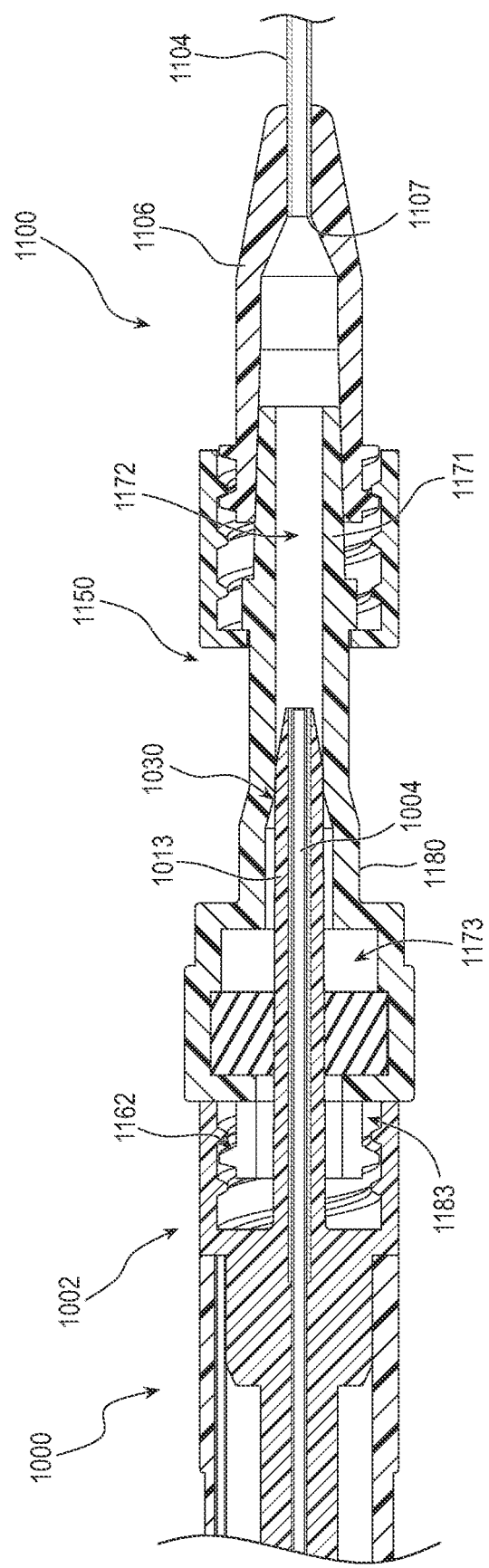
FIG. 26
FIG. 27

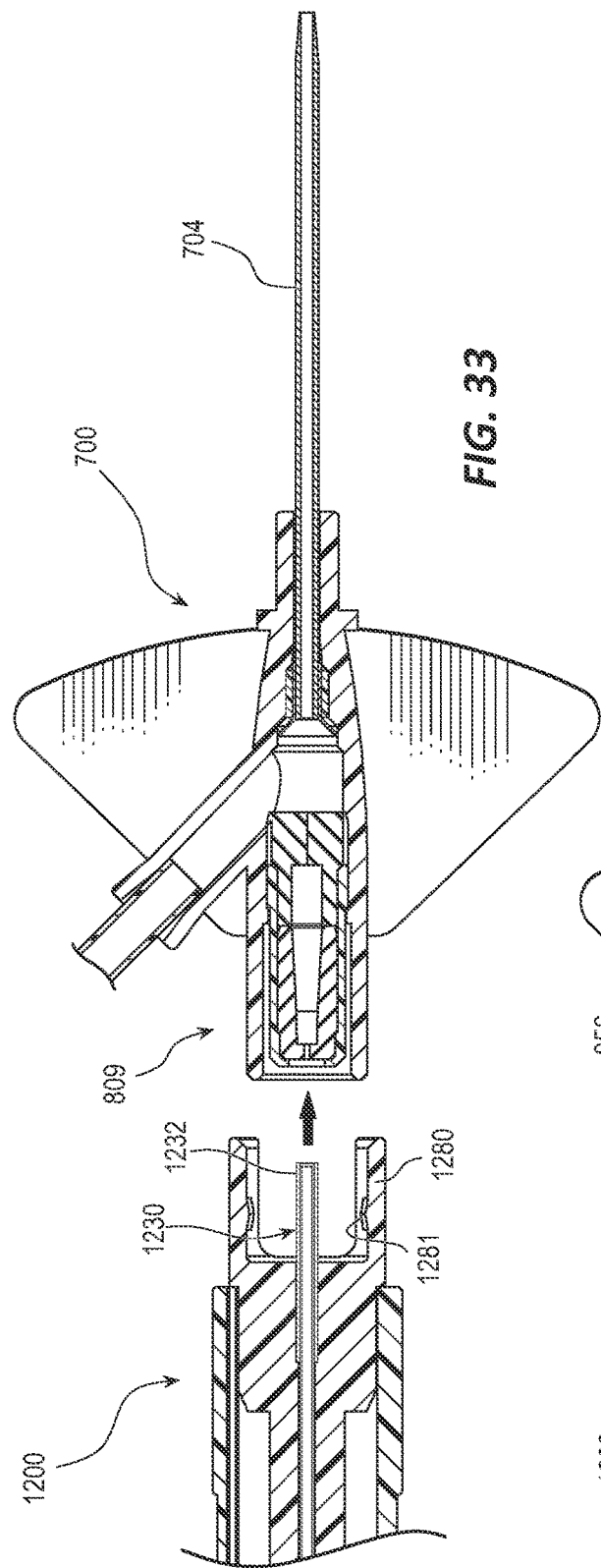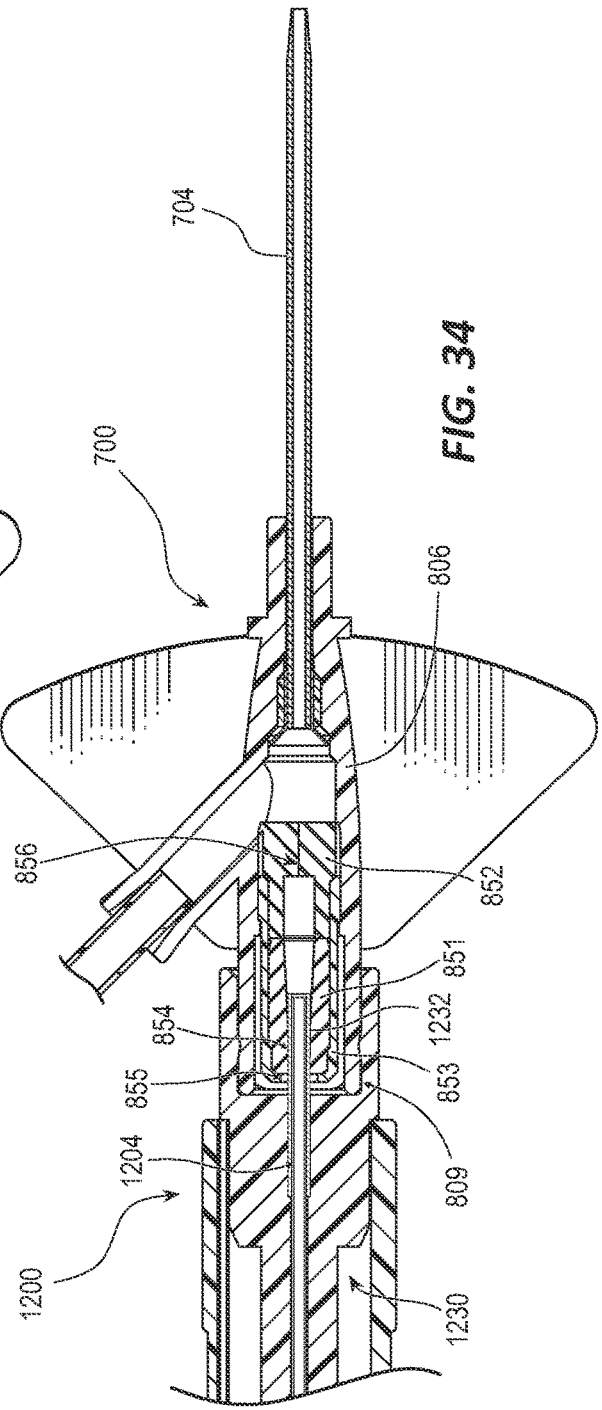

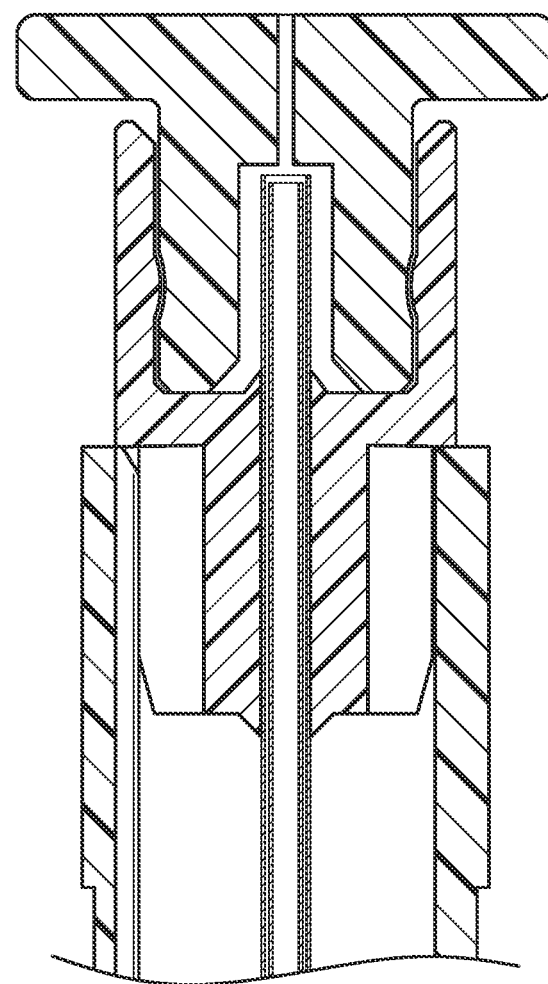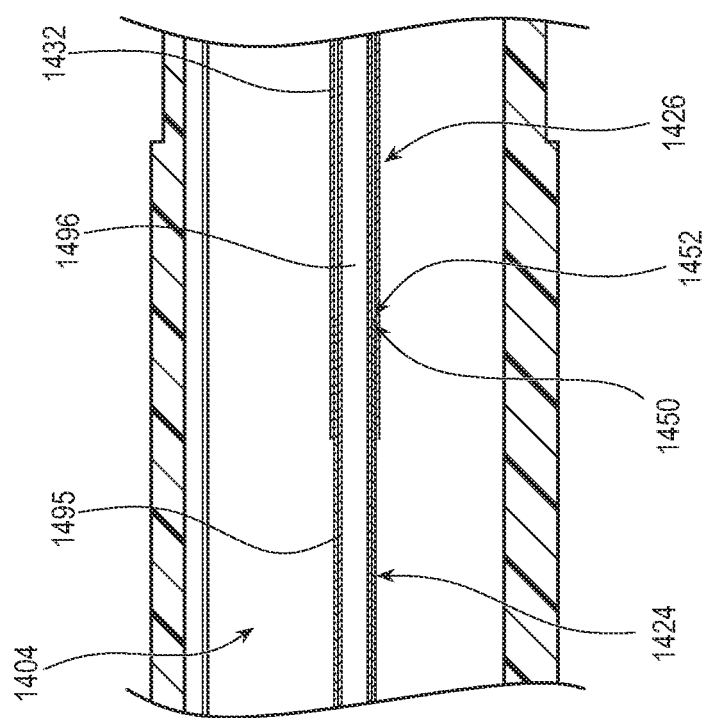
FIG. 56A

BLOOD COLLECTION DEVICES, SYSTEMS, AND METHODS

CROSS-REFERENCE TO RELATED APPLICATIONS

This application is a continuation of U.S. patent application Ser. No. 17/676,964, filed Feb. 22, 2022, titled BLOOD COLLECTION DEVICES, SYSTEMS, AND METHODS, which is a continuation of U.S. patent application Ser. No. 17/535,821, filed Nov. 26, 2021, titled BLOOD COLLECTION DEVICES, SYSTEMS, AND METHODS, which claims priority to each of U.S. Provisional Patent Application No. 63/118,679, filed Nov. 26, 2020, titled BLOOD COLLECTION DEVICES, SYSTEMS, AND METHODS, U.S. Provisional Patent Application No. 63/225,992, filed Jul. 27, 2021, titled BLOOD COLLECTION DEVICES, SYSTEMS, AND METHODS, and U.S. Provisional Patent Application No. 63/256,625, filed Oct. 17, 2021, titled BLOOD COLLECTION DEVICES, SYSTEMS, AND METHODS; the entire contents of each of the foregoing applications are hereby incorporated by reference herein.

TECHNICAL FIELD

Certain embodiments described herein relate generally to devices, systems, and methods for blood collection and further embodiments relate more particularly to devices, systems, and methods for facilitating blood collection via a previously placed catheter, such as, for example, a peripheral intravenous catheter.

BACKGROUND

Known devices, systems, and methods for drawing blood, including drawing blood using a previously placed catheter, suffer from a variety of drawbacks. Embodiments disclosed herein remedy, ameliorate, or avoid one or more of such drawbacks. Other or further uses and methods are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 3 is a side elevation view of the access system of FIG. 2 in the undeployed or retracted state;

FIG. 4 is another side elevation view of the access system of FIG. 2 in a fully deployed or advanced state;

FIG. 5 is a cross-sectional view through a longitudinal axis of the access system of FIG. 2, with the access system in the fully deployed or advanced state;

FIG. 8 is a cross-sectional view of a distal portion of another embodiment of an access system shown in an undeployed or retracted state;

FIG. 9 is a cross-sectional view of a distal portion of another embodiment of an access system shown in an undeployed or retracted state;

FIG. 15 is a perspective view of another embodiment of an access system configured to be coupled with embodiments of a base catheter system, the access system being shown in an undeployed or retracted state;

FIG. 16 is a cross-sectional view of the access system of FIG. 15 in the undeployed or retracted state;

FIG. 23A is a cross-sectional view of a generally proximal portion of the access system of FIG. 15 in a retracted state;

FIG. 23B is a cross-sectional view of a distal portion of the access system of FIG. 15 in the retracted state;

FIG. 26 is a side elevation view of the access system of FIG. 15 in the retracted state coupled with the assembled base catheter assembly of FIG. 25;

FIG. 27 is a cross-sectional view of a distal portion of the access system of FIG. 15 in the retracted state coupled with the assembled base catheter assembly of FIG. 25;

FIG. 33 is a cross-sectional view of a distal end of the access system of FIG. 30, while in the retracted or undeployed state, being advanced toward an embodiment of a closed intravenous catheter system, such as the closed intravenous catheter system of FIG. 12, for coupling therewith;

FIG. 34 is a cross-sectional view of the distal end of the access system of FIG. 30, while in the retracted or undeployed state, coupled with the closed intravenous catheter system;

FIG. 56A is an enlarged cross-sectional view of a distal region of the access system of FIG. 54 in the retracted state;

DETAILED DESCRIPTION

Figure 1A:
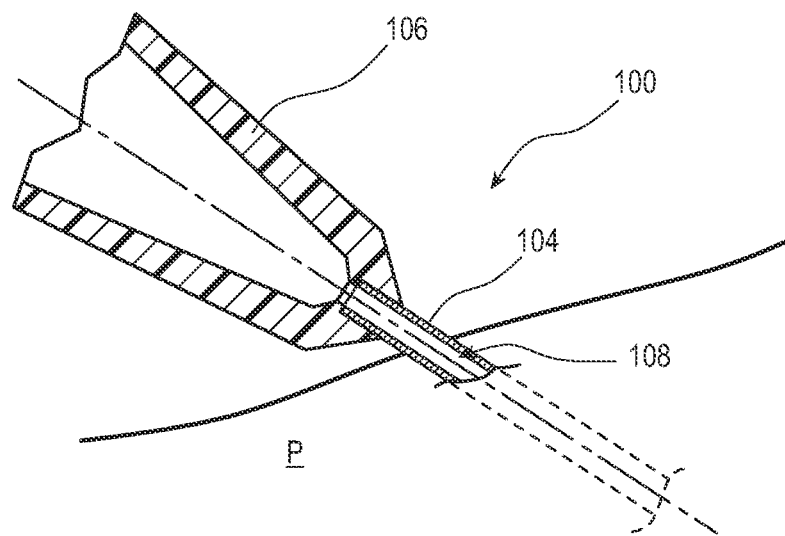
FIG. 1A is a schematic cross-sectional view of a proximal portion of an embodiment of a base catheter system placed within a patient.

Embodiments of the present disclosure relate generally to devices, systems, and methods for blood collection (also referred to as blood draws, blood aspiration, phlebotomy procedures, etc.). The blood collection can be achieved via an access system that includes a conduit or cannula that is inserted into a previously placed catheter, such as a catheter tube of a previously placed catheter, such as, for example, a previously placed peripheral intravenous (PIV) catheter. In certain embodiments, the access system can provide a desirable alternative to venipuncture.

In one context, fluid, particularly blood, is drawn from patients on a routine basis in many hospitals, clinics, and laboratories. One of the most common ways to draw blood is venipuncture, which is a method that involves inserting a needle through the skin and into an underlying vein to provide access to the patient's blood. In some instances, blood can be drawn as frequently as every six hours. Further, patients can be subjected to multiple attempts each time a needle is inserted into the skin, and the more frequent the withdrawals become, the more difficult it can become to find a location for the next withdrawal. Each attempt can be painful and a nuisance. Difficult intravenous access (DIVA) is a common problem that affects numerous patients. Other options for the withdrawal of blood and other fluids, however, are limited, and can often be even more painful than venipuncture. Some of these options include the use of peripherally inserted central catheters (PICC lines), central lines, repeated peripheral venipuncture, and groin sticks.

In some instances, blood may be drawn via a peripheral intravenous catheter at the time of insertion. In many instances, however, clots or fibrin sheaths can form at the tip of an intravenous catheter over time, so it is generally not desirable to draw blood from peripheral intravenous catheters, as previously designed, at any significant time after placement. In various instances, the obstructions that form at the distal tip can fully obstruct the distal tip, thereby entirely preventing withdrawal of blood through the catheter. In other instances, the obstructions may only partially obstruct the distal tip, but may affect fluid flow through the catheter in such a way as to promote hemolysis and/or otherwise reduce the quality of the blood withdrawn through the catheter and/or reduce a speed of the withdrawal.

In some instances, the intravenous catheter can lack sufficient rigidity to remain fully patent during a blood draw. For example, in some instances, the catheter is formed of a material that softens over time when within the patient vasculature. While blood draws may be possible upon initial placement of the catheter, blood draws may become increasingly difficult and ultimately impossible after the initial placement as the catheter softens. The catheter lumen may collapse when negative pressure applied at a proximal end of the catheter for an attempted blood draw, thereby inhibiting or preventing blood withdrawal.

In certain instances, even when blood is able to be withdrawn through a softened catheter, the quality of the drawn blood, relative to the quality of blood drawn immediately after placement of the catheter, may deteriorate as the catheter softens. Without being bound by theory, this quality reduction may be due to the lumen defined by the catheter becoming more tortuous or otherwise changing shape as the catheter softens. For example, upon initial placement, the catheter may have relatively few curves and/or regions of the catheter that extend through the skin and the vessel wall may define a rounded cross-sectional profile. Over time, the softening or softened catheter may become compliant so as to conform to tortuous anatomy through which it passes and/or the cross-sectional profile at the insertion regions may flatten or otherwise change shape. Blood drawn through these altered regions may, for example, be more susceptible to hemolysis.

In still other or further instances, an opening at the catheter tip may suction against a feature of the vessel anatomy, such as a valve or the vessel wall, during an attempted blood draw, thereby preventing blood withdrawal through the opening.

For one or more of the foregoing reasons, and/or for other possible reasons, it can be desirable to provide a conduit or cannula through a previously placed catheter (e.g., a PIV catheter) to achieve a high-quality blood draw through the catheter. The terms "conduit" and "cannula" may be used interchangeably herein. In some instances, the cannula can have sufficient rigidity to provide or maintain a patent lumen through which blood can readily pass. In other or further instances, the cannula can be readily inserted through tortuous path into and/or through a blood vessel. In other or further instances, the distal end of the cannula may be placed distally relative to the tip of the previously placed catheter, which may, for example, avoid interference from clots or fibrin sheaths; permit access to a region beyond an otherwise obstructing anatomical feature, such as by moving past one or more venous valves and/or away from a vessel wall; permit movement to a region of increased blood flow; and/or move away from a region of vascular trauma due to venipuncture and catheter insertion, any or all of which can result in substantially improved blood draws, such as, for example, by establishing blood flow and/or by reducing hemolysis of the sampled blood.

Certain embodiments disclosed herein can remedy, ameliorate, or avoid one or more limitations or drawbacks of known systems in which a catheter is inserted through a previously placed catheter for purposes of blood collection. One or more of these and/or other advantages will be apparent from the present disclosure.

For example, in some instances, a catheter is introduced into a patient, and subsequently, a cannula is introduced into the patient through the catheter. The catheter may be referred to herein as a placed catheter, a preplaced catheter, an anchor catheter, or a base catheter. The cannula may, in some instances, also be referred to as a conduit, a fluid channeler, a fluid extraction member, etc. In many instances, the cannula will have properties different from the placed catheter. For example, in some instances, at least a portion of the cannula may be stiffer or more rigid than the placed catheter. The cannula may, in some instances, define an open lumen or passageway through which blood can pass from the vessel and out of the patient through the cannula into any suitable blood collection device. The cannula may, in some instances, be reinforced so as to avoid buckling or kinking in order to readily enter and extend through a tortuous path of a lumen defined by the catheter. In some instances, the cannula may straighten or otherwise reduce a tortuousness of a path through a preplaced catheter system. In some instances, the cannula may be advanced past a distal end of the placed catheter.

Figure 1B:
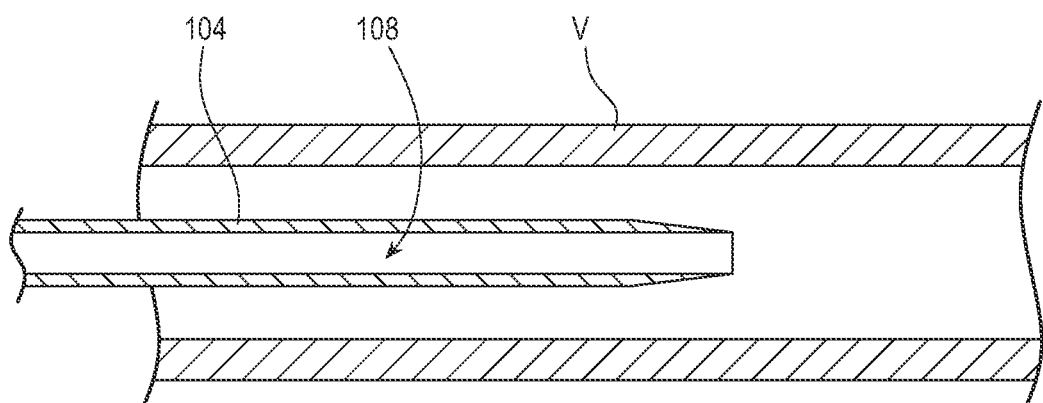
FIG. 1B is a schematic cross-sectional view of a distal end of the base catheter system of FIG. 1A within a blood vessel of a patient.
Figure 2:
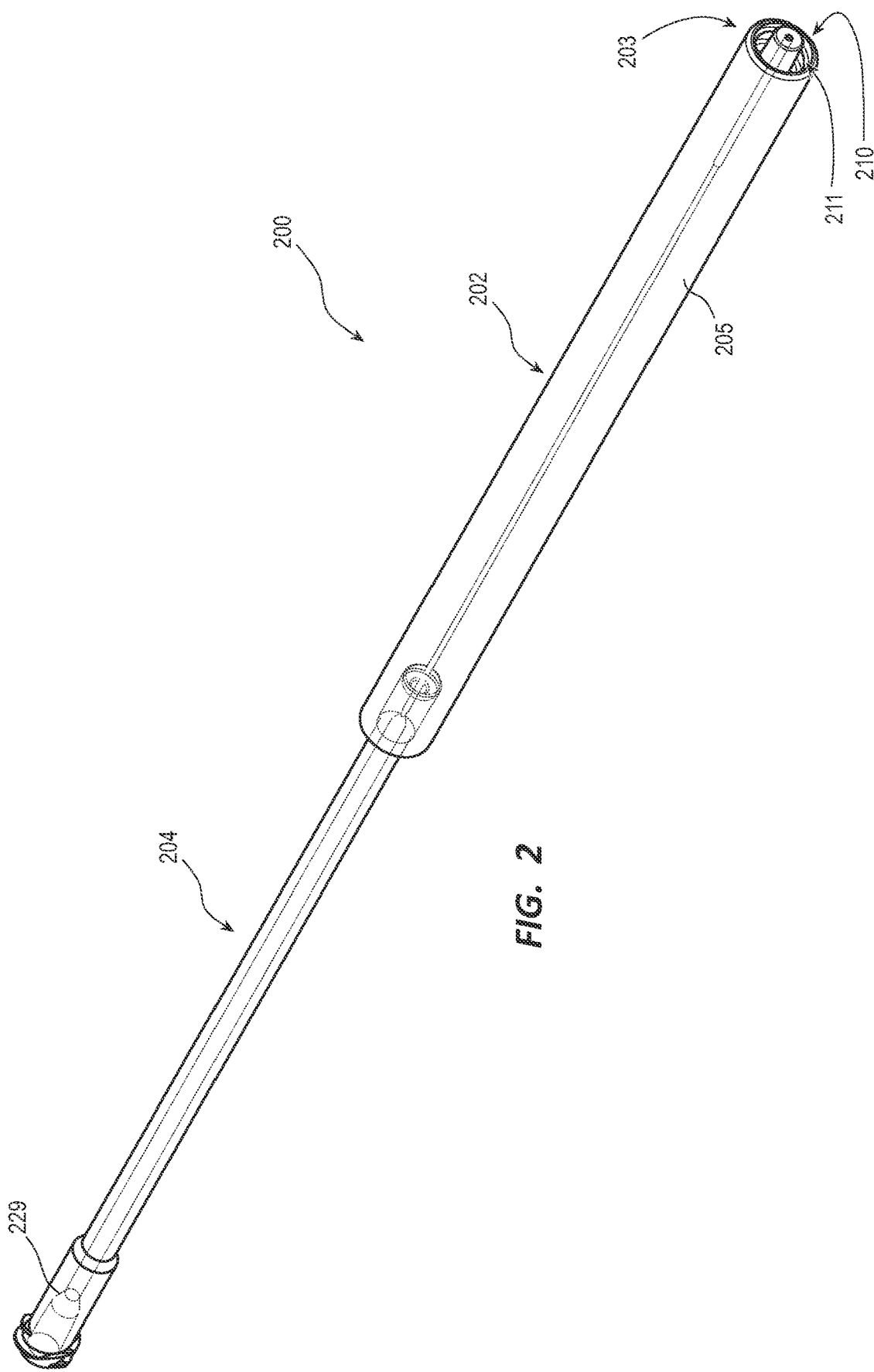
FIG. 2 is a perspective view of an embodiment of an access system configured to be coupled with an embodiment of a base catheter system, the access system being shown in an undeployed or retracted state.

FIGS. 1A and 1B depict an embodiment of a base catheter system 100, such as, for example, a peripheral intravenous (PIV) catheter system. The base catheter system 100 may also be referred to herein as a placed catheter system, a preplaced catheter system, an anchor catheter system, etc. The base catheter system 100 includes a catheter tube 104 and a catheter hub 106 that is fixedly secured to a proximal end of the catheter tube 104. The base catheter system 100 can be inserted into a patient P in any suitable manner such that at least a distal end of the catheter tube 104 extends into a vessel V (e.g., a vein) of the patient (FIG. 1B) and such that a proximal portion of the base catheter system 100, including the catheter hub 106, is accessible at an exterior of the patient. The catheter tube 104 can define a lumen 108 through which, for example, infusions may be delivered into the vessel V. The catheter hub 106 may be of any suitable variety. In some embodiments, the catheter hub 106 is a female luer connector.

While not shown in FIG. 1A, in many embodiments, the proximal portion of the base catheter system 100 that remains at an exterior of the patient P after placement of the catheter tube 104 can be secured to the skin of the patient. A variety of dressing options are possible, including tape or adhesive dressings that are specifically designed for such securement. As further discussed below, certain embodiments may be usable with the base catheter system 100 when the base catheter system 100 has been secured to the patient using a tape or adhesive dressings (e.g., a standard or known dressing), and, in further instances, may be usable with the base catheter system 100 without the use of any specialized apparatus (e.g., a wedge-shaped support member) that might couple with the base catheter system 100 to position the catheter hub 106 and the proximal end of the tube 104 at an angle relative to the surface of the skin, such as, e.g., at an acute angle similar to that shown in FIG. 1A.

In some embodiments, the base catheter system 100 can be an open catheter system, such as an open intravenous catheter system (e.g., an open PIV catheter system). The term "open" in this context is used in its ordinary sense in the relevant art, and includes catheter systems in which the connector 106 may not provide a barrier (e.g., a fluid-tight seal) between the lumen 108 and the environment external to the catheter hub 106. For example, in the illustrated embodiment, the catheter hub 106 defines an open proximal end that is exposed to the environment. In some embodiments, a sealing member, such as any suitable valve, septum, or needleless connector, may be affixed to the catheter hub 106. In other or further embodiments, an extension set (see, e.g., FIGS. 24 and 25) may be coupled with the catheter hub 106. In certain embodiments (such as that depicted in FIG. 24) the extension set can include a connector at a proximal end thereof, a connector at a distal end thereof for coupling with the catheter hub 106, and a sideport therebetween with an extension tube and any suitable connector at a proximal end of the extension tube. In some instances, the proximal connector may include or be coupled with a valve, septum, or needleless connector.

As further discussed below, in other embodiments, the base catheter system 100 may instead be a "closed" catheter system, such as a closed intravenous catheter system (e.g., a closed PIV catheter system). An illustrative example of such a closed intravenous catheter system is depicted in, and discussed further below, with respect to FIGS. 12-14. The term "closed" in this context is used in its ordinary sense in the relevant art, and includes systems in which the catheter tube 104 is attached to a distal port of a catheter hub 106 that further includes a proximal port, from which an introducer needle can be withdrawn and thereupon sealed or plugged, and an integrated side port in fluid communication with the catheter tube 104, via which fluid delivery and/or removal via the catheter tube 104 is achieved. One illustrative example of a closed PIV catheter system is the NEXIVA™ closed IV catheter system, available from Becton Dickinson.

With reference to FIGS. 2-5, in some embodiments, an access system 200 can be configured to couple with the base catheter system 100. The access system 200 may also or alternatively be referred to as an access assembly. The illustrated access system 200 may be particularly well suited for coupling with and/or for operative use in advancing a conduit into an open base catheter system 100, such as the illustrative system 100 depicted in FIGS. 1 and 2. In other or further instances, the access system 200 can be configured to couple with an extension set (e.g., such as that depicted in FIG. 24) of an open base catheter system 100, and can advance a conduit through the extension set and ultimately into the catheter tube 104. The access system 200 can also be referred to as a fluid channeling system, a fluid extraction system, a blood removal system, a follow-on cannula system, a secondary catheter system, a supplemental catheter system, etc.

The base catheter system 100, such as the catheter tube 104 thereof, can be inserted into a vessel of a patient in any suitable manner, including those known in the art. In some instances, no portion of the access system 200 is coupled with the base catheter system 100 prior to insertion of the base catheter system 100 into the patient. For example, the access system 200 may be coupled with the base catheter system 100 after the base catheter system 100 has been placed within the patient. In particular, one or more portions of the access system 200 may be coupled to the base catheter system 100 at any suitable time after placement of the base catheter system 100. In some instances, the suitable time may be no less than 30 minutes, 1 hour, 6 hours, 12 hours, 18 hours, 1 day, 2 days, or 3 days after initial placement of the base catheter system 100.

The access system 200 includes a connector 202 and a cannula 204. The cannula 204 may also be referred to as a conduit. The cannula 204 can define a continuous fluid path through which blood can be extracted from the vasculature of a patient. The cannula 204 is configured to move relative to the connector 202 between a retracted or undeployed state (FIGS. 2 and 3) and an advanced or deployed state (FIGS. 4 and 5). In particular, a user can grip the cannula 204—e.g., a proximal end of the cannula 204—to distally advance (e.g., translate forwardly) the cannula 204 relative to the connector 202 from the retracted state to the advanced state. Likewise, the user can grip the cannula 204—e.g., the proximal end of the cannula 204—to retract proximally (e.g., translate rearwardly) the cannula 204 relative to the connector 202 from the advanced state back to the retracted state. For example, in some instances, the user can grip a connector 229 at a proximal end of the cannula 204 to advance and/or retract the cannula 204.

The connector 202 can include a coupling interface 210, which can be at a distal end of the connector 202. In the illustrated embodiment, the coupling interface 210 includes a threaded male luer interface 211, such as may readily couple with a female luer interface of the catheter hub 106 described above. Any other suitable coupling interface 210 is contemplated.

The connector 202 may be longitudinally elongated so as to be substantially tubular in shape. For example, in some embodiments, a distal end of the connector 202 may include a connection region 203 at a distal end thereof that defines the coupling interface 210, and can further include a housing, barrel, tube, or sheath 205 that extends proximally from the connection region 203. The sheath 205 can define an extended channel 212 (FIG. 5), which may also be referred to as an inner chamber, cavity, or interior space, within which a portion of the cannula 204 may be positioned. For example, in various embodiments, at least some portion of the cannula 204 may be positioned within or internal to the sheath 205 when the cannula 204 is in the retracted state, the deployed state, and throughout transitioning between the retracted and deployed states.

Figure 6:
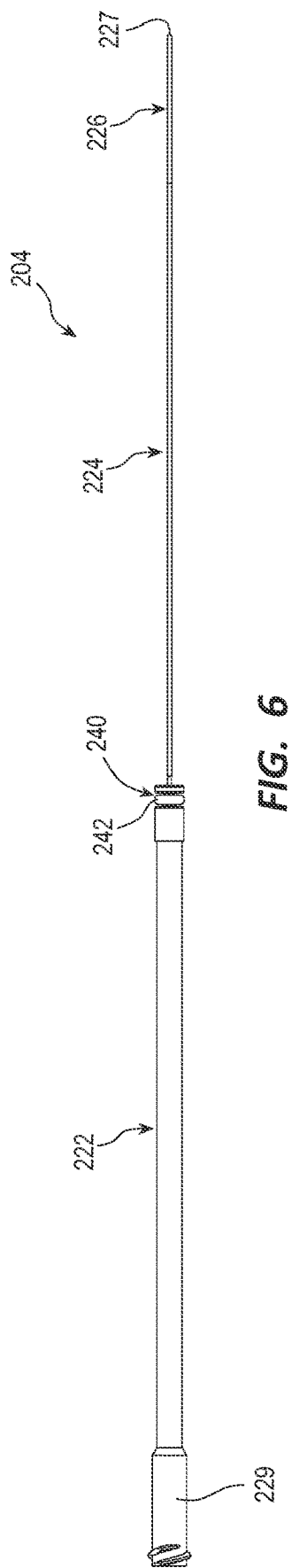
FIG. 6 is a side elevation view of an embodiment of a cannula compatible with the access system of FIG. 2.

With reference to FIGS. 5 and 6, in various embodiments, the cannula 204 can be a multi-part or multi-segment component. For example, in the illustrated embodiment, the cannula 204 is a three-segment element that defines a continuous or uninterrupted flow path or fluid path 220 for blood draws. In the illustrated embodiment, each segment is defined by a separate piece, with each piece being formed of one or more materials that are different from materials of one or more of the other two pieces. In other embodiments, two or more of the multiple segments (e.g., the proximal and medial segments) may be integrally formed of a unitary piece of material. In still other or further embodiments, each segment may include one or multiple components or constituent elements. In certain of these embodiments, either two or all three of the segments may have at least one component that differs in some manner from each of the remaining segments, such as, for example, by way of physical property, number, presence or absence, etc. The fluid path 220 can include a lumen 221. In some embodiments, the lumen 221 can vary in diameter along a length of the cannula 204. For example, in the illustrated embodiment, the lumen 221 defines a larger inner diameter in a proximal region of the cannula 204, as compared to a distal region thereof. In other embodiments, the lumen 221 may define a substantially constant inner diameter along substantially a full length of the cannula 204.

In some embodiments, the cannula 204 can include a proximal segment 222, a middle, intermediate, or medial segment 224, and a distal segment 226, as identified in FIG. 6. In some embodiments, the materials and/or material properties of at least one of the segments can vary relative to that or those of one or more of the remaining segments.

In certain embodiments, the proximal segment 222 can be rigid or semi-rigid. The proximal segment 222 can be formed of a clear plastic, for example, which can allow for visualization of fluid flow. Rigidity of the proximal segment 222 can allow for the cannula 204 to be pushed distally relative to the connector 202. In some embodiments, the proximal segment 222 can include the connector 229 at the proximal end thereof. The connector 229 can be of any suitable variety. For example, in the illustrated embodiment, the proximal segment 222 includes a connector 229 that is a female luer connector (i.e., compliant with ISO standards), which can be connected to any suitable any suitable fluid source and/or fluid collection device. For example, the connector 229 can be configured to couple with a syringe, which may be used for infusion or blood collection. The connector 229 may be used for connection to blood draw apparatus, such as syringes or evacuated blood collection tubes (e.g., Vacutainer® tubes available from Becton Dickinson) and/or apparatus therefor. For example, in some embodiments, the connector 229 may include or may be configured to connect with a Vacutainer® one-use holder, via which blood draws may be made into one or more Vacutainer® tubes. In other embodiments, the connector 229 may be integrally formed with a fluid source and/or a fluid collection apparatus.

In some embodiments, a valve or vent fitting may be removably attached to or incorporated into the proximal segment 222. A vent fitting (such as, e.g., the vent fitting 819 depicted in FIG. 12) can, for example, permit blood flow from the vasculature through the cannula 204 as air within the cannula lumen 221 is vented to the environment, and the vent fitting can serve as a liquid-impervious barrier to the blood. In some embodiments, the proximal segment 222 can allow visualization of an initial passage of blood through the lumen 221, or stated otherwise, can provide blood flashback visualization. For example, when the proximal segment 222 includes a tube of clear or translucent material, the proximal segment 222 can allow for potential visualization of blood flashback. In various embodiments, the proximal segment 222 can include or be formed of a tube of polycarbonate, polyurethane, and/or polypropylene. Any other or further suitable material is contemplated.

In some embodiments, the proximal segment 222 may be flexible in transverse directions, relative to a longitudinal axis of the proximal segment 222, yet may have sufficient rigidity in a longitudinal direction to transfer distal forces along the cannula 204. For example, in some embodiments, the proximal segment 222 may be sufficiently flexible to bend up to about 90, 120, 150, or 180 degrees, e.g., without plastically deforming, yet can be straightened and advanced distally to advance the cannula 204 distally relative to the connector 202. In some instances, the proximal segment 222 can be packaged in a bent state, which can permit reduction of a total length of packaging for a prepackaged access system 200. A user can remove the access system 200 from the packaging and either manually unbend the proximal segment 222 or permit the proximal segment 222 to resiliently straighten to a relaxed state, which may be substantially rectilinear. Stated otherwise, in some embodiments, the proximal segment 222 may be resiliently deformable and may naturally unbend to a substantially straight configuration upon removal from the packaging. The user can advance the straightened proximal segment 222 through the proximal end of the sheath 203 to advance the cannula 204 distally relative to the connector 202.

In other embodiments, the proximal segment 222 may be relatively rigid. The proximal segment 222 may have a rectilinear configuration, such as depicted in FIG. 6, and may be relatively resistant to lateral deformation from the rectilinear shape. For example, the proximal segment 222 may be preformed, packaged, and usable in the rectilinear shape, and in further embodiments, may be substantially resistant to deformations from the rectilinear shape.

In certain embodiments, the medial segment 224 of the cannula 204 can be stiff or rigid so as to avoid bending or kinking. The medial segment 224 can transfer distal forces from the proximal segment 222 to the distal segment 226. In various embodiments, the medial segment 224 may include or be formed of metal, such as, for example, stainless steel. For example, in some embodiments, the medial segment 224 consists substantially of a metallic tube, such as a hypotube, that is coupled to the distal segment 226. In other embodiments, the medial segment includes a metallic tube, such as a hypotube, that encompasses a portion of a polymeric tube that extends through a lumen of the metallic tube. Other or further suitable materials and/or configurations are also contemplated.

The proximal segment 222 and the medial segment 224 may be joined together in any suitable manner. For example, in various embodiments, the proximal segment 222 may be overmolded over a proximal end of the medial segment 224. In other embodiments, the proximal and medial segments 222, 224 may be press-fit, friction-fit, adhered, or otherwise joined together, and may be fluidically sealed such that no leakage from the lumen 221 occurs at the interface between these two segments.

The distal segment 226 may be relatively soft or flexible so as to readily advance through the preplaced catheter 104. For example, the distal segment 226 can be substantially softer and/or more flexible (e.g., can be laterally deflected much easier) than the medial segment 224. For example, the distal segment 226 may be sufficiently soft or flexible to prevent or inhibit damage to the catheter tube 104 and/or, in certain embodiments, the blood vessel V (e.g., should the distal segment 226 be extended past the distal end of the catheter tube 104 and come into contact with the blood vessel V). Nevertheless, in various embodiments, the distal segment 226 may be sufficiently rigid to be advanced through the catheter tube 104. In some embodiments, the distal segment 226 may render the catheter tube 104 straighter as the distal segment 226 is advanced therethrough.

In some embodiments, a distal tip 227 of the distal segment 226 includes one or more features that render the distal tip 227 atraumatic, or substantially atraumatic, relative to one or more of the preplaced catheter tube 104 and the patient vasculature. For example, in some embodiments, the distal segment 226 comprises a tube of polymeric material (e.g., polyimide). In some embodiments, the distal tip 227 of the tube is laser ablated so as to smooth and round the tip, thus rendering the distal tip 227 less prone to scraping, scratching, cutting, and/or puncturing an inner surface of the catheter tube 104 and/or a vessel within which the catheter tube 104 is positioned when the distal tip 227 extends from the catheter tube 104. In other or further embodiments, the distal tip 227 can include a softer material attached to a distal end of the polymeric tube (e.g., a material with a lower durometer). For example, in some embodiments, a silicone layer may be positioned at the distal tip 227 in any suitable manner.

The distal segment 226 may be fully positioned within the catheter tube 104 when the cannula 204 is in the advanced state, such that the distal tip 227 is proximally recessed or generally flush with a distal tip of the catheter tube 104, or the distal segment 226 may extend slightly beyond the distal tip of the catheter tube 104, during a blood draw. The distal segment 226 can conform to a tortuous path of the vasculature and/or defined by the preplaced catheter system 100 when a portion of the catheter system 100 (i.e., at least a portion of the catheter tube 104) is positioned within the vasculature. The distal segment 226 can prevent damage to the catheter tube 104, e.g., during advancement therethrough. For example, if the catheter tube 104 is sharply bent or kinked, the distal segment 226 can avoid puncturing through or scraping an interior of the catheter tube 104 at the bent or kinked site during distal advancement of the distal segment 226 through the catheter tube 104.

In various embodiments, the distal segment 226 can include or be formed of polyimide, polyether block amide, silicone, polyamide, nylon, PEEK, and/or polyurethane. In other or further embodiments, the distal segment can comprise a siliconized polyurethane, such as one or more of the materials described in U.S. Patent Application Publication No. 2019/0153147 to Muse et al., the entire contents of which are hereby incorporated by reference herein. Any other or further suitable material is also contemplated.

In some embodiments, the distal segment 226 can have sufficient rigidity to at least partially straighten out the catheter tube 104 of the system 100 as the distal segment 226 is advanced through the catheter tube 104. For example, in some embodiments, the distal segment 226 can have a stiffness that is greater than the stiffness of the catheter tube 104. Straightening via the distal segment may, in some instances, facilitate blood withdrawal and/or permit laminar or substantially laminar blood flow through the cannula 204. Stated otherwise, the distal segment 226 can provide a straight or straightened flow path, relative to a flow path that is defined by the preplaced catheter system 100 prior to use of the system 200. For example, in some instances, the fluid path 220 through the deployed system 200 can be substantially straight or rectilinear, or can be gently sloped or gradually bent (e.g., without sharp turns or kinking) along the length of at least the distal segment 226 when the system 200 is deployed within the preplaced catheter system 100. The distal segment 226, or at least a distal portion thereof, can be sized to slide or otherwise be advanced through the lumen 108 of the catheter tube 104.

In other embodiments, the distal segment 226 may be relatively softer than embodiments that might achieve significant straightening of a pre-placed catheter tube. In various embodiments, the distal segment may achieve a lower amount, a minimal amount, or even substantially no straightening of the preplaced catheter tube 104. A relatively softer distal segment 226 may nevertheless be able to follow a tortuous path through the catheter system 100 while maintaining patency of the lumen 221 therethrough. In some embodiments, lateral support provided to the distal segment 226 by a reinforcement member included in the connector 202 and/or strength and kink-resistance afforded by the medial segment 224 can assist in advancing the distal segment 226 into the catheter tube 104, as further discussed below.

The distal segment 226 may be joined with the medial segment 224 in any suitable manner. For example, in some embodiments, the medial segment 224 and the distal segment 226 are attached via a length of thin-walled heat shrink tubing (see, e.g., FIGS. 21 and 22). Such an attachment mechanism may be particularly useful, e.g., when the medial segment 224 includes a metal (e.g., stainless steel) tube and the distal segment 226 includes a polymeric tube that abuts the metal tube. Any other or further suitable attachment is contemplated.

In some embodiments, only the distal segment 226 is introduced into and passes through the preplaced catheter tube 104. Stated otherwise, when the access system 200 is in a fully deployed state, the distal end of the medial segment 224 remains proximal to the proximal end of the catheter tube 104, and at least a portion of the distal segment 226 extends into and/or through catheter tube 104. As previously stated, in at least some embodiments, a distal end of the distal segment 226 can extend distally past a distal tip of the catheter tube 104 when the access system 200 is in the fully deployed state.

In other embodiments, the distal segment 226 may be relatively shorter and may function as a substantially atraumatic tip for the medial segment 224, and at least a portion of the medial segment 224 may be introduced into the catheter tube 104. In some embodiments, the medial segment 224 can provide a straightened path through at least a proximal portion of the catheter tube 104. For example, the distal segment 226 can include any of the tip features previously discussed and may aid in preventing trauma to the catheter and the blood vessel, and the medial segment 224 can straighten out at least a portion of the catheter tube 104 of the system 100 as the medial segment 224 is advanced through this at least a portion of the catheter tube 104. This straightening may facilitate blood withdrawal and/or achieve laminar or substantially laminar blood flow through the cannula 204. Stated otherwise, in various embodiments, the medial segment 224, whether alone or in combination with the distal segment 226, can provide a straight or straightened flow path, relative to a flow path that is defined by the preplaced catheter system 100 prior to use of the system 200. For example, the fluid path 220 through the deployed system 200 can be substantially straight or rectilinear, or can be gently sloped or gradually bent (e.g., without sharp turns or kinking) along the length of at least the medial segment 224 when the system 200 is deployed within the preplaced catheter system 100. The medial segment 224, or at least a distal portion thereof, can be sized to slide or otherwise be advanced through at least a portion of the lumen 108 of the catheter tube 104.

In other embodiments, as further discussed below, the medial segment 224 may not extend into the catheter tube 104. For example, in some embodiments, an outer diameter of the medial segment 224 is larger than an inner diameter of the catheter tube 104 and may be prevented from entering the proximal end of the catheter tube 104.

Figure 7:
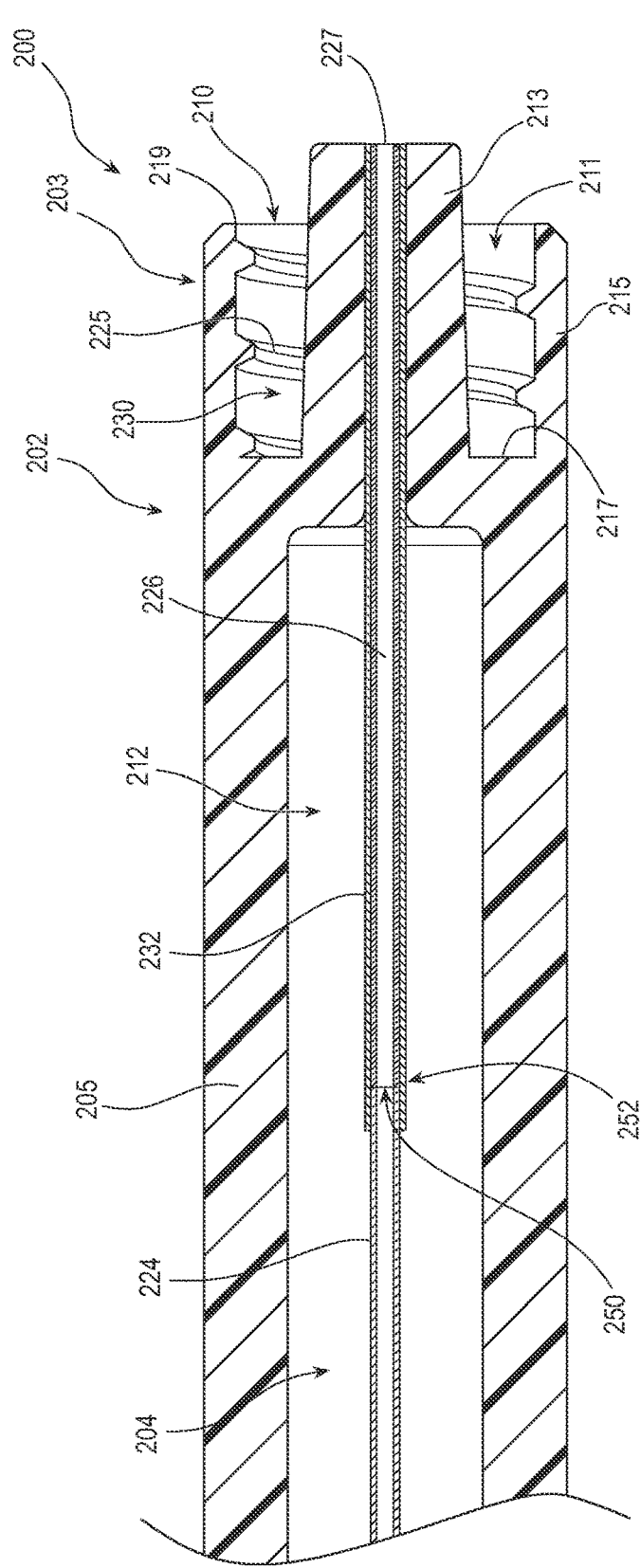
FIG. 7 is a side elevation view of a distal portion of the access system of FIG. 2 in the undeployed or retracted state.

With reference to FIG. 7, in some embodiments, the connector 202 includes a reinforcing member 230, which may also or alternatively be referred to herein as a reinforcement member. In the illustrated embodiment, the reinforcing member 230 comprises a tubular member, such as a needle-like element or reinforcing cannula 232. The reinforcing cannula 232 may also or alternatively be referred to herein as a reinforcing tube. In some embodiments, the reinforcing cannula 232 may be formed from a metallic hypotube. The reinforcing member 230 can provide external or lateral support to the distal segment 226 to prevent buckling and/or kinking of the distal segment 226 during forward advancement of the cannula 204. For example, in various embodiments, the distal tip 227 of the distal segment 226 can encounter resistive forces as the distal segment 226 is advanced distally into the catheter tube 104. In particular, during such distal advancement, distally directed forces can be provided to a proximal end of the distal segment 226 by the relatively stiffer or reinforced (e.g., axially or longitudinally strengthened) medial segment 224, and the forces that are resistive to distal advancement of the distal segment 226 can tend to act in generally the opposite direction (e.g., generally proximally) at the distal end of the distal segment 226. These generally oppositely directed forces can tend to compress the distal segment 226, causing the distal segment 226 to buckle, bow, bend, kink, or displace laterally. The reinforcing member 230 can counter these lateral forces, thereby preventing buckling or kinking and facilitating insertion of the distal segment 226 into and through the catheter tube 104.

The inner diameter of the reinforcing cannula 232 can be such that the outer diameter of each of the distal segment 226 and at least a distal portion of the medial segment 224 can fit therein. The fit may desirably be relatively close, such that there is minimal clearance between the inner surface of the reinforcing member 230 and the outer surface of each of the distal and medial segments 226, 224. In various embodiments, an inner diameter (e.g., a maximum transverse dimension of an inner perimeter, circumference, and/or profile) of the reinforcement member 230 may be larger than an outer diameter (e.g., a maximum transverse dimension of an outer perimeter, circumference, and/or profile) of at least one of the distal and medial segments 226, 224 by no more than 5, 10, 15, 20, 25, or 30 percent. In certain embodiments, the cannula 204 can be said to slide through the reinforcing cannula 232 during advancement and withdrawal (e.g., transitions between the retracted and advanced states).

In the illustrated embodiment, the reinforcing cannula 232 fully covers or encompasses the distal segment 226 in the fully retracted state, which may also be referred to as the set, ready, initial, pre-deployed, or proximal state, position, orientation, or configuration. The deployed state may also or alternatively be referred to as an advanced, active, or distal state, position, orientation, or configuration. In some embodiments, a proximal tip of the distal segment 226 and a distal tip of the medial segment 224 may be positioned within the reinforcing cannula 232 when in the retracted state, as shown.

Stated otherwise, in some embodiments, the medial segment 224 can terminate at a distal terminus 250, which may correspond with the distalmost tip of the medial segment 224. In the illustrated embodiment, the medial segment 224 includes a tubular member having a substantially flat or planar transversely oriented face at the distal terminus 250. This transverse face abuts a substantially flat or planer transversely oriented face at a proximal tip of a tubular member of the distal segment 226. As previously discussed, in some embodiments, a heat shrink tube can extend over these abutting surfaces, which can join or assist in joining the medial and distal tubular members to each other. Stated otherwise, in some embodiments, the medial and distal segments 224, 226 are joined at an interface 252, which in the illustrated embodiment, includes abutting surfaces of medial and distal tubes or tubular members. The heat-shrink tubing (see, e.g., feature 1080 in FIGS. 21 and 22) can extend over these abutting surfaces at the interface 252, or stated otherwise, can extend over the interface 252.

With continued reference to FIG. 7, when the cannula 204 is in the retracted, initial, or set position, the distal terminus 250 and/or the interface 252 can be positioned within the reinforcement member 230. This can ensure that the full length of the distal segment 226 is reinforced when the distal tip 227 begins to encounter resistance to distal advancement of the cannula 204. For example, as shown in FIG. 7, in the illustrated embodiment, the distal tip 227 of the distal segment 226 of the cannula 204 is substantially flush with or slightly recessed relative to a distal tip of the reinforcing tube 232 when the cannula 204 is in the retracted position, and a proximal tip of the distal segment 226 is at the interface 252, which is likewise positioned within the reinforcing tube 232. Accordingly, as soon as the cannula 204 begins to advance distally, the distal tip 227 of the cannula 204 advances distally past the distal tip of the reinforcing tube 232 and may, in some instances, be susceptible to encountering resistive forces, such as by coming into contact with a portion of the pre-placed catheter tube 104 that is kinked, bent, curved, or otherwise poses resistance to passage therethrough. In such instances, by positioning the distal terminus 250 of the medial segment 224, or stated otherwise, by positioning the interface 252 of the medial and distal segments 224, 226, within the reinforcement member 230, when the cannula 204 is in the fully retracted position, it can be ensured that the proximal end of the distal segment 226 is laterally supported by the reinforcement member 230 as soon as the distal tip 227 is exposed. Likewise, a full length of whatever portion of the distal segment 226 that remains within the reinforcement member 230 can be reinforced as the distal segment 226 is advanced distally out of the reinforcement member 230. In certain embodiments, to achieve lateral support of the distal segment 226 as just described, a length of the reinforcement member 230, and/or a length of the distal segment 226 that is positioned within the reinforcement member 230 when in the set position, can be greater than a distance between a distal tip of the reinforcement member 230 at a position at which the distal segment 226 initially encounters forces resistive to distal advancement as the distal segment 226 is deployed from the set position.

In other embodiments, the distal tip 227 of the distal segment 226 may be proximally recessed within the reinforcement member 230 by a more significant distance (e.g., by a length that is approximately equal to, or that is on the order of two, three, four or more times greater than, an outer diameter of the distal segment 226) when the cannula 204 is in the fully retracted position. In some embodiments, the interface 252 may be positioned proximal to a proximal end of the reinforcement member 230 when the cannula 204 is in the fully retracted position, whereas in other embodiments, the interface 252 may be positioned within the reinforcement member 230 when the cannula 204 is in the fully retracted position. In either case, in various embodiments, the interface 252 may desirably be positioned within the reinforcement member 230 when the distal tip 227 is first positioned distal of and external to the reinforcement member 230. For example, when the cannula 204 is in the fully retracted position, the interface 252 may be positioned proximal to a proximal tip of the reinforcement member 230 by a distance that is less than or equal to a distance by which the distal tip 227 is recessed relative to a distal tip of the reinforcement member 230. Thus, as the cannula 204 is advanced distally, the interface 252 may enter into the proximal end of the reinforcement member 230 at the same time as or earlier than the distal tip 227 exits distally out of the distal end of the reinforcement member 230.

In certain embodiments, the medial segment 224 is sufficiently rigid to independently avoid buckling and/or kinking as the distal segment 226 is advanced through the reinforcing cannula 232 and into and through the preplaced catheter tube 104. For example, an unsupported length of the medial segment 224, relative to the reinforcing cannula 232 (e.g., a portion of the medial segment 224 that is external to the reinforcing cannula 232) can be self-supporting, intrinsically supported, or otherwise sufficiently rigid avoid buckling and/or kinking that might otherwise occur if the medial segment 224 were instead formed solely of the same material and geometric configuration as the distal segment 226— e.g., if the medial and distal segments 224, 226 were formed of a continuous tube of a single material of uniform construction (e.g., uniform hardness, thickness, and diameter) and the medial segment 224 were not reinforced, or stated otherwise, if the medial segment 224 consisted solely of a continuous extension of the soft and/or flexible distal segment 226. Whereas the medial segment 224 may be "unsupported," such as by not having a reinforcing or support structure that is external thereto, the medial segment 224 may nevertheless be self-supported. For example, a portion of the medial segment 224 positioned proximal to the reinforcing member 230 may not be reinforced or supported by the reinforcing member 230, but may nevertheless be intrinsically supported, e.g., due to its intrinsic rigidity.

For example, in order to transition the cannula 204 from the retracted position to the advanced or deployed position, distally directed forces are applied to the proximal segment 222 of the cannula 204, or stated more generally, are applied to the proximal end of the cannula 204. These distally directed forces tend to urge the medial segment 224 and the distal segment 226 distally. When the distal segment 226 encounters resistive forces to its distal advancement, these resistive or opposing forces are transferred proximally through the cannula 204. Accordingly, during such advancement and resistance events, the medial segment 224 encounters opposing forces at its proximal and distal ends. These opposing or compressive forces could tend to bend, kink, or otherwise laterally deflect, e.g., intermediate regions of the medial segment 224 that are external to and unsupported by the reinforcement member 230. However, the medial segment 224 can be configured to withstand deflection from the opposing or compressive forces. For example, as previously discussed, in some embodiments, the medial segment 224 is formed of a rigid material, such as stainless steel, that has sufficient intrinsic strength to resist the compressive forces without bending (or by bending by insignificant amounts) and/or without buckling or kinking. Stated otherwise, the medial segment 224 may be self-reinforced, internally reinforced, or intrinsically reinforced, such that a full length of the medial segment 224, whether positioned within or without the reinforcement member 230, may be said to be reinforced.

In other or further embodiments, the medial segment 224 may include a separate reinforcement or support component, such as a support tube, as discussed further below (see, e.g., FIGS. 56A, 56B, and 59 and accompanying text). For example, in some embodiments, the distal and medial segments 226, 224 may include a continuous polymeric tube of uniform properties and dimensions that spans a full length of each of the distal and medial segments 226, 224. The medial segment 224 can additionally include a reinforcement or support tube that encompasses the polymeric tube. The support tube may have an inner surface that is only slightly larger than, is marginally larger than, and/or that closely conforms to an outer surface of the polymeric tube. For example, in various embodiments, an inner diameter (e.g., a maximum transverse dimension of an inner perimeter, circumference, and/or profile) of the support tube may be larger than an outer diameter (e.g., a maximum transverse dimension of an outer perimeter, circumference, and/or profile) of the inner polymeric tube by no more than 5, 10, 15, 20, 25, or 30 percent. As further discussed below, the support tube may be fixedly secured to and/or relative to the polymeric tube.

The support tube can have a distal end positioned within the reinforcement member 230 when the cannula 204 is in the retracted state. The support tube can slide within the reinforcement member 230 as the cannula 204 is advanced distally. As compressive forces arise at opposite ends of the inner polymeric tube during distal advancement thereof, the support tube can generally maintain a rectilinear profile of the portion of the polymeric tube that is positioned therein. Stated otherwise, the relatively stiffer support tube can resist deflection, bending, buckling, or kinking of the inner polymeric tube. As with embodiments discussed in the previous paragraph, the medial segment 224 can be said to withstand deflection from the opposing or compressive forces. For example, the support tube can be formed of a rigid material, such as stainless steel, that has sufficient strength to counter deflection of the inner polymeric tube as it encounters compressive forces that would tend to cause the polymeric tube to deflect, bend, buckle, or kink. The support tube can thereby prevent bending (or permit bending by insignificant amounts) buckling or kinking of the inner polymeric tube. Stated otherwise, the medial segment 224 may be self-reinforced or intrinsically reinforced, such that a full length of the medial segment 224, whether positioned within or without the reinforcement member 230, may be said to be reinforced.

In view of the foregoing discussion, at least a portion of the distal segment 226 can be reinforced when the cannula 204 is in the retracted state or set position, which reinforcement can be provided by the reinforcement member 230 of the connector 202. Further, at least a portion of the medial segment 224 can be reinforced when the cannula 204 is in the retracted state or set position, which reinforcement can be provided intrinsically, such as by a tube of relatively stiff or rigid material that unitarily constitutes the medial segment 224 or such as by a tube of relatively stiff or rigid material that supports a length of a polymeric tube that is positioned within the relatively stiff tube in the region of the medial segment 224. In further instances, at least a distal end of the medial segment 224 may be reinforced externally by the reinforcement member 230 when the cannula 204 is in the retraced state. Thus, more generally, a length of the cannula 204 that is positioned within the connector 202, such as within the connection region 203 and the sheath 205, can be reinforced. In various embodiments, a reinforced length of the cannula 204, when in the retracted state, can be no less than 50, 60, 70, 80, or 90 percent of a total length of the connector 202. In other or further embodiments, a reinforced length of the cannula 204, when in the retracted state, can be no less than 50, 60, 70, 80, or 90 percent of a total length of the sheath 205. In still other or further embodiments, a reinforced length of the cannula 204, when in the retracted state, can be no less than 50, 60, 70, 80, or 90 percent of a length of the internal cavity 212 of the sheath 205. In still other or further embodiments, a reinforced length of the cannula 204, when in the retracted state, can be no less than 50, 60, 70, 80, or 90 percent of a distance between a proximal end of the reinforcement member 230 and a proximal end of the internal cavity 212 of the sheath 205.

Moreover, in view of the foregoing discussion, a substantial length of the cannula 204 can be reinforced throughout movement of the cannula 204 from the retracted position to the fully deployed position. The reinforced length may vary throughout at least a portion of the deployment event, such as when increasing amounts of the distal segment 226 exit from the distal end of the reinforcement member 230. In various embodiments, a reinforced length of the cannula 204 varies throughout at least a portion of a deployment event in which the cannula 204 is moved from the retracted state to the fully deployed state, and a minimum reinforced length of the cannula 204 throughout a full deployment event can be no less than 20, 25, 30, 35, 40, 45, 50, 55, 60, 65, 70, or 75 percent of a total length of the cannula 204. The total length of the cannula 204 can be defined, for example, as a distance between the distal tip 227 of the cannula 204 and the proximal tip of the connector 229 (see FIG. 6). In many embodiments, the minimum reinforced length may be achieved when the cannula 204 is in the fully deployed state.

With continued reference to FIG. 7, the reinforcing cannula 232 may be formed of any suitable material. For example, the reinforcing cannula 232 can include or be formed of stainless steel and/or rigid plastic. In some embodiments, the reinforcing cannula 232 can be formed of a metallic hypotube. The reinforcing cannula 232 may be attached to the connector 202 in any suitable manner, such as, for example, via press-fit, bonding, or overmolding. For example, in the illustrated embodiment, the connector 230 comprises a polymeric material that is overmolded onto the reinforcing cannula 232.

In other embodiments, the reinforcing cannula 232 is omitted. For example, the reinforcing member 230 may instead be formed as a channel or lumen that extends through, e.g., a distal end of the connector 202. In some embodiments, the distal end of the connector 202 may be molded or otherwise formed with additional material (e.g., polymeric material), as compared with what is shown in FIG. 7, through which the channel or lumen that forms the reinforcing member 230 extends. For example, in some embodiments, at least a portion of the distal end of the connector 202, which includes the connection interface 210, may be extended longitudinally in the proximal direction to define an elongated reinforcing member 230. This alternative reinforcing member may, for example, have the same length as that of the reinforcing tube 232 depicted in FIG. 7, but may instead be formed from additional polymeric material with a lumen extending therethrough.

With reference again to FIGS. 5 and 6, in some embodiments, the system 200 can include a friction or resistance element 240, which can resist, regulate, temper, adjust, or otherwise passively respond to relative movement of the connector 202 and the cannula 204. In the illustrated embodiment, the resistance element 240 comprises an O-ring 242 that is received within an annular channel 244 defined by the proximal segment 222. The O-ring 242 can slide along an inner surface of the connector 202. Any other suitable resistance mechanism is contemplated, such as a saw tooth, ratchet, or other interface between the proximal segment 222 and the connector 202. In other or further embodiments, the resistance element 240 can include friction grease in addition to or instead of other resistance elements that regulate relative movement of the connector 202 and the cannula 204.

As previously discussed, in various embodiments, the connector 202 can be configured to couple with an open catheter system and/or a closed catheter system. In some embodiments, the connector 202 may be attached directly to a catheter hub of an open catheter system, while in other embodiments, the open catheter system can include an extension set attached to the catheter hub, and the connector 202 can be attached to a port of the extension set.

With reference again to FIG. 7, in some embodiments, the reinforcement member 230 includes a protrusion or projection 213 that extends distally from a surface 217 (e.g., a distally facing surface) of the connector 202. The surface 217 may also be referred to as a bottom surface or as a recessed, inner, or internal surface of the connection region 203 of the connector 202. The inner and internal surface descriptors arise from the recessed relationship of the surface 217 relative to adjacent portions of the connector 202, such as relative to a threaded skirt 215 and a central male luer, although the surface 217 is an overall exterior of the connector 202. In the illustrated embodiment, the projection 213 includes the central male luer, which is formed of polymeric material, and within which a distal portion of the reinforcing tube 232 is positioned. Stated otherwise, the projection 213 includes a distal end of the reinforcing tube 232 encompassed by other material (e.g., polymeric material) that projects distally from the recessed surface 217. In some embodiments, the projection 213 can be coupled directly with an open hub (e.g., the catheter hub 106 in FIG. 1), such as to engage the hub in a fluid-tight seal (e.g., via luer interfaces). The projection 213 can be configured to open or otherwise defeat a valve, septum, or the like of a hub or of an extension set coupled to the catheter hub 106, which can permit fluid communication between the catheter tube 104 and the cannula 204. In the illustrated embodiment, the projection 213 extends distally from a bottom surface 217 of the connection interface 211. The connection interface 211 further includes the threaded skirt 215, which may comply with ISO standards for luer fittings. The skirt 215 may include a distal edge 219, which can correspond with a distalmost end or tip of the connector 202. In the illustrated embodiment, the projection 213 extends distally beyond the distal edge 219 of the connector 202.

Figure 10:
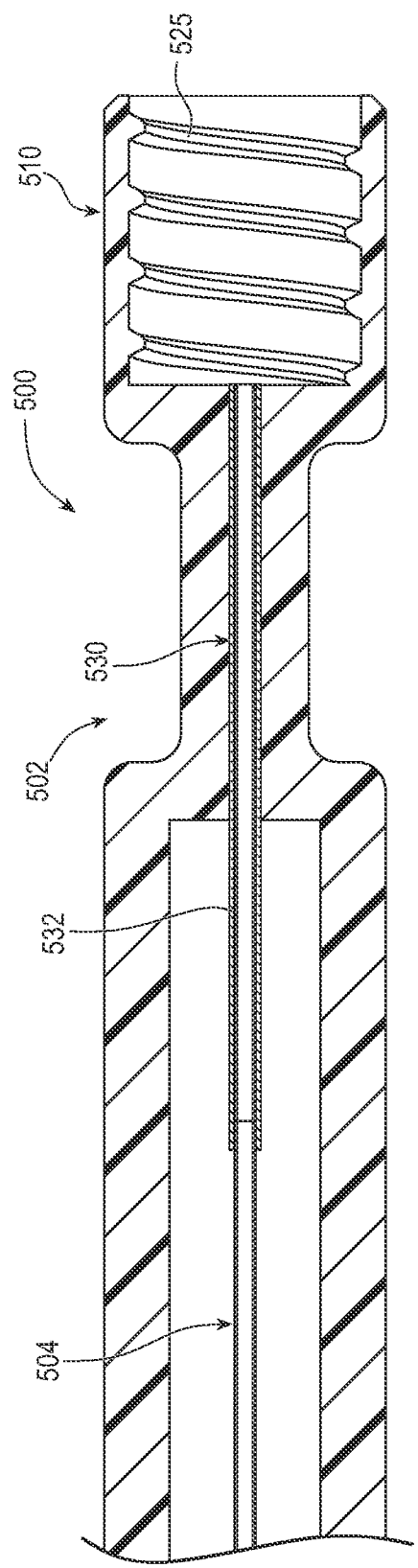
FIG. 10 a cross-sectional view of a distal portion of another embodiment of an access system shown in an undeployed or retracted state.
Figure 11:
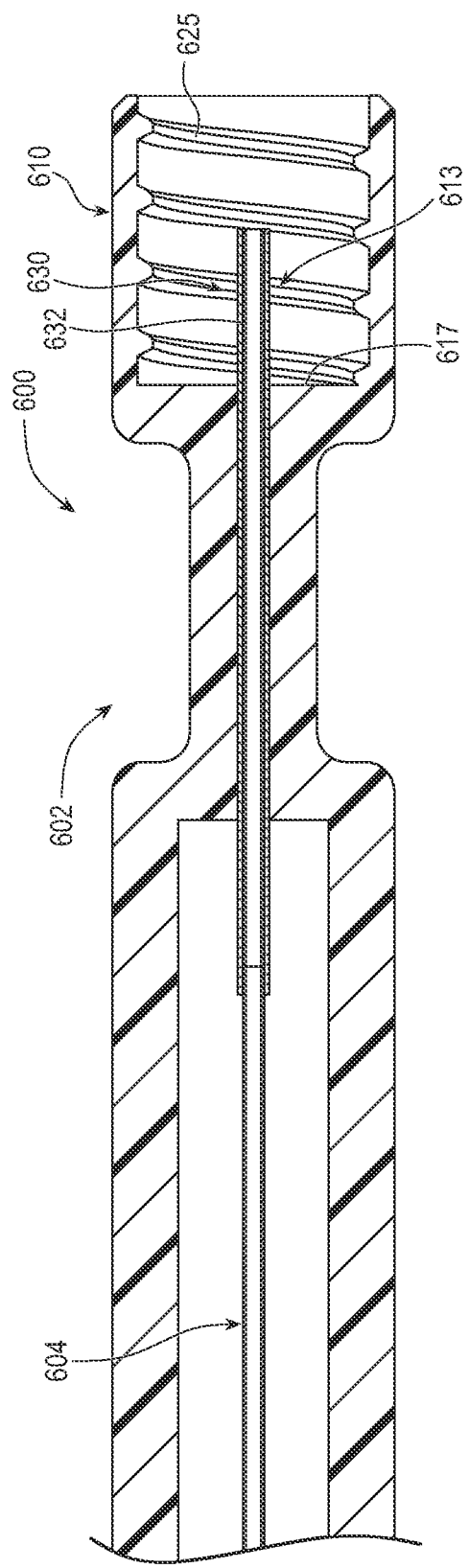
FIG. 11 a cross-sectional view of a distal portion of another embodiment of an access system shown in an undeployed or retracted state.

The coupling interface 210 of the connector 202 can be of any suitable variety. For example, the coupling interface 210 can include threading 225, such as for luer lock interfacing. Similar threading 525, 625 is depicted in FIGS. 10 and 11. In other embodiments, the coupling interface 210 can utilize friction fit or other mechanical engagement (e.g., snap fit). Illustrative examples of friction-fit interfaces are identified as the features 328 and 428 in FIGS. 8 and 9, respectively. An illustrative snap-fit coupling interface is depicted, e.g., in FIG. 32A, as further discussed below.

In various embodiments, the reinforcement member 230 and/or the reinforcing cannula 232 may be flush with the inner, recessed, bottom, or distal-facing surface 217 of the connector 202. For example, in the embodiment depicted in FIG. 8, a distal end of a reinforcing cannula 332 is encompassed by or encased in a material that forms a connector 302.

In other embodiments, such as previously discussed, the reinforcement member 230 and/or the reinforcing cannula 232 may project distally from a distally facing surface of the connector 202, such as from the inner, recessed, bottom, or distal-facing surface 217 of the coupling interface 210. In this manner, the reinforcing reinforcement member 230 and/or the reinforcement cannula 232 can pierce or otherwise defeat valves, stops, etc. of a preplaced catheter system as the connector 202 is coupled to the preplaced catheter system. For example, a catheter hub of a preplaced catheter system may include a septum or a valve that can be pierced, compressed, or otherwise opened by the reinforcement member 230. For example, as previously discussed, the projection 213 of the embodiment depicted in FIG. 7, which includes a distal end of the reinforcement cannula 232 therein, may be configured to open or defeat a valved member of the preplaced catheter system—for example, may defeat a valve associated with the catheter hub 106 (see FIG. 1) in some instances, and/or may defeat a valve associated with an extension set (see, e.g., FIG. 24) coupled with the catheter hub 106.

With reference to FIGS. 9 and 11, the distal end of reinforcement members 430, 630, which define projections 413, 613, may be formed solely by distal ends of reinforcement cannulas 432, 632 that project distally from bottom, inner, recessed, or distally facing surfaces 417, 617, respectively. Each reinforcement cannula 432, 632 can be inserted through a valve as its respective connector 402, 602 is coupled with a preplaced catheter system (whether directly to a catheter hub or to a hub of an extension set), in some instances. In other instances, as discussed below, the reinforcement cannulas 432, 632 can be dimensioned such that the distal tip of the reinforcement cannula 432, 632 is instead positioned at, adjacent to, or slightly proximally recessed from a proximal surface of a valve member as the associated connector 402, 602 is attached to a preplaced catheter system. As further discussed below, in certain of such embodiments, the respective cannula 404, 604 can be advanced distally to pierce through the valve member while being reinforced by the distal projection of the reinforcement cannula 432, 632.

With reference again to FIGS. 5-7, in some embodiments, the cannula 204 can be formed of fewer than three distinct pieces or fewer than three separate segments. For example, in some embodiments, the cannula 204 can include a distal segment 226, such as that previously disclosed, coupled to a rigid tube that extends proximally to the connector 229 (e.g., luer connector) at a proximal end of the cannula 204. Stated otherwise, the medial segment 224 may be extended proximally so as to replace an elongated portion of the proximal segment 222. In some instances, the rigid tube is a metallic tube, such as stainless steel. In further instances, the rigid tube abuts a polymeric tube that forms the distal segment 226, as previously discussed. For example, the polymeric tube of the distal segment 226 and the stainless steel tube of the medial segment 224 can abut at an interface and be connected to each other via heat shrink tubing.

In other instances having an elongated medial segment 226 in place of the proximal segment 222, a polymeric tube may extend continuously along both the distal and medial segments 226, 224. The rigid tube of the medial segment 224 may encompass that portion of the polymeric tube that extends proximally from the distal segment 226. Stated otherwise, in some embodiments, a single polymeric tube (e.g., of polyimide) may extend continuously from the distal tip 217 of the cannula 204 to the proximal connector 229. A second tube, such as the support tube previously described, can sheath a portion of the polymeric tube and extend from the interface 252 all the way proximally to the proximal connector 229. Stated in yet another manner, the cannula 204 can include (1) a distal segment 226, formed solely of a polymeric tube extending distally from the interface 252 to the distal tip 217 of the cannula 204, and (2) a medial segment 224, formed of a continuous proximal extension of the polymeric tube and a second rigid support tube that sheaths or encompasses the proximal extension of the polymeric tube, with each of said continuous proximal extension of the polymeric tube and the support tube extending proximally from the interface 252 and terminating at the proximal connector 229.

In still other embodiments, the rigid tube of the medial segment 224 may be extended proximally through an interior of the proximal segment 222. Stated otherwise, the proximal segment 222 may include a diametrically larger piece (e.g., of plastic) that encases a proximal portion of the medial segment 224. In some embodiments, the rigid cannula (e.g., which may be metallic) of the medial segment 224 may extend proximally to the connector 229.

The proximal segment 222 has been described herein as a portion of the cannula 204. The elongated molded piece that forms the illustrated proximal segment 222 may alternatively be described as an elongated proximal connector 229 (e.g., an elongated luer connector) that extends distally. That is, the proximal segment 222 may be viewed as a distal extension of the connector 229.

FIG. 8 depicts a distal portion of another embodiment of an access system 300, which can resemble other access systems disclosed herein, such as, for example, the access system 200. Accordingly, features of the access system 300 are designated with reference numerals similar to those of the access system 200, with the leading digit "2" being replaced with "3." Relevant disclosure set forth above regarding similarly identified features thus may not be repeated hereafter. Moreover, specific features of the access system 300 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the access system 300. Any suitable combination of the features and variations of the same described with respect to the access system 200 can be employed with the access system 300, and vice versa. Similarly, the access system 300 can suitably be used within the base catheter system 100 and other preplaced catheters and catheter systems described herein. That is, disclosures regarding various access systems 300 can be appropriately applied to other access systems described herein, in the interest of streamlining the present discussion. This pattern of disclosure applies equally to further embodiments depicted in the various figures and described herein, wherein the leading digits may be further altered.

As previously mentioned, the access system 300 includes a connection interface 310 that has a friction-fit arrangement, rather than threading. A distal tip of a reinforcement tube 332 is flush with an inner surface 317 of the connection interface 310.

In the illustrated embodiment, a cannula 304 is shown in a retracted orientation. In this orientation, a distal tip 327 of the cannula 304 is recessed slightly from a distal tip of the reinforcement tube 332.

FIG. 9 depicts another embodiment of an access system 400 that includes a connector 402 having a connection interface 410 that likewise has a friction-fit arrangement. The projection 413 is defined by a distal end of a reinforcement tube 432 that extends distally from an inner or recessed surface 417 of the connection interface 410. In the illustrated embodiment, a distal tip of the reinforcement tube 432 is proximally recessed relative to a distal edge 419 of the connector 402.

In the illustrated embodiment, when a movable cannula 404 is in a retracted position, a distal tip 427 of the cannula is substantially flush with a distal tip of the reinforcement tube 432. In this retracted orientation, the distal tip 427 of the cannula 404 is distally spaced from the inner or recessed surface 417 and is proximally spaced from the distal edge 419 of the connector 402.

As previously discussed, FIGS. 10 and 11 depict additional embodiments of access systems 500, 600 that resemble the access systems 300, 400, respectively. The access systems 500, 600 have connectors 502, 602 having connection interfaces 510, 610 that include threading 525, 625. The access systems 500, 600 include reinforcement members 530, 630 that include reinforcement tubes 532, 632.

In some embodiments, the access systems 300, 400, 500, 600 can be particularly well suited for coupling with closed intravenous catheter systems. As further discussed below, in some embodiments, the reinforcement tubes 332, 432, 532, 632 may be spaced from an outer septum or cover of the closed IV catheter system. In other embodiments, the reinforcement tubes 332, 432, 532, 632 can be dimensioned to extend through the outer septum or cover of the closed IV catheter, but a distal tip thereof may (1) be at or proximally spaced from a proximal surface of a valve (or plug or inner septum), (2) not extend through the valve, and/or (3) not contact the valve, as discussed further below.

Figure 12:
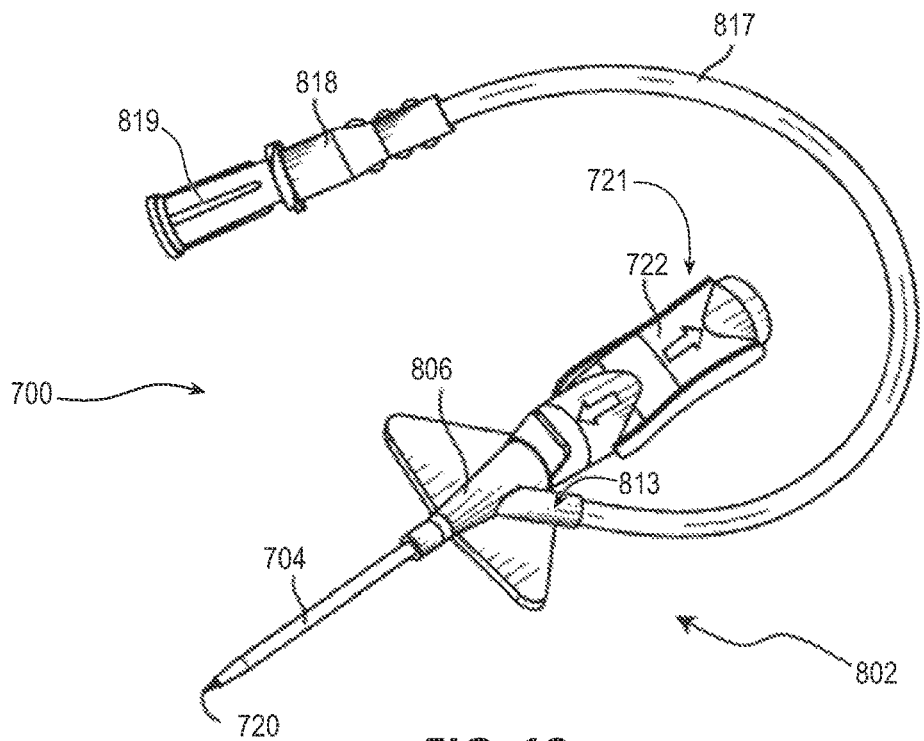
FIG. 12 is a perspective view of an embodiment of a closed intravenous catheter system in a fully assembled state that may be referred to as an insertion configuration.

FIG. 12 is a perspective view of an embodiment of a closed catheter system 700, which may also be referred to herein as a closed base catheter system 700. Any suitable closed catheter system is contemplated, such as, for example, a closed intravenous catheter system. For example, the closed base catheter system 700 can comprise any of the NEXIVA™ lines of catheters (e.g., the DIFFUSICS™ line) available from Becton Dickinson. Certain of such closed catheter systems may have an extension set 802 integrated therein. For example, in the illustrated embodiment, a hub 806 of the extension set 802 includes a side port 813 with an extension tube 817, a connector 818, and a removable vent fitting 819, similar to extension set arrangements that may be used with open intravenous catheter assemblies (e.g., such as the extension set depicted in and described with respect to FIG. 24). The hub 806 may also be referred to as a catheter hub.

The closed catheter system 700 can include a removable needle assembly 721 that includes a needle 720 connected to a needle hub 722. The needle assembly 721 can be coupled with the catheter hub 806 and used during insertion of a catheter tube 704 into the vasculature of a patient, and can be removed from the catheter hub 806 thereafter. The needle 720 and its two-part hub 722 can be inserted into the catheter hub 806 and the catheter tube 704 during assembly of the closed catheter system 700, and can be packaged in such a preassembled configuration, such as that depicted in FIG. 12.

In FIG. 12, the catheter system 700 is shown in an insertion configuration. The needle 720 extends from a distal tip of the catheter 704 to permit insertion of the catheter tube 704 into the vasculature of a patient.

Figure 13:
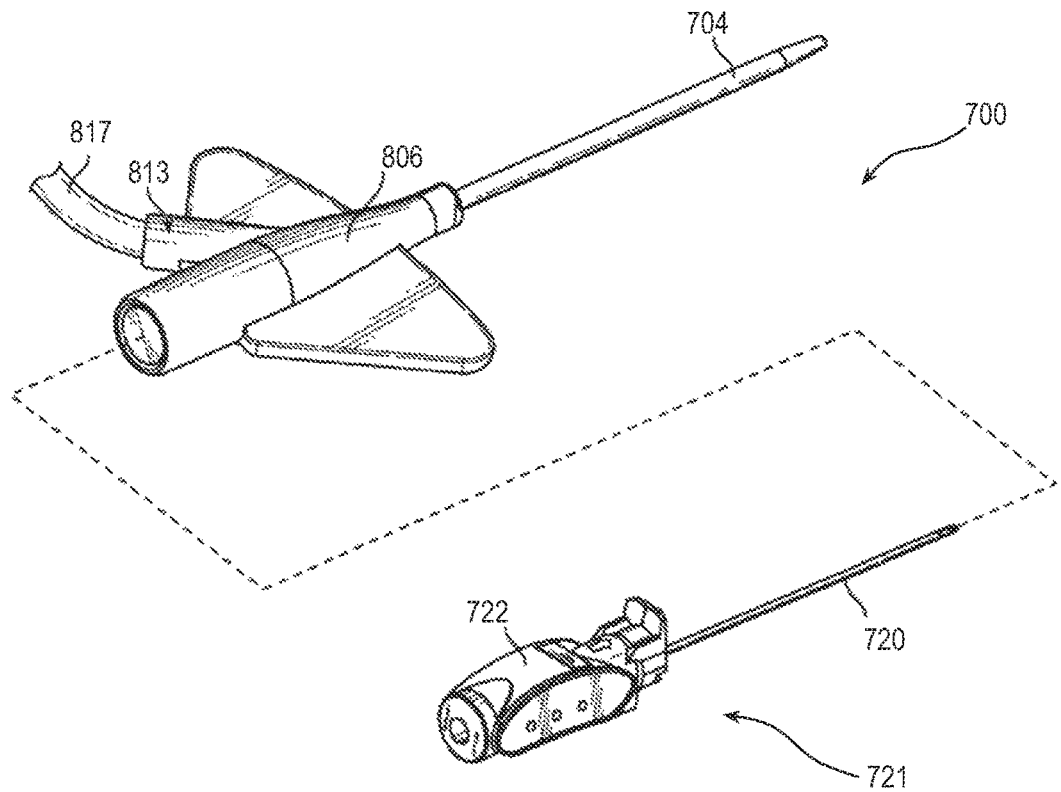
FIG. 13 is a perspective view of the closed intravenous catheter system of FIG. 12 in a state in which a piercing implement has been removed from a hub and catheter tube, which state may be referred to as an access configuration.

FIG. 13 is a perspective view of the closed catheter system 700 in a disassembled state, such as may be achieved after the catheter tube 704 has been inserted into a blood vessel of a patient. The needle assembly 721 is shown as having been removed from the hub 806 and catheter tube 704. The illustrated configuration may be referred to as an access configuration. For example, once the catheter tube 704 has been positioned within the vasculature of the patient in any suitable manner, including those presently employed, and once the needle assembly 721 has been removed, access to the vasculature may be achieved via the placed catheter tube 704. For example, the vent fitting 819 may be removed at any suitable stage, and a fluid source or fluid receptacle may be coupled with the connector 818 if the integrated extension set 802 to achieve fluid delivery to the vasculature and/or fluid removal from the vasculature via the catheter tube 704.

The needle 720 can be fixedly attached to the needle hub 722. In the illustrated embodiment, the needle hub 722 is a two-part hub that provides shielding capabilities to a distal tip of the needle 720 to avoid needle sticks when the needle 720 is withdrawn from the catheter hub 806 after the catheter tube 704 has been introduced into the vessel of the patient.

Figure 14:
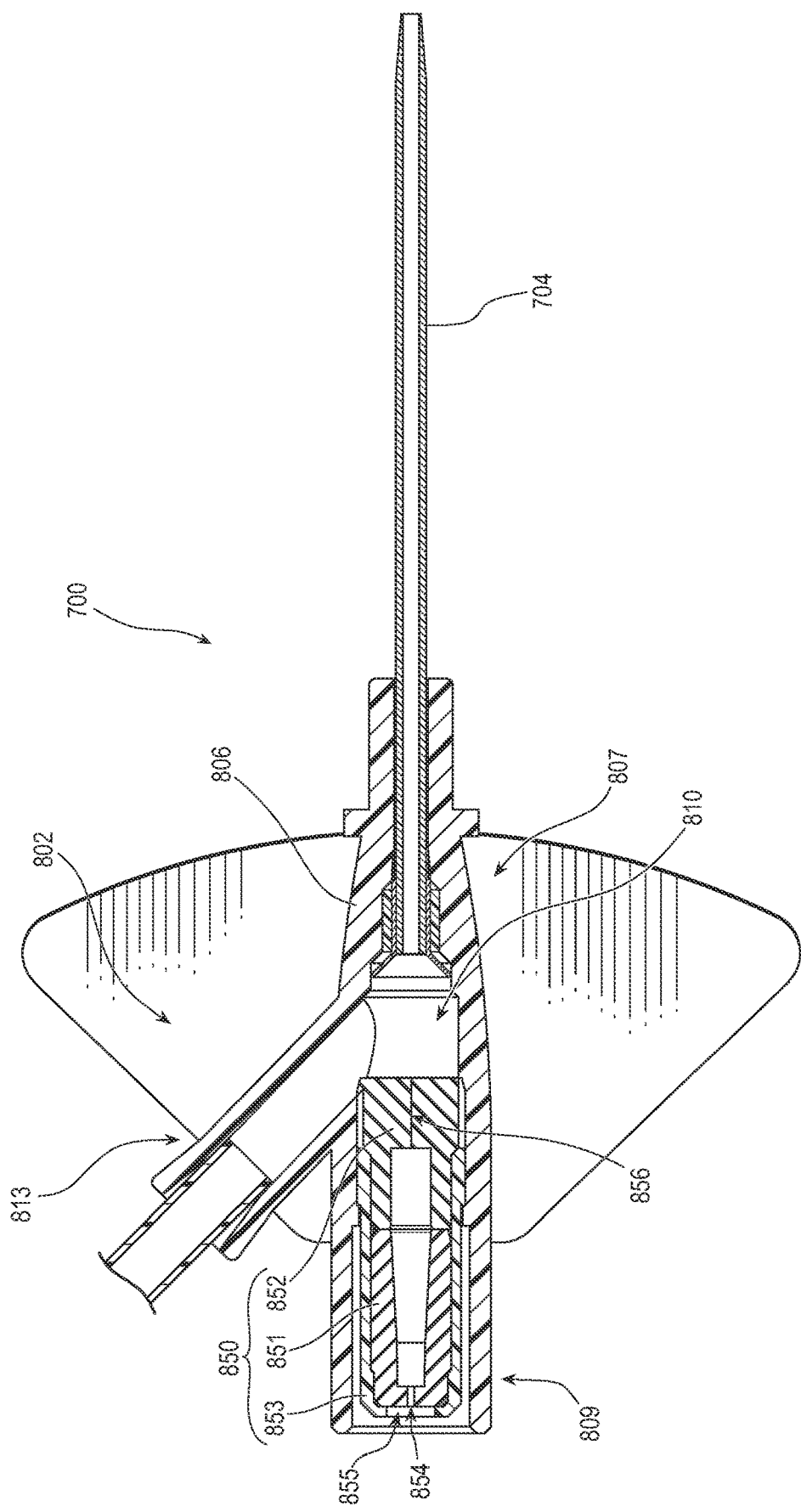
FIG. 14 is a cross-sectional view of a portion of the closed catheter system of FIG. 12 in the access configuration.

FIG. 14 is a cross-sectional view of the catheter hub 806 and the catheter tube 704 of the closed catheter system 700 in an operational state in which the needle 720 has been fully removed from the catheter tube 704 and from the catheter hub 806. The catheter hub 806 can include a distal port 807 in fluid communication with the catheter tube 704, a proximal port 809 that is described below, and the side port 813 of the integrated extension set 802, to which the extension tube 817 and connector 818 (FIG. 12) are coupled. Each of the distal and side ports 807, 813 is in continuous fluid communication with an inner chamber 810.

Certain embodiments of access systems (e.g., the access systems 300, 400, 500, 600), or portions thereof, such as any suitable access system, or portion thereof, disclosed herein can be used with the closed catheter system 700 while in the operational state—namely, the access state—depicted in FIG. 14, in which the needle assembly 721 has been removed. In certain embodiments, the access systems (e.g., 300, 400, 500, 600) may not include their own extension sets (e.g., such as the extension set depicted in FIG. 24), as the catheter hub 806 of the closed base catheter system 700 already includes an extension set integrated therein. In some embodiments, the distal connection interfaces of the access systems 300, 400, 500, 600 depicted in, e.g., FIGS. 8-11 may be particularly well-suited for interfacing with the closed catheter system 700. For example, friction-fit or snap-fit connectors may connect well with certain embodiments of the proximal port 809.

With continued reference to FIG. 14, the proximal port 809 can include a plurality of components coupled thereto or therein. In particular, the proximal port 809 can include an outer or proximal septum or cover 851, an inner or distal septum or plug 852, and a retainer 853. In various embodiments, the septa 851, 852 may be formed of any suitable elastomeric materials. The retainer 853 may be formed of a relatively rigid polymeric material and may interface with a polymeric housing of which the catheter hub 806 is formed to retain the septa 851, 852 within the proximal port 809.

In typical or standard use of the closed catheter system 700, the needle 720 (FIGS. 12 and 13) extends through the retainer 853 and the septa 851, 852 of the proximal port 809, through the catheter hub 806, and through the catheter tube 704 when the closed catheter system 700 is in the insertion configuration. The needle 720 may more generally be referred to as a piercing member or as a piercing implement. For example, in other embodiments, the needle 720 may be replaced with any other suitable piercing member or piercing element, such as, for example, a trocar. The proximal port 809 may also be referred to as an implement port.

Upon placement of the catheter tube 704 within a vessel of the patient, the needle 720 is fully removed, thus placing the closed catheter system 700 in the access state depicted in FIG. 14. As the needle 720 is removed from the inner septum, distal septum, or plug 852, the plug 852 self-seals to close off the proximal end of the inner chamber 810 and prevent fluid communication between the inner chamber 810 and the proximal port 809. In typical or standard use, the proximal port 809 is no longer used, and all further fluid communication with inner chamber 810 and/or the catheter 704 is achieved vie the integrated extension set 802, or stated otherwise, via the side port 813. The plug 852 is not used in any further access events, and desirably remains sealed for the remaining use of the closed catheter system 700.

As previously discussed, and as further discussed hereafter, certain embodiments of access systems are able to interface with the proximal port 809 in an atypical fashion by coupling with the proximal port 809 and passing a cannula (e.g., 304, 404, 504, 604) through the plug 852 and into the catheter tube 704. Through this process, the cannula (e.g., 304, 404, 504, 604) can, upon passing through the plug 852, achieve fluid communication with the inner chamber 810 and/or the catheter tube 704. Moreover, when the cannula (e.g., 304, 404, 504, 604) extends through the plug 852, fluid is able to pass through the cannula, and hence is able to pass through the plug 852 and, more generally, through the proximal port 809. Moreover, in some instances, multiple access events through the plug 852 in this manner are possible. The plug 852 can again self-seal upon removal of the cannula (e.g., 304, 404, 504, 604). Accordingly, due to the ability to use the distal septum or plug 852 to selectively achieve fluid communication between (1) the catheter tube 704 and/or the inner chamber 810 of the catheter hub 806 and (2) an exterior of the closed catheter system 700 via the proximal port 809, the distal septum or plug 852 may additionally or alternatively be referred to herein as a valve or valve member 852. Further, the distal septum, plug, valve, or valve member 852 may also or alternatively be referred to as a seal or sealing member.

In view of the foregoing, the septa 851, 852 and the retainer 853 may be described in additional or alternative terms. For example, it may be said that the proximal port 809 includes a valve assembly 850 that can permit selective fluid communication between the inner chamber 810 and the proximal port 809. In some instances, the valve assembly 850 is configured to fluidically seal against the needle 720 when the needle 120 is fully inserted therethrough, such as in the insertion configuration depicted in FIG. 12, and is configured to self-seal so as to prevent fluid from egressing from the inner chamber 810 and through the proximal port 809 upon removal of the needle 720 therefrom to achieve the access configuration depicted in FIG. 13.

With continued reference to FIG. 14, the valve assembly 850 of the proximal port 809 can include the proximal septum 851, the distal septum 852, and the retention member or retainer 853. The retainer 853 can comprise a generally tubular element that interfaces with a body of the catheter hub 806 to retain the proximal and distal septa 851, 852 within the proximal port 809. That is, the retainer 853 may cooperate with a housing portion of the hub 806 to hold the septa 851, 852 in place within the proximal port 809. Although the illustrated valve assembly 850 includes multiple septa 851, 852, only the distal septum 852 may provide the valving functionality of the valve assembly 850 discussed above, and further discussed below.

In some embodiments, the proximal septum 851, which is also or alternatively referred to as a cover, includes an opening 854, which may be centered relative to the port 809. The opening 854 may be a permanent opening. When the closed catheter system 700 is in the insertion state depicted in FIG. 12, the needle 720 can extend through the opening 854 of the proximal septum 851. The opening 854 may be preformed and/or may be sufficiently large such that the opening 854 does not self-seal upon removal of the needle 720 therefrom.

The retainer 853 can include an opening 855, which can be larger than the opening 854 of the proximal septum 851. The opening 855 can be concentric with the opening 854.

As previously noted, the valve 852 may be self-sealing, such that upon removal of the needle 720 therefrom, a sealable region 856, which may also or alternatively be referred to as a "closable opening" (as opposed to the permanent opening 854 of the proximal septum 851), self-seals to prevent fluid communication between the chamber 810 and the port 809. In some embodiments, a fluid-tight seal formed by the closable opening or sealable region 856 is sufficiently strong to withstand high pressures, such as may be achieved when power injection is performed via the side port 813 to pass fluid through the inner chamber 810 and the distal port 807.

In certain embodiments, when an access system (e.g., either access system 400, 600) is coupled with the proximal port 809 of the closed catheter system 700, a reinforcement member of the access system (e.g., the reinforcement member 430, 630 of the access system 400, 600, respectively) can extend through the openings 855, 854 of the retainer 853 and the proximal septum 851, respectively, and a distal tip of the reinforcement member (e.g., the distal tip of the reinforcement tube 432, 632) may be positioned at or proximally recessed from a proximal surface of the distal septum or valve 852. One such illustrative coupling event and coupling configuration are depicted in FIGS. 33 and 34, respectively, which is discussed further below. The distal tip of the reinforcement member (e.g., 430, 630) may be fixed in this position relative to the valve 852. The reinforcement member (e.g., 430, 630) can thereby align a movable/deployable cannula (e.g., 404, 604) of the access system with the valve 852. Stated otherwise, a longitudinal axis of the reinforcement tube (e.g., 432, 632) can be centered on and colinear with a line that extends through the sealable region 856 of the valve 852, which line corresponds to a sealed tract from which the needle 720 has previously been removed (this may also be referred to as a needle tract through the sealable region 856). The reinforcement member (e.g., the reinforcement tube) does not contact the valve 852 or extend into or through the valve 852. Rather, the cannula (e.g., 404, 604) of the access system is extended out of the reinforcement member (e.g., the reinforcement tube 432, 632) and then through the sealable region 856 of the valve 852.

In still other embodiments, when an access system (e.g., either access system 300, 500) is coupled with the proximal port 809 of the closed catheter system 700, a reinforcement member (e.g., 330, 530) of the access system (e.g., 300, 500) can remain external to, recessed from, or otherwise not extend through the openings 855, 854 of the retainer 853 and the proximal septum 851, respectively. A distal tip of the reinforcement member (e.g., the distal tip of the reinforcement tube 332, 532) may be proximally recessed from a proximal surface of the distal septum or valve 852. Indeed, the distal tip of the reinforcement member (e.g., the distal tip of the reinforcement tube 332, 532) may sufficiently recessed from the valve 852 so as to also be at or proximally recessed from a proximal surface of the cover or proximal septum 851. The distal tip of the reinforcement member (e.g., 330, 530) may be fixed in this position relative to the valve 852. The reinforcement member (e.g., 330, 530) can align a movable/deployable cannula (e.g., the cannula 304, 504) of the access system with a longitudinal axis of the valve 852. Stated otherwise, a longitudinal axis of the reinforcement tube (e.g., 332, 532) can be centered on and colinear with the line through the sealable region 856 of the valve 852 that corresponds to a sealed tract from which the needle 720 has previously been removed (e.g., the needle tract through the sealed region 856), as previously described. An imaginary extension of this line in the proximal direction can extend through the openings 855, 854 of the retainer 853 and the proximal septum 851, respectively, and be aligned with the longitudinal axis of the reinforcement tube. The reinforcement member (e.g., 330, 530), or in certain embodiments, the reinforcement tube (e.g., 332, 532) does not contact the valve 852 or extend into or through the valve 852. Rather, the cannula (e.g., 304, 504) of the access system is extended out of the reinforcement member (e.g., 330, 530), then through the proximal septum 851, and then through the sealable region 856 of the valve 852 along a substantially rectilinear path.

In certain embodiments, the distal end of the deployable cannula (e.g., any of the cannulae 304, 404, 504, 604 of the access systems 300, 400, 500, 600) can successfully be extended through the valve 852 without damaging or kinking the cannula (e.g., 304, 404, 504, 604) and without damaging the valve 852. In some instances, by avoiding contact of the reinforcing tube with the valve 852, or by not embedding the reinforcing tube within the valve 852, during an insertion or deployment event, the material of the valve 852 remains in a more relaxed state, or stated otherwise, is in a less compressed or less stressed state, or may be in a fully uncompressed or unstressed state, which can facilitate insertion of the movable cannula (e.g., 304, 404, 504, 604) therethrough. Moreover, as previously noted, in some instances coupling the access system (e.g., 300, 400, 500, 600) with the proximal port 809 can center the reinforcement member (e.g., 330, 430, 530, 630) relative to the valve 852 and thereby align the cannula (e.g., 304, 404, 504, 604) with the valve 852, such that the cannula (e.g., 304, 404, 504, 604) can be inserted along the same path through the valve 852 or through the same portion of the valve 852 from which the needle 720 has previously been removed (e.g., the needle tract through the sealable region 856), which may facilitate or enable insertion of the cannula (e.g., 304, 404, 504, 604) through the valve 852. In certain embodiments, reinforcement features as described elsewhere herein, can make such insertion of only the cannula (e.g., 304, 404, 504, 604) through the valve 852 possible. In some instances, if the cannula is not reinforced at more proximal regions thereof, the cannula may bend or kink upon contact with the valve 852, which can prevent insertion of the cannula through the valve 852.

In some instances, it may be advantageous to not insert a reinforcement tube (e.g., either reinforcement tube 432, 632 of the access systems 400, 600) or any portion thereof into the valve 852 in order to thereafter advance the cannula (e.g., 404, 604) through reinforcement tube to thereby achieve passage of the cannula through the valve. As previously noted, maintaining the reinforcement tube (e.g., 432, 632) external to the valve 852 (or proximally recessed from a proximal surface of the valve 852) prior to and during insertion of the cannula (e.g., 404, 604) through the valve 852 can maintain the valve 852 in a relatively relaxed or uncompressed state, which can facilitate distal movement of the cannula (e.g., 404, 604) through the valve 852. In other or further instances, damage to the valve 852, such as coring of the valve 852 by a distal tip of the reinforcement tube (e.g., 432, 632) and/or permanent stretching or deformation of the valve 852 by a relatively larger outer diameter of the reinforcement tube (e.g., 432, 632), can be avoided.

Stated otherwise, as can be appreciated from the present disclosure, in certain instances, it can be advantageous to advance the cannula through the valve 852 without first inserting a separate supporting or reinforcing member into or through the valve 852 (e.g., a reinforcing member of a larger diameter that could stretch out or deform the valve 852 and/or of a variety which could undesirably core a portion of the valve 852 upon passage therethrough). That is, it can be advantageous to advance the cannula through the valve 852 independently, on its own, or without doing so through a separate member (e.g., reinforcement or support member) that has previously been advanced into or through the valve and that remains positioned in or through the valve so as to define an open channel (e.g., corresponding to the inner lumen of the support member) through at least a portion of the valve for subsequent passage of the cannula.

In some instances, after an access system (e.g., 300, 400, 500, 600) has been used with the closed catheter system 700 and removed therefrom, the valve 852 can remain sealed during subsequent use of the integrated extension set 802. Stated otherwise, use of an access system (e.g., 300, 400, 500, 600) with the closed catheter system 700 can have no adverse effect on operation of the valve 852, or can preserve effective or normal operation of the valve 852. Stated otherwise, use of the access system with closed catheter system 700 can, upon removal of the access system, permit the inner septum 852 to once again plug or seal the proximal port 809. For example, in some instances, after removal of a deployable cannula (e.g., 304, 404, 504, 604) from the catheter tube 704 and from the distal valve 852 of the closed catheter system 700 after use of an access system (e.g., 300, 400, 500, 600) therewith, the integrated extension set 802 of the closed catheter system 700 can be used to access the vasculature of the patient (e.g., for an infusion or aspiration event) via the placed catheter tube 704 in the same manner as may have been accomplished prior to use of the access system (e.g., 300, 400, 500, 600) with the closed catheter system 700. In some instances, the valve 852 remains sufficiently strong and fluid-tight to permit use of the closed catheter system 700 for power injections through the side port 813 after removal of the access system (e.g., 300, 400, 500, 600). In certain embodiments, use of an access system (e.g., 300, 400, 500, 600) with the closed catheter system 700 has no adverse effect on the valve 852, such that after 1, 2, 3, 4, 5, 10, 15, 20, or 25 or more coupling and decoupling cycles of one or more access assemblies (e.g., 300, 400, 500, 600) with and from a closed catheter system 700, the valve 852 of the closed catheter system 700 continues to operate in its original manner. For example, the valve 852 can continue to maintain a fluid-tight seal during a power injection through the closed catheter system 700 after one or multiple coupling/decoupling event or events.

FIG. 15 is a perspective view of another embodiment of an access system 1000 configured to be coupled with embodiments of a base catheter system. For example, in some embodiments, the access system 1000 is configured to be coupled with an open base catheter system, whether directly (e.g., by direct attachment to a catheter hub) and/or indirectly (e.g., by direct attachment to a proximal port of an extension set that is attached to a catheter hub), as further discussed below. The access system 1000 is shown in a fully retracted or undeployed state.

In the illustrated embodiment, the access system 1000 includes a connector 1002 and a cannula 1004 that is selectively advanceable and retractable relative to the connector 1002. As with other embodiments described herein, the cannula 1004 can include a connector 1029 at a proximal end thereof. In the illustrated embodiment, the connector 1029 is a female luer.

The connector 1002 can include a connection interface 1010 and a reinforcement member 1030. In the illustrated embodiment, the reinforcement member 1030 includes a distal projection 1013 that extends a significant distance past a distal face of the connection interface 1010. The distal projection 1013 may be narrower and more elongated than a luer interface, in some instances.

With reference to FIG. 16, in some embodiments, the access system 1000 includes an internal stop, hub, or follower 1060, to which a proximal segment 1022 of the cannula 1004 is attached. The follower 1060 can be sized to prevent the cannula 1004 from being retracted fully from a sheath 1005. Stated otherwise, a proximal end of the sheath 1005 and the follower 1060 can cooperate to delimit proximal movement of the cannula 1004. The follower 1060 can have a greater radial dimension than an opening 1061 at a proximal end of the sheath 1005. In various embodiments, the follower 1060 can be fixedly secured to one or more components of the cannula 1004 (e.g., the proximal segment 1022 and/or a medial segment 1024) and can move in response to movement of the cannula 1004. Stated otherwise, the follower 1060 can move in unison with the cannula 1004 and in response to forces imparted to the cannula 1004. In particular, the follower 1060 is not directly accessible by a user, and instead moves solely in response to forces applied to the proximal segment 1022 of the cannula 1004 by a user at an exterior of the sheath 1005.

In certain embodiments, the follower 1060 can restrict, inhibit, or prevent rotational movement of the cannula 1004 relative to the sheath 1005 about a longitudinal axis, which these components may have in common. Stated otherwise, the follower 1060 can cooperate with the sheath 1005 to rotationally lock the cannula 1004 relative to the sheath 1005, thus preventing relative rotation of these components about a central longitudinal axis about which the components are concentrically arranged. For example, in the illustrated embodiment, the follower 1060 includes a protrusion 1062 that fits within a longitudinal groove 1064 defined by the sheath 1005. In other embodiments, the groove/protrusion interface may be reversed. For example, in some embodiments, the follower 1060 defines a groove that receives a longitudinal protrusion that extends inwardly from the sheath 1005. The protrusion 1062 and the groove 1064 may be referred to as a rotational alignment mechanism 1065 or as a rotational lock. Any suitable rotational alignment mechanism is contemplated.

Other embodiments may permit free rotation between the cannula 1004 and the sheath 1005. For example, some embodiments may be devoid of a rotational alignment mechanism. For example, in some embodiments, an interior surface of the sheath 1005 and an exterior surface of the follower 1060 each may be substantially cylindrical so as to readily permit relative rotation.

Figure 17A:
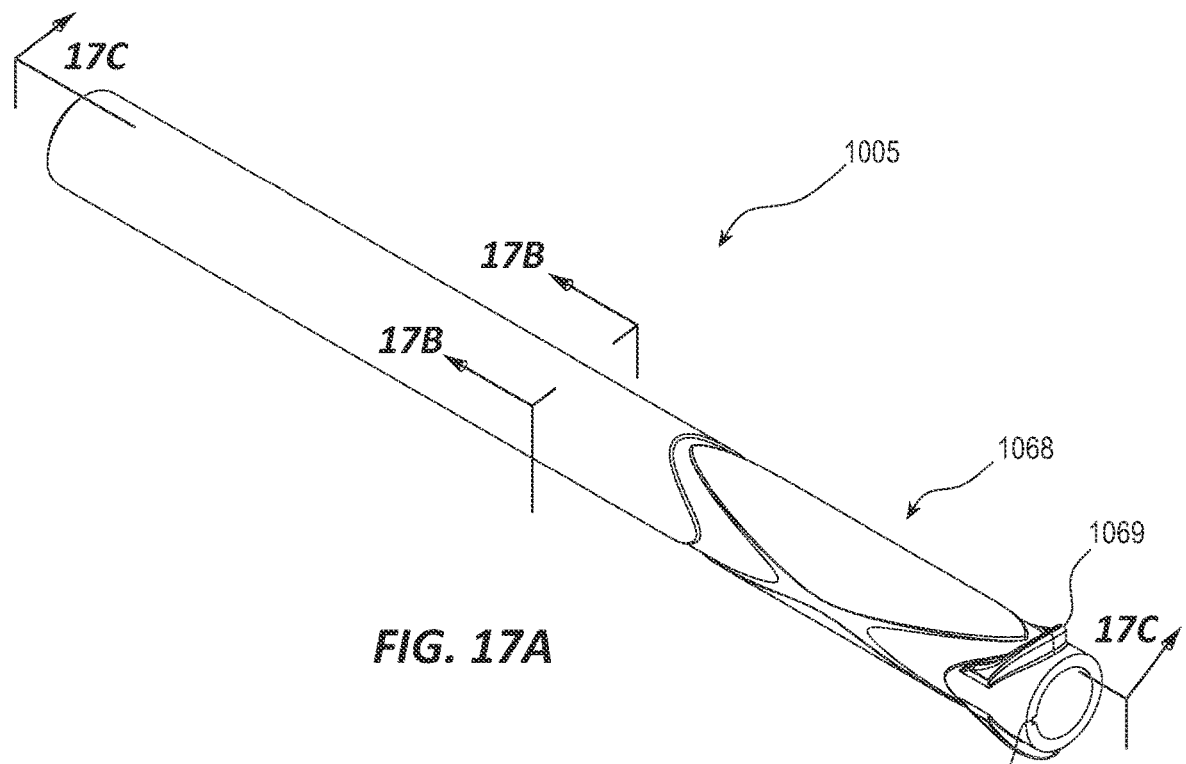
FIG. 17A is a perspective view of an embodiment of a housing that is compatible with the access system of FIG. 15.
Figure 17B:
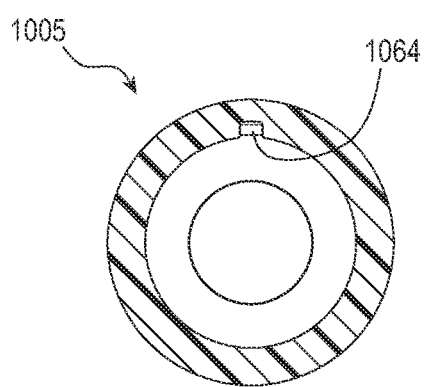
FIG. 17B is a cross-sectional view of the housing of FIG. 17A.
Figure 17C:
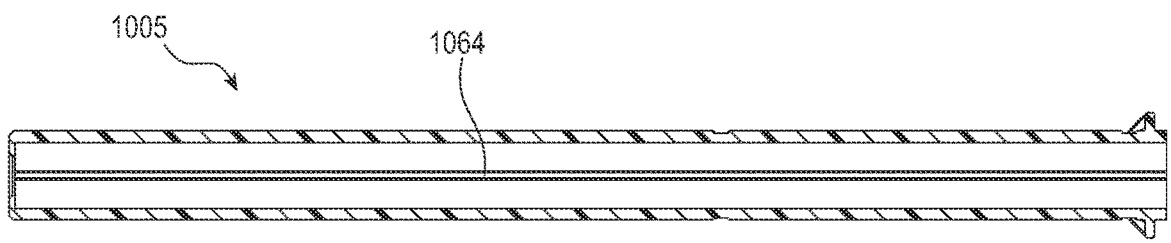
FIG. 17C is another cross-sectional view of the housing of FIG. 17A.

FIG. 17A is a perspective view of the housing 1005, and FIGS. 17B and 17C are separate cross-sectional views of the housing 1005. The groove 1064, which may also be referred to as an internal track, is visible in each view. With reference to FIG. 17A, in some embodiments, the housing 1005 includes one or more gripping features 1068. The gripping features 1068 can include one or more of grooves, coverings, coatings, and/or other surface features to enhance grippability, ergonomics, and/or manipulation of the housing 1005. The gripping features 1068 of the illustrated embodiment includes grooves and a high friction layer of material. The gripping features 1068 further include a pair of diametrically opposite raised wings 1069 at a distal end of the housing 1005. The wings 1069 may, in some instances, assist in manipulation of the housing 1005 to rotate the housing 1005 for coupling with the access system 1000 with a connector of a catheter hub or an extension set hub.

Figure 18A:
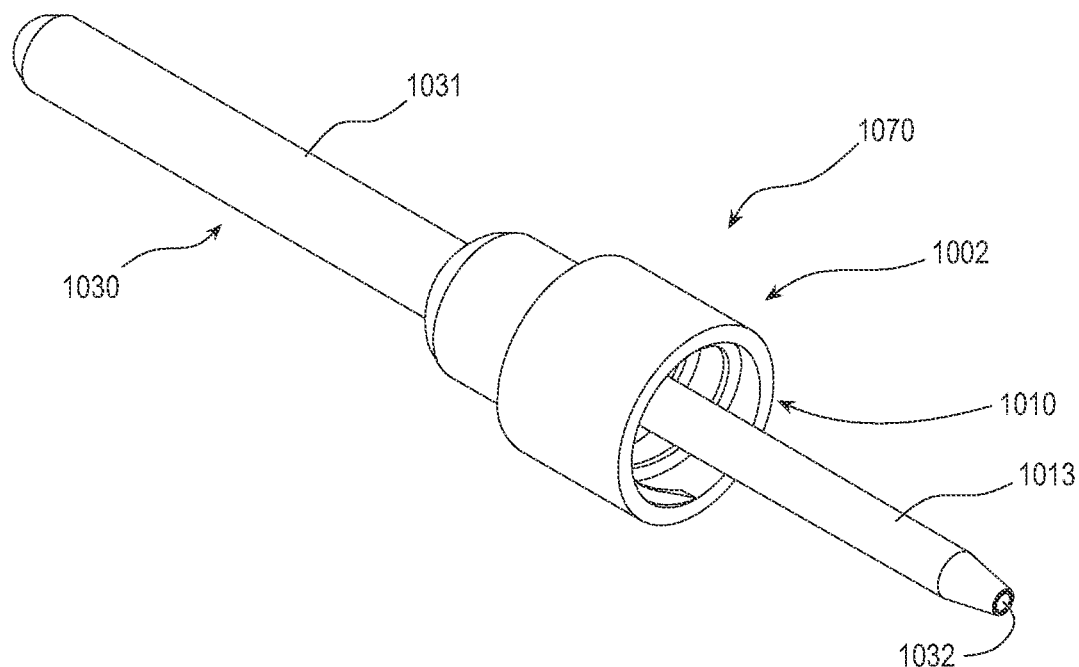
FIG. 18A is a perspective view of an embodiment of a coupling member that is compatible with the access system of FIG. 15.
Figure 18B:
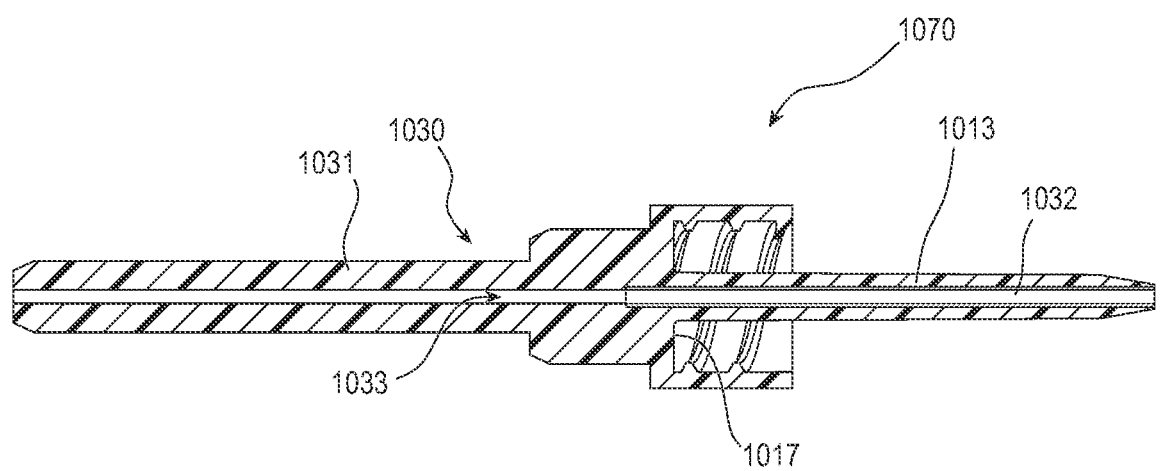
FIG. 18B is a cross-sectional view of the coupling member of FIG. 18A.

FIGS. 18A and 18B depict an embodiment of a coupling member 1070 that may be attached to a distal end of the housing 1005, and may form a distal end of the connector 1002. The coupling member 1070 can include any suitable connection interface 1010, such as those previously discussed. In the illustrated embodiment, the connection interface 1010 includes internal threading, such as may be used, for example, to couple with a threaded luer interface.

The coupling member 1070 can define a reinforcing member 1030. As with other embodiments previously discussed, the reinforcing member 1030 can include a distal projection 1013 that extends distally from a bottom, inner, or recessed surface 1017 of the connection interface 1010. In the illustrated embodiment, the distal projection 1013 is formed of two different components. In particular, an outer layer of the distal projection 1013 is formed of a polymeric material, and constitutes an extension of a continuous casting or molding of polymeric material of which much of the reinforcing member 1030 is formed. The distal projection 1030 further includes at least a distal end of an internally situated reinforcing tube 1032, such as reinforcing tubes previously described. The reinforcing tube 1032 is embedded within the coupling member 1070. In some embodiments, the polymeric portion of the coupling member 1070 is overmolded onto the reinforcing tube 1032.

The reinforcing member 1030 can further include an elongated proximal projection 1031 of the polymeric material. The proximal projection 1031 can extend proximally into an internal cavity of the sheath 1005 when the coupling member 1070 is secured to the sheath 1005, as shown in FIG. 16. A lumen 1033 can extend continuously through the proximal projection 1031 and through the reinforcing tube 1032. In some embodiments, an internal diameter of the lumen 1033 is substantially constant along a full length of the reinforcing member 1030, or stated otherwise, along a full length of the lumen 1033 that extends from a proximal tip of the proximal projection 1031 to a distal tip of the reinforcing tube 1032.

In other embodiments, the proximal projection 1031 may be omitted, and the reinforcing tube 1032 can be extended proximally, similar to an arrangement such as that depicted in FIG. 7.

Figure 19A:
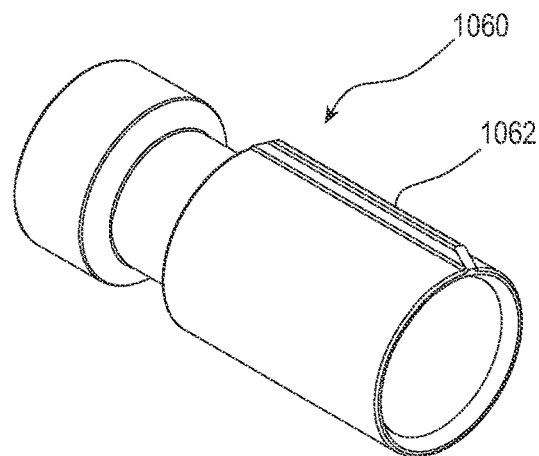
FIG. 19A is a perspective view of an embodiment of a follower that is compatible with the access system of FIG. 15.
Figure 19B:
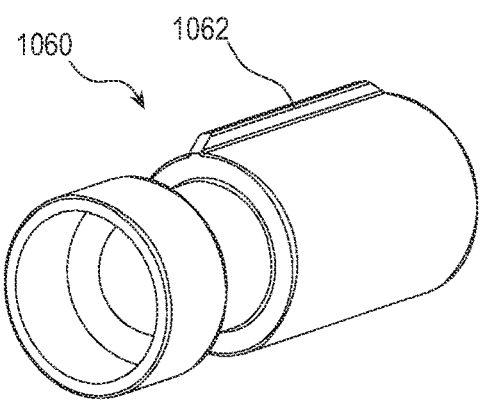
FIG. 19B is another perspective view of the follower of FIG. 19A.
Figure 19C:
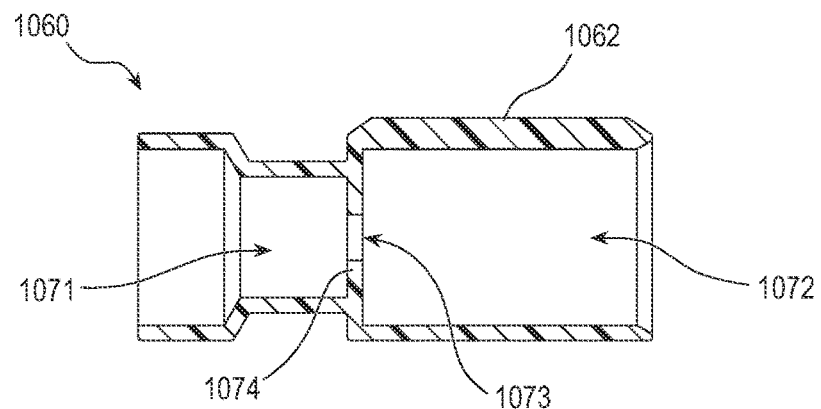
FIG. 19C is a cross-sectional view of the follower of FIG. 19A.

FIGS. 19A and 19B are perspective views of the follower 1060, and FIG. 19C is a cross-sectional view of the follower 1060. The longitudinally extending protrusion 1062 is shown in each view. The follower 1060 defines a proximal cavity 1071 sized to receive a distal end of the proximal segment 1022 of the cannula 1004 therein. In some embodiments, the distal end of the proximal segment 122 is adhered to the follower 1060 (see FIG. 23A). The follower 1060 can further define a distal cavity 1072 that is enlarged relative to an outer diameter of the medial segment 1024 of the cannula 1004, such that the medial segment 1024 can readily pass through the distal cavity 1072 (see FIG. 23A). The follower 1060 can include an opening 1073 through a sidewall 1074, which sidewall 1074 separates the proximal and distal cavities 1071, 1072 from each other.

With simultaneous reference to FIGS. 19A, 19B, and 23A, the opening 1073 can be sized to permit passage therethrough of the medial segment 1024 of the cannula 1004. A proximal end of a tube that forms at least a portion of the medial segment 1024 can extend through the opening 1073 and be embedded in a distal end of the tube that forms at least a portion of the proximal segment 1022 of the cannula 1004, as shown in FIG. 23A. In some embodiments, these tubes may be adhered to one another. In certain illustrative manufacturing processes, the tubes of the cannula 1004 may be attached to one another and then passed distally through the opening 1073, at which point the distal end of the proximal tube can be adhered to the follower 1060 within the cavity 1071.

Figure 20:
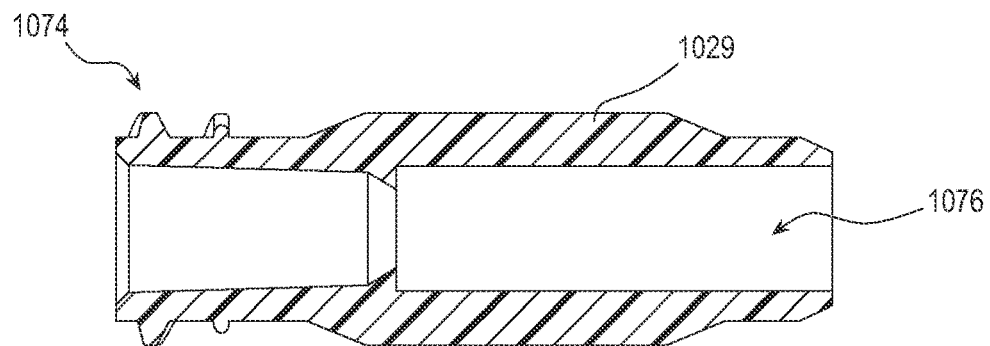
FIG. 20 is a cross-sectional view of an embodiment of a connector that is compatible with the access system of FIG. 15.

FIG. 20 is a cross-sectional view of an embodiment of the connector 1029. In the illustrated embodiment, the connector 1029 includes a female luer interface 1074. The connector 1029 further defines a cavity 1076 sized to receive a proximal end of the proximal segment 1022 of the cannula 1004 therein (see, e.g., FIG. 16).

Figure 21:
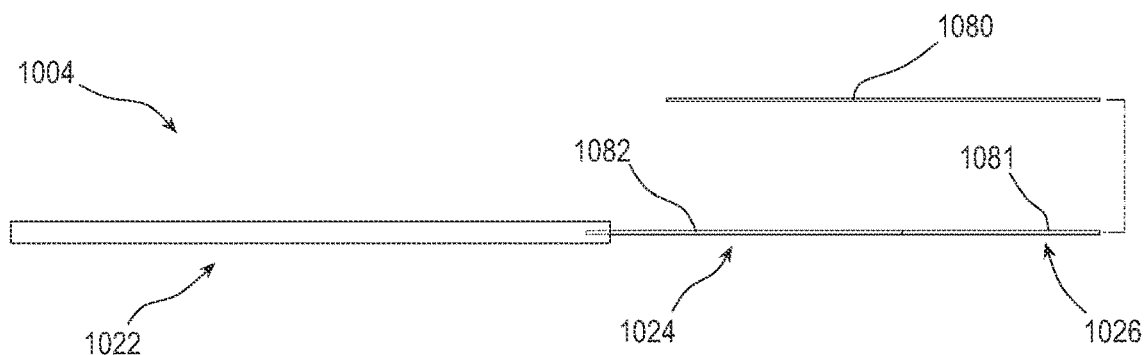
FIG. 21 is a partially exploded elevation view of an embodiment of a cannula showing a tie layer separated from a two-component portion of the cannula that the tie layer is used to connect together.

FIG. 21 is a partially exploded elevation view of the cannula 1004 showing a tie layer 1080 separated from a distal tube 1081 and a medial tube 1082. In the illustrated embodiment, the distal tube 1081 is included in the distal segment 1026 of the cannula 1004 and the medial tube 1082 is included in the medial segment 1024 of the cannula 1004. The distal tube 1081 can be of any suitable material for the distal segment 1026, such as those previously described. For example, in some embodiments, the distal tube 1081 is formed of polyimide. The medial tube 1082 likewise may be formed of any suitable material for the medial segment 1024. For example, in some embodiments, the medial tube 1082 comprises a stainless steel tube.

The tie layer 1080 can be used to join the tubes 1081, 1082 together. For example, as discussed previously, in some embodiments, the tie layer 1080 can comprise a thin-walled tube of heat shrink material that is advanced over at least a proximal end of the distal tube 1081 and a distal end of the medial tube 1082. The heat shrink tube can then be heated to securely attach to the ends of the tubes 1081, 1082 together. As with other embodiments discussed herein, in various embodiments, the distal tube 1081 comprises a polymeric material and the medial tube 1082 comprises a metallic material. The tie layer 1080 can comprise any suitable material. For example, in various embodiments, the tie layer 1080 includes a tube of heat-shrinkable polyethylene terephthalate (PET).

Figure 22:
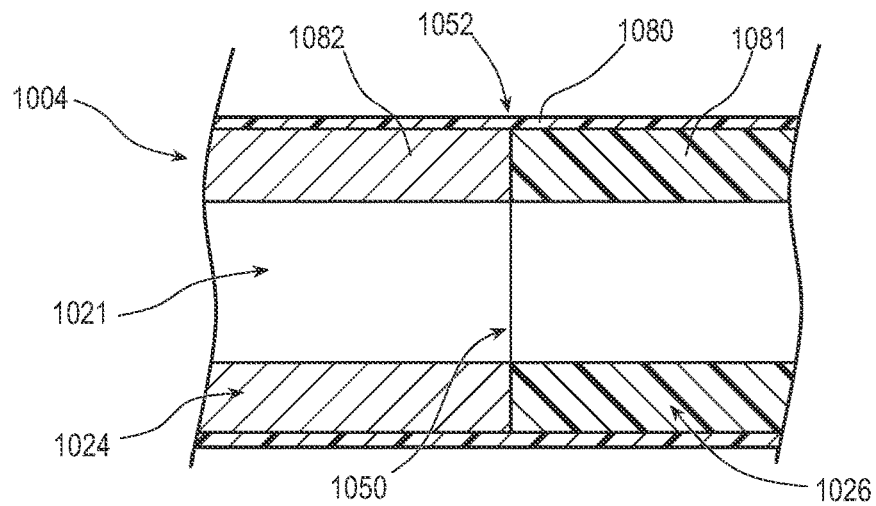
FIG. 22 is an enlarged cross-sectional view of the cannula with the tie layer in place over the two-component portion of the cannula.

FIG. 22 is an enlarged cross-sectional view of the cannula 1004 with the tie layer 1080 in place over the tubes 1081, 1082. In the illustrated embodiment, the adjoined ends of the tubes 1081, 1082 abut one another. In particular, in the illustrated embodiment, each tube 1081, 1082 end has a substantially flat or planar surface that is transverse to a longitudinal axis of the cannula 1004. These transverse surfaces abut one another to provide a surface of continuous contact. In some instances, abutment along a plane that is perpendicular to a longitudinal axis through the tubes 1081, 1082 can inhibit bending at that junction of the tubes 1081, 1082. For example, by maintaining tight contact at the abutting faces, the tubes 1081, 1082 may be less inclined to bend or kink at the junction, as compared, for example, to circumstances in which space may be provided between the adjacent tube ends. Consistent with other disclosures herein, the tubes 1081, 1082 may be said to abut one another at an interface 1052 of the cannula 1004. The distal end of the medial tube 1082 represents a distal terminus 1050 of the medial member 1024.

In the illustrated embodiment, the inner diameters of the tubes 1081, 1082 are substantially identical, such that a lumen 1021 of the cannula 1004 is substantially smooth along at a transition from the distal tube 1081 to the medial tube 1082. In some instances, a smooth transition can inhibit or prevent hemolysis of blood due to its passage through the interface 1052.

In some embodiments, a distal tip of the tie layer 1080 can be proximally spaced from the distal tip of the cannula 1004. Such an arrangement may permit the distal tip of the tie layer to contact an internal surface of the catheter tube 104 at a distal tip of the catheter tube 104 to delimit proximal movement of the cannula 1004 relative to the catheter tube 104. This may be an effective manner for limiting an amount of the cannula 1004 that can extend past the distal end of the catheter tube 104. In some instances, contact between the distal end of the tie layer 1080 and a narrowed inner surface of the catheter tube 104 at the distal tip of the catheter tube 104 can provide tactile feedback to a user regarding a position of the cannula 1004 relative to the catheter tube 104, and in particular, to alert the user that the cannula 1004 has been fully deployed.

FIG. 23A is a cross-sectional view of a generally proximal portion of the access system 1000 when the access system 1000 is in a retracted state, or stated otherwise, when the cannula 1004 of the access system 1000 is in a retracted state. As shown, the follower 1060 may be substantially at a proximal end of the sheath 1005 when the cannula 1004 is in the retracted state.

FIG. 23B is a cross-sectional view of a distal portion of the access system 1000 in the retracted state. In this state, similar to previously described embodiments, the interface 1052 of the cannula 1004 can be positioned within the reinforcement member 1030. Stated otherwise, an entirety of a proximal end of the distal segment 1026 of the cannula 1004, including a proximal tip of the distal segment 1026, and the distal terminus 1050 of the medial segment 1024 each can be positioned within the reinforcement member 1030 when the cannula 1004 is in the retracted state. In the illustrated embodiment, the interface 1052 is positioned within the proximal extension 1031 of the reinforcement member 1030 in this operational state.

In the illustrated embodiment, the distal tube 1081 has a distal tip that is slightly recessed relative to a distal tip of the reinforcement tube 1032 of the reinforcement member 1030. In the illustrated embodiment, an entirety of the distal tube 1081 is positioned within the reinforcement member 1030. A distal end of the distal tube 1081 is within the reinforcement tube 1032 of the reinforcement member 1030, while a proximal end of the distal tube 1081 is within the proximal extension 1031 of the reinforcement member 1030. As with other embodiments discussed herein, the reinforcement member 1030 can prevent the distal tube 1081 from bending or kinking during an insertion event, due to the reinforcement provided by the relatively close fit between the inner diameter of the reinforcement member 1030 and the outer diameter of the distal tube 1081.

Figure 24:
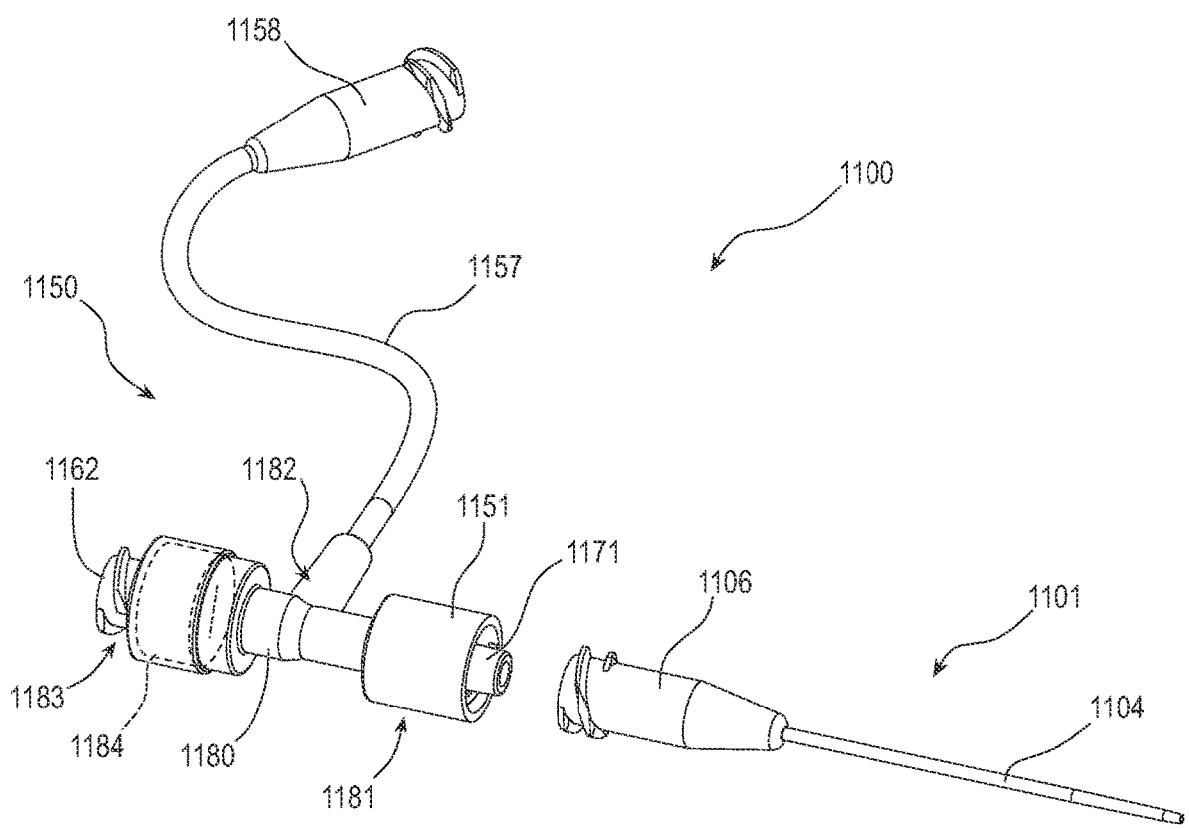
FIG. 24 is an exploded perspective view of an embodiment of a base catheter assembly that includes an embodiment of an open intravenous catheter assembly and an embodiment of an extension set that is couplable to the open intravenous catheter assembly.

FIG. 24 is an exploded perspective view of an embodiment of a base catheter assembly 1100 that includes an embodiment of an open intravenous catheter assembly 1101 and an embodiment of an extension set 1150 that is couplable to the open intravenous catheter assembly 1101. The catheter assembly 1101 includes a catheter hub 1106 and a catheter tube 1104, which can resemble the catheter hub 106 and the catheter tube 104 described previously.

The extension set 1150 includes an extension hub 1180 that includes a distal port 1181, a side port 1182, and a proximal port 1183. The distal port 1181 can include a connector 1151 of any suitable variety configured to couple with the catheter hub 1106. In the illustrated embodiment, the connector 1151 comprises a rotatable luer lock connector for selective engagement of a male luer 1171 with the catheter hub 1106. The side port 1182 includes an extension tube 1157 coupled thereto. A connector 1158 is attached to an opposite end of the extension tube 1157. The proximal port 1183 can include a connector 1162, to which a connection interface of any suitable access system (e.g., 200, 300, 400, 500, 600, 1000) can be attached. In some embodiments, a valve 1184, which may also or alternatively be referred to as a septum, seal, etc., may be included within the proximal port 1183. In some instances, the projection 1013 of the access system 1000 can be capable of extending through the valve 1184, and the cannula 1004 can be deployed, advanced, or extended distally from the distal end of the projection 1013 at a position distal of the valve 1184.

Each of the distal port 1181, the side port 1182, and the proximal port 1183 can be in fluid communication with an inner chamber 1173 (see FIG. 25) defined by the extension hub 1180. As noted, in some embodiments, the proximal port 1183 may permit selective fluid communication with the inner chamber 1173 via the valve 1184.

Figure 25:
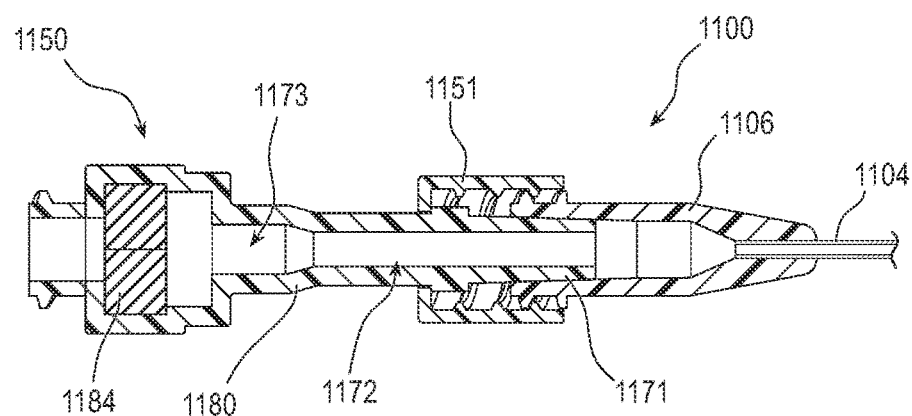
FIG. 25 is a cross-sectional view of the base catheter assembly of FIG. 24 in an assembled state.

FIG. 25 is a cross-sectional view of the base catheter assembly 1100 in an assembled state. The cross-sectional view is taken such that the side port 1182 is not shown. The male luer 1171 can be inserted into and fluidically sealed with the female luer of the catheter hub 1106. The male luer 1171 can have an elongated lumen 1172 at an interior thereof, which corresponds with a distal end of the inner chamber 1173. The lumen 1172 can be a necked down or narrowed section of the inner chamber 1173. In general, when the access system 1000 is coupled with the extension set 1150, rather than directly with the catheter hub 1106 of the catheter assembly 1101, the cannula 1004 travels through a greater distance before entering the catheter tube 1104. Stated otherwise, the catheter hub 1106 provides a first unsupported length between a distal tip of the access system 1000 and a proximal end of the catheter tube 1104 when the access system 1000 is coupled directly to the catheter hub 1106, whereas the catheter hub 1106 and the extension hub 1180, when coupled together, provide a second unsupported length between the distal tip of the access system 1000 and the proximal end of the catheter tube 1104, when the access system 1000 is directly coupled, to the extension hub 1180, and the second unsupported length is significantly greater than the first unsupported length.

FIG. 26 is a side elevation view of the access system 1000 in the retracted state coupled with the assembled base catheter assembly 1100, which includes the extension set 1150 that has the side port 1182. FIG. 27 is a cross-sectional view of a distal portion of the access system 1000 in the retracted state while coupled with the assembled base catheter assembly 1100. As with FIG. 25, the cross-sectional view is taken such that the side port 1182 of the extension set 1150 is not shown.

With the connector 1002 of the access system 1000 coupled with the connector 1162 of the extension set 1150, the distal projection 1013 of the reinforcement member 1030 extends into the inner chamber 1173 of the extension hub 1180. In the illustrated embodiment, the distal tip of the distal projection 1013 is positioned within a proximal end of the narrowed lumen 1172 of the male luer 1171. The distal tip of the projection 1013 is proximally spaced from a proximal tip 1107 or proximal edge of the catheter hub 1106. Accordingly, as previously discussed, the cannula 1004 has a greater distance to travel through the extension hub 1180 and the catheter hub 1106 in order to enter the proximal end of the catheter tube 1104 than is needed when an access system 1000 is coupled directly to a catheter hub 1106. In some embodiments, the distal projection 1013 may be longer and/or narrower for access assemblies that are intended for use with extension sets than are those intended for use directly with catheter hubs 1106. Moreover, in the illustrated embodiment, a distal end of the distal projection 1013 is advanced into the narrowed lumen 1172 of the male luer 1171. Correspondingly, in some embodiments, the distal projection 1013 may be longer than and/or narrower than a standard male luer.

Figure 28:
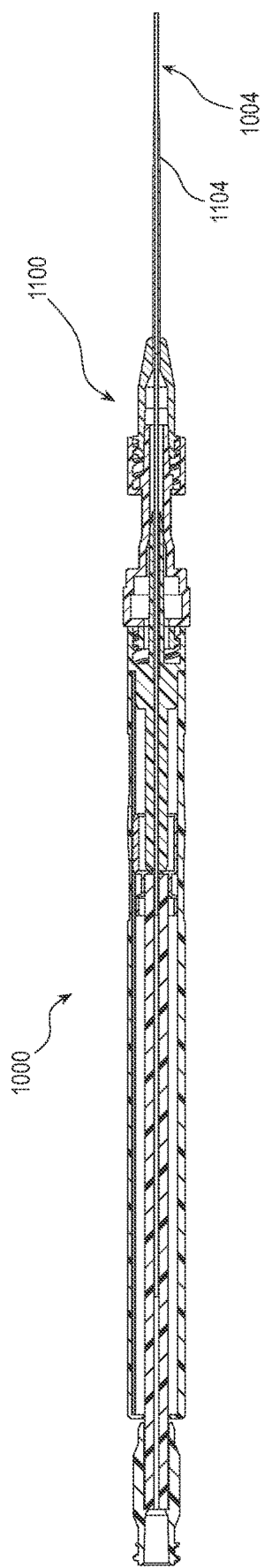
FIG. 28 is a cross-sectional view of the access system of FIG. 15 in a fully deployed state while coupled with the assembled base catheter assembly of FIG. 25.
Figure 29A:
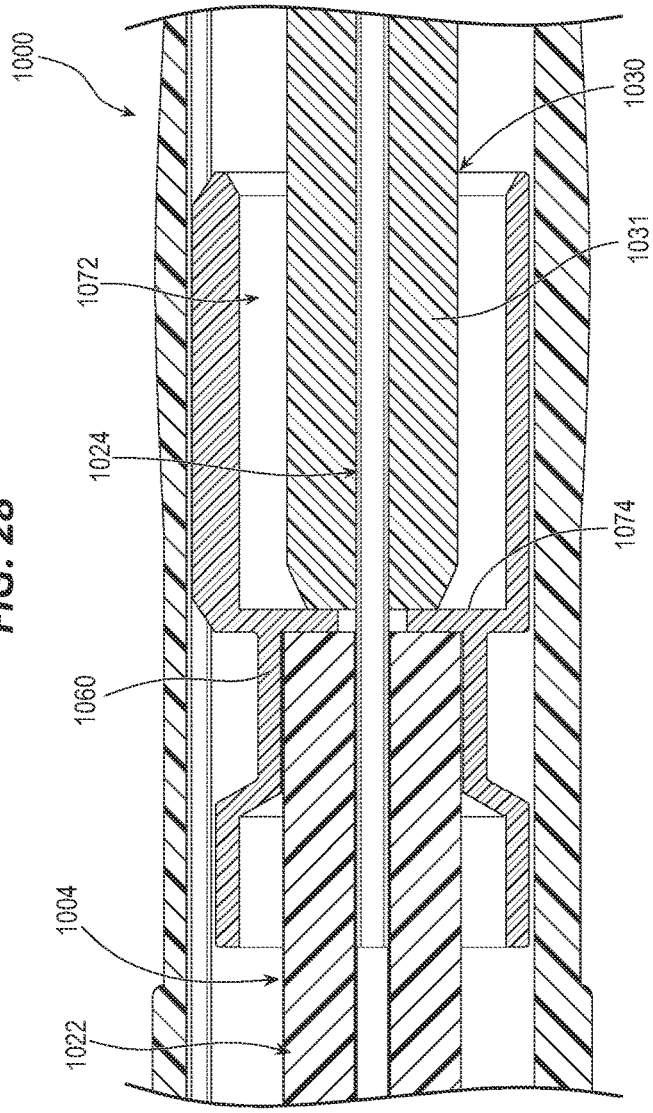
FIG. 29A is a cross-sectional view of a generally intermediate portion of the access system while in the configuration depicted in FIG. 28.
Figure 29B:
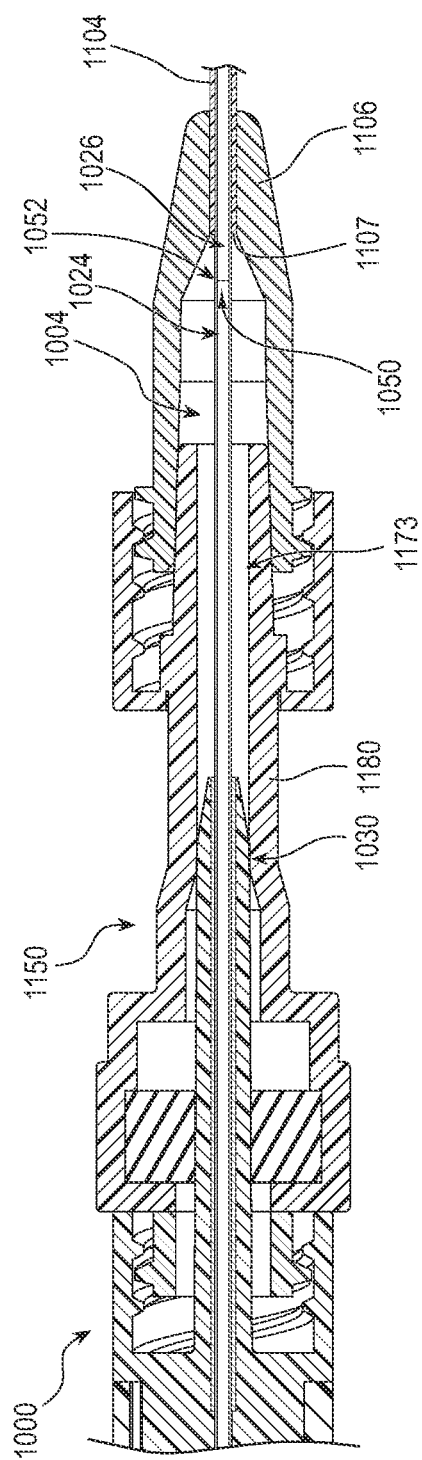
FIG. 29B is a cross-sectional view of a generally distal portion of the access system of FIG. 15 and a proximal portion of the assembled base catheter assembly of FIG. 25 while in the configuration depicted in FIG. 28.
Figure 29C:
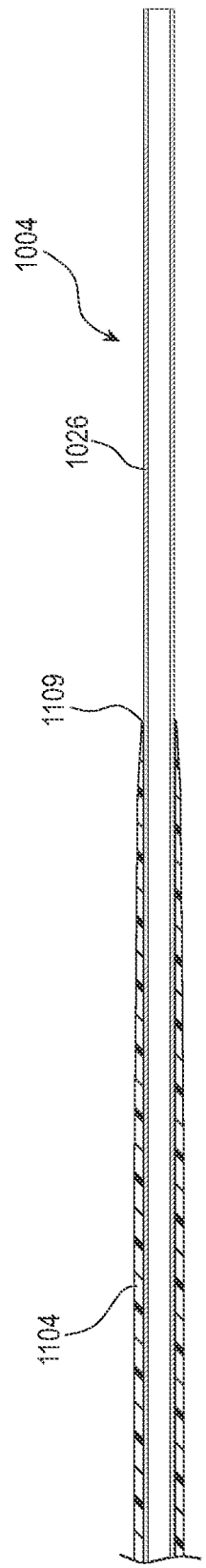
FIG. 29C is a cross-sectional view of distal ends of the access system of FIG. 15 and the assembled base catheter assembly of FIG. 25 while in the configuration depicted in FIG. 28.

FIG. 28 is a cross-sectional view of the access system 1000 in a fully deployed state while coupled with the assembled base catheter assembly 1100. FIGS. 29A-29C are close-up cross-sectional views of various portions of the access system 1000 and the base catheter assembly 1100 in this operational configuration. In particular, FIG. 29A depicts a generally intermediate portion of the access system 1000, FIG. 29B depicts a generally distal portion of the access system 1000 and a proximal portion of the base catheter assembly 1100, and FIG. 29C depicts the distal ends of the access system 1000 and the base catheter assembly 1100.

As shown in FIG. 29A, in some embodiments, the proximal extension 1031 of the reinforcement member 1030 can delimit distal movement of the cannula 1004. As previously discussed, the proximal segment 1022 of the cannula 1004 may be fixedly secured to the follower 1060. The distal cavity 1072 of the follower 1060 can have a sufficiently large inner diameter to receive a proximal end of the proximal extension 1031 of the reinforcement member 1030 therein. As the cannula 1004 is advanced distally, the distal cavity 1072 of the follower 1060 advances over the proximal end of the proximal extension 1031 until contact is made between the sidewall 1074 of the follower 1060 and the proximal extension 1031. This contact can prevent further distal advancement of the cannula 1004.

With reference to FIG. 29B, in the illustrated embodiment, when the cannula 1004 is in the fully deployed position, the distal segment 1026 extends into and through the catheter tube 1104. In particular, as shown in FIG. 29C, in the illustrated embodiment, the distal segment 1026 of the cannula 1004 extends a significant distance beyond a distal tip 1109 of the catheter tube 1104. In various embodiments, the distal segment 1026 may extend distally beyond the distal tip of the catheter tube 1104 by a distance that is no less than 3, 5, 10, or 15 times greater than an outer diameter of the distal segment 1026.

With reference again to FIG. 29B, when the cannula 1004 is in the fully deployed position, the interface 1052 at which the distal and medial segments 1026, 1024 meet may be positioned proximally relative to the proximal tip 1107 of the catheter tube 1104. Stated otherwise, the distal terminus 1050 of the medial segment 1024 may remain external to the catheter tube 1104, while being positioned distal of the reinforcing member 1030. In some instances, the intrinsic support or self-reinforcing properties of the medial segment 1024 can inhibit kinking or buckling of the cannula within the elongated, generally unsupported region of the inner chamber 1173 of the extension hub 1180 and the internal chamber of the catheter hub 1106 as the cannula 1004 is advanced distally.

In other embodiments, the medial segment 1024 may enter, and further, may pass through at least a proximal portion of the catheter tube 1104. For example, as previously described, in some embodiments, the distal and medial segments 1026, 1024 may have substantially the same outer diameter dimensions, such that the medial segment 1024 could readily follow the distal segment 1026 into the catheter tube 1104.

Relative lengths of, e.g., the reinforcement member 1030 (e.g., the proximal projection 1031 thereof) and the cannula 1004—particularly the overall length of the reinforcement member 1030 and a length of the portion of the cannula 1004 that is inserted through extension set 1150 and into and through the catheter tube 1104—can be adjusted to ensure that a distal tip of the cannula 1004 reaches a desired position relative to the distal tip of the catheter tube 1104 when the cannula 1004 is in the fully deployed state. For example, as previously discussed, in various embodiments, a distal tip of the cannula 1004 may desirably extend distally beyond, may be substantially flush with, or may be slightly proximally recessed relative to the distal tip of the catheter tube 1104 when the cannula 1004 is in the fully deployed state.

Relative lengths of, e.g., the reinforcement member 1030 (e.g. the proximal extension 1031 thereof) and the medial segment 1024 can be adjusted to ensure that a distal tip of the medial segment 1024 reaches a desired position relative to the proximal end of the catheter tube 1104 when the cannula 1004 is in the fully deployed state. For example, as previously discussed, in various embodiments, a distal tip or distal terminus 1050 of the medial segment 1024 may remain proximally recessed, may be substantially flush with, or may enter into the proximal end of the catheter tube 1104 when the cannula 1004 is in the fully deployed state.

In other embodiments, the medial segment 1024 may include an outer tube, or support tube (e.g., such as the support tube 1495 depicted in FIGS. 56A and 56B and described below). In some embodiments, at least an outer diameter of the support tube may be larger than an opening at the proximal end of the catheter tube 1104 (e.g., which correspond to an inner diameter of the catheter tube 1104). The distal tip of the support tube, which corresponds to the distal terminus 1050 of the medial segment 1024, can prevent the medial segment 1024 from entering into the catheter tube 1104. In some embodiments, use of a larger diameter support tube as just described can advantageously act as a primary defense against entry of the support tube into the catheter tube 1104. In other embodiments, this can act as a failsafe to ensure that the distal tip of the support tube does not enter the catheter tube 1104, such as, for example, where other dimensions of the access assembly 1000 also have been selected to prevent the support tube from entering the catheter tube 1104. For example, in some embodiments, it may be desirable to avoid entry of the distal tip of the support tube, which otherwise could, in some arrangements, potentially deform, scrape, mar, and/or damage the catheter tube 1104 if permitted to enter therein. In other embodiments, the support tube may be sufficiently narrow to enter the catheter tube 1104.

With continued reference to FIG. 29B, as previously discussed, there may be a significant distance between the distal tip of the reinforcement member 1030 and the proximal end of the catheter tube 1104 when the extension set 1150 is present. In some instances, the self-reinforced medial segment 1024 can be sufficiently strong and/or rigid to avoid bending, kinking, or buckling within the unfilled portion of the cavity 1173 of the extension hub 1180 and the adjoining unfilled cavity of the catheter hub 1106 as the cannula 1004 is distally advanced through this enlarged cavity region (i.e., enlarged as compared with the constriction provided by the reinforcement member 1030). In other or further instances, the self-reinforced medial segment 1024 can maintain alignment of the distal segment 1026 with a longitudinal axis of the catheter tube 1104 as the cannula 1004 is advanced distally. In other or further instances, the self-reinforced medial segment 1024 can reduce an unsupported length of the cannula 1004 within the extension hub 1180 and further, in some instances and/or in later stages of deployment, within the catheter hub 1106 as the cannula 1004 is advanced distally to the fully deployed state.

In some instances, the cannula 1004 may not be moved to a fully deployed state. For example, in some instances, the cannula 1104 may only be advanced from the initial or retracted position to a partially advanced position. This partially deployed, partially advanced, or intermediate state may be sufficient to achieve a desired position of the distal tip of the cannula 1004 beyond or within the distal end of the catheter tube 1104. For example, in some embodiment, the access system 1000 may be usable with a variety of different base catheter systems that may have varying lengths of catheter tubes 1104, and the user may deploy the cannula 1004 by a different amount depending on which length of catheter tube is present.

Figure 30:
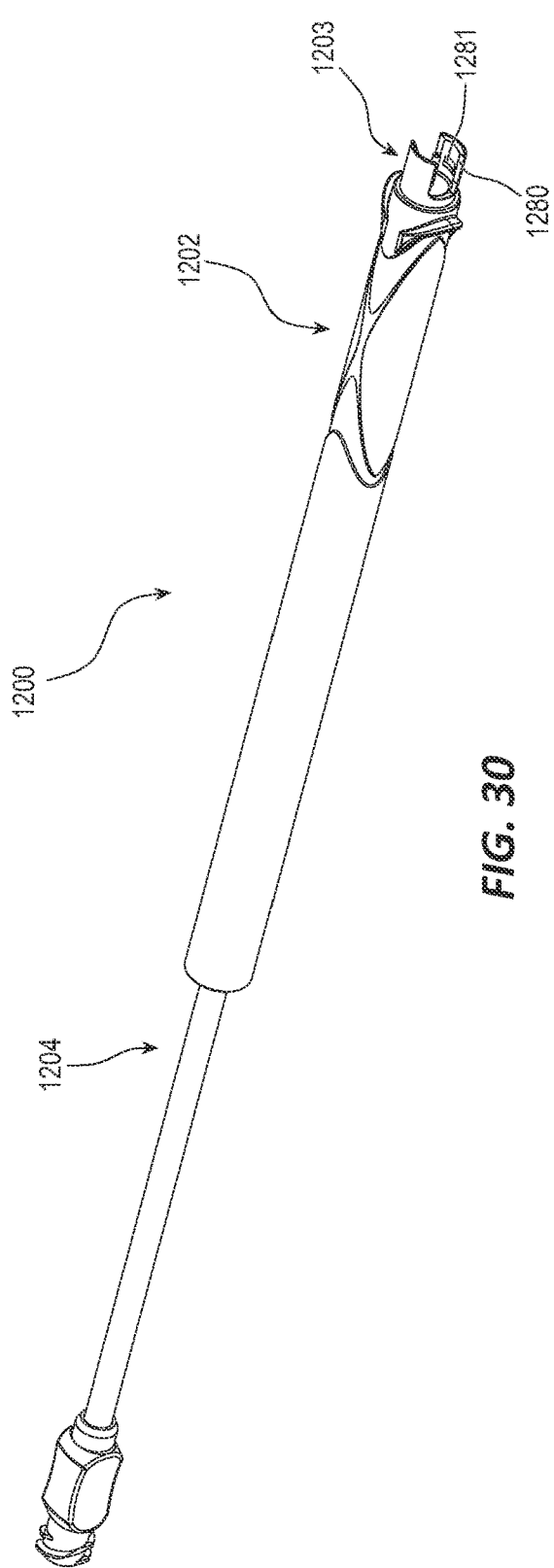
FIG. 30 is a perspective view of another embodiment of an access system configured to be coupled with embodiments of a base catheter system, with the access system being shown in a retracted or undeployed state.

FIG. 30 is a perspective view of another embodiment of an access system 1200 configured to be coupled with embodiments of a base catheter system, with the access system 1200 being shown in a retracted or undeployed state. The access system 1200 may be particularly well-suited for use with a closed intravenous catheter system, such as, for example, a NEXIVA™ closed catheter system. Embodiments of the access system 1200 may resemble, e.g., embodiments of the access systems 300, 400, 500, 600 described above. Relevant disclosures regarding the various access systems 300, 400, 500, 600, 1200 thus may be applied interchangeably.

For example, the access system 1200 can include a cannula 1204 of any suitable variety, including those disclosed elsewhere herein. In some embodiments, the cannula 1204 can be of any of the varieties discussed above, such as, for example, with respect to the cannulas 204, 1004, or below, such as, for example, with respect to the cannula 1404.

Figure 32A:
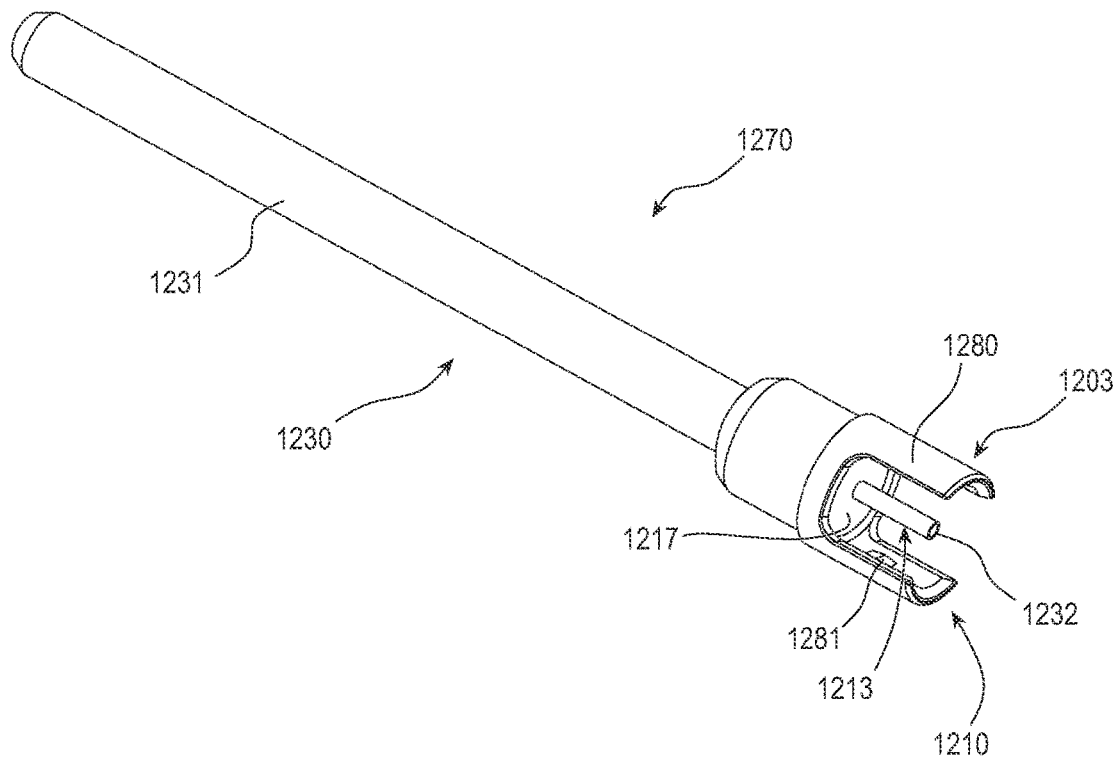
FIG. 32A is a perspective view of an embodiment of a coupling member that is compatible with the access system of FIG. 30.

In the illustrated embodiment, the access system 1200 includes a connector 1202 that is configured to couple with the proximal port 809 of embodiments of a closed intravenous catheter system 700 (see, e.g., FIGS. 14 and 34). For example, the distal end of the connector 1202, can include a snapping or snap-fit arrangement. In the illustrated embodiment, the connector end 1202 includes a pair of opposing arms or flaps 1280 with inward protrusions 1281 to securely snap onto the proximal port 809, as shown in FIG. 32A (see also FIGS. 33 and 34).

Figure 31:
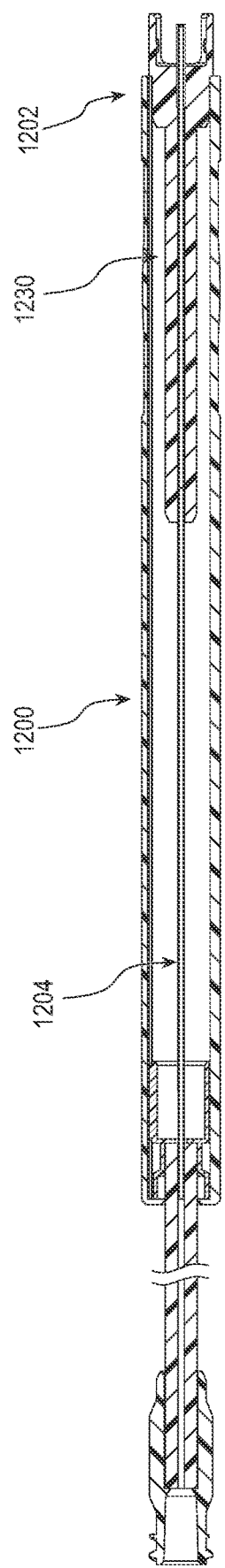
FIG. 31 is a cross-sectional view of the access system of FIG. 30.
Figure 32B:
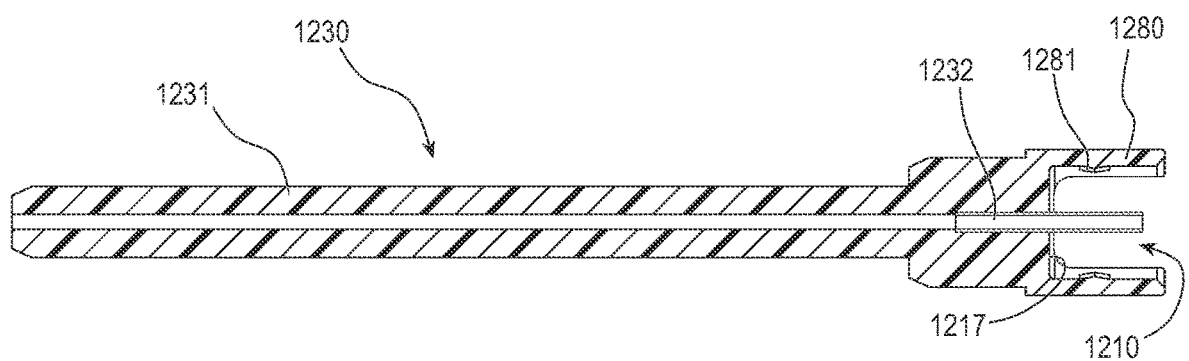
FIG. 32B is a cross-sectional view of the coupling member of FIG. 32A.

FIG. 31 is a cross-sectional view of the access system 1200 in the retracted state. FIG. 32A is a perspective view of an embodiment of a coupling member 1270 that is compatible with the access system 1200. FIG. 32B is a cross-sectional view of the coupling member 1270. The coupling member 1270 includes a reinforcing tube 1232 that extends or projects distally relative to a bottom, inner, recessed, or distally facing surface 1217 of the connector 1202, in manners such as previously discussed.

In other embodiments, the proximal projection 1231 may instead be defined solely by a proximal extension of the reinforcing tube 1232, similar to an arrangement such as that depicted in FIG. 7. Stated otherwise, the reinforcing tube 1232 may define both a distal projection 1213 and the proximal extension 1231.

FIG. 33 is a cross-sectional view of a distal end of the access system 1200, while in the retracted or undeployed state, being advanced toward an embodiment of a closed intravenous catheter system 700 for coupling therewith. FIG. 34 is a cross-sectional view of the distal end of the access system 1200, while in the retracted or undeployed state, coupled with the closed intravenous catheter system 700. In the illustrated embodiment, a distal tip of the reinforcing tube 1232 is advanced through the proximal septum 851, but is proximally spaced from the valve 852 when the access system 1200 and the closed catheter system 700 are coupled together. Advancement of a cannula portion of the access system 1200 through the reinforcing tube 1232, the valve 852, and ultimately the catheter tube 704 can proceed in manners such as previously discussed.

For example, in the illustrated embodiment, the reinforcing tube 1232 is advanced distally through the opening 855 of the retainer 853, then through the opening 854 of the proximal septum 851. These openings 855, 854 are aligned, or are colinear with, the sealable region 856 (and more particularly, the substantially linear needle tract through the sealable region 856). In the illustrated embodiment, once the access system 1200 is fully coupled to the proximal port 809 of the closed intravenous catheter system 700, the distal tip of the reinforcing tube 1232 is positioned at an interior of the proximal septum 851, as shown in FIG. 34. After such coupling, the cannula 1204 can be advanced distally, and the distal tip of the cannula 1204 can emerge from the reinforcing tube 1232 to move substantially rectilinearly through the distal end of the proximal septum 851, then through the valve 852 (including through the sealable region 856 of the valve 856), then through the hub 806, then into and through the catheter tube 704. As discussed elsewhere, the support member 1230 and/or the intrinsic support provided by the medial segment of the cannula 1204 can assist in the successful insertion of the cannula 1204 through the valve 852 without kinking or buckling of the distal segment of the cannula 1204.

In some instances, once the distal tip of the cannula 1204 has passed through the sealable region 856 of the valve 852, the valve 852 may support the cannula 1204 as it is further advanced distally through the hub 806 and the catheter tube 704. For example, the valve 852 can provide lateral support that inhibits lateral deflections of the cannula 1204 in the region of contact between the sealable region 856 and the cannula 1204.

With continued reference to FIG. 34, as previously noted, in various embodiments, the cannula 1204 may resemble any of the disclosed varieties of the cannulas 204, 1004, or 1404 (which is described below). For example, in some embodiments, the cannula 1204 includes a distal segment and a medial segment that resemble any variety of the distal and medial segments 226, 224 and/or 1026, 1024, respectively, discussed above, and/or the distal and medial segments 1426, 1424, respectively, discussed below. While only the distal segment is shown in FIG. 34, the presence and structure of medial segment can be understood from other drawings and disclosures herein.

In some embodiments, the medial segment of the cannula 1204 includes two abutting tubes that are joined by heat-shrink tubing (see, e.g., FIG. 22). The medial tube can be rigid, and may be formed of a metal—for example, the medial tube may comprise a stainless steel hypotube. In other embodiments, the medial segment of the cannula 1204 includes a flexible central tube that extends continuously along the distal and medial segments, but that is encompassed by a rigid tube along the length of the medial segment (see, e.g., FIGS. 56A and 56B). The rigid tube may be formed of metal, such as a stainless steel hypotube. In either instance, the medial segment can have substantial radial strength so as to resist radial compression that might otherwise constrict or close a lumen through the tube. For example, in various embodiments, due to the presence of a rigid tube in the medial segment, the medial segment can have a greater ability to maintain a fluid path that extends through a center of the medial segment in an open state, even under radial forces or stresses on the medial segment that would tend to constrict or close the fluid path if left unopposed.

In certain embodiments of the access system 1200, when the cannula 1204 is in the deployed state, the medial segment of the cannula 1204 fully extends through the valve 852 of the closed intravenous catheter system 700. For example, in some embodiments, either the rigid tube that forms the medial segment or the support cannula that encompasses a flexible inner tube along the length of the medial segment passes through the valve 852 near the end of advancement of the cannula 1204 through the catheter tube 704. Due to the intrinsic rigidity of the rigid tube of the medial segment, the medial segment can prevent inward stresses provided to the cannula 1204 by the valve 852 that result from expansion of the sealable opening 856 from collapsing the medial segment. For example, in certain embodiments that include a flexible central tube positioned within a rigid tube, the rigid tube can resist the compressive forces from the valve 852 to maintain the inner tube in a patent state. Stated otherwise, upon final advancement of the cannula 1204, or when a user is ready to aspirate or draw blood through the cannula 1204, the medial segment of the cannula 1204 can extend throughout an entirety of the sealable region 856 of the valve 852 to prevent the valve 852 from collapsing a flow path through the cannula 1204.

In various embodiments, an outer diameter of the medial segment of the cannula 1204 is the same as or only slightly larger than an outer diameter of the distal segment. For example, in various embodiments, the outer diameter of the medial segment is no greater than 5, 10, or 15 percent larger than the outer diameter of the distal segment. In some embodiments, a medial segment having a diameter that is the same or only slightly larger than the outer diameter of the distal segment may readily follow the distal segment through the valve 852 as the cannula 1204 is advanced distally and/or may pass through the valve 852 without causing damage thereto. In other or further embodiments, by virtue of following the distal segment into and through the valve 852, the medial segment may readily pass through the valve 852 and/or may do so without damaging the valve 852.

Reference is now made to FIGS. 35-53, which are directed to another embodiment of an access system 1300 that may be particularly useful with open base catheter systems. For example, in some instances, the access system 1300 may be particularly well suited for use with open base catheter systems that include an extension set coupled with a catheter assembly, such as the open base catheter system 1100 depicted in FIGS. 24 and 25. As previously discussed with respect to FIGS. 24-27 and 29B, the catheter system 1100 can include a large internal region in which a cannula, when positioned therein, is unsupported as the cannula is advanced distally therethrough. This region of relatively large internal diameter(s) corresponds with the inner cavities of the connected hubs 1180, 1106 (see FIG. 25). With reference to FIG. 36, embodiments of the access system 1300 can include a reinforcement member 1330 that includes a movable reinforcement cannula 1332. The reinforcement cannula 1332 is movable relative to a connector 1302 so as to advanced distally into this unsupported region of the catheter system 1100 and provide lateral support or reinforcement to a cannula 1304 as it is advanced distally through the hubs 1180, 1160 into the catheter tube 1104 of the catheter system 1100.

The cannula 1304 can be of any suitable construction, including those discussed elsewhere herein. For example, in some embodiments, the cannula 1304 includes at least a distal segment and a medial segment formed in manners such as described elsewhere. The medical segment may be intrinsically reinforced so as to resist or prevent kinking or buckling thereat as the cannula 1304 is advanced distally.

Figure 35:
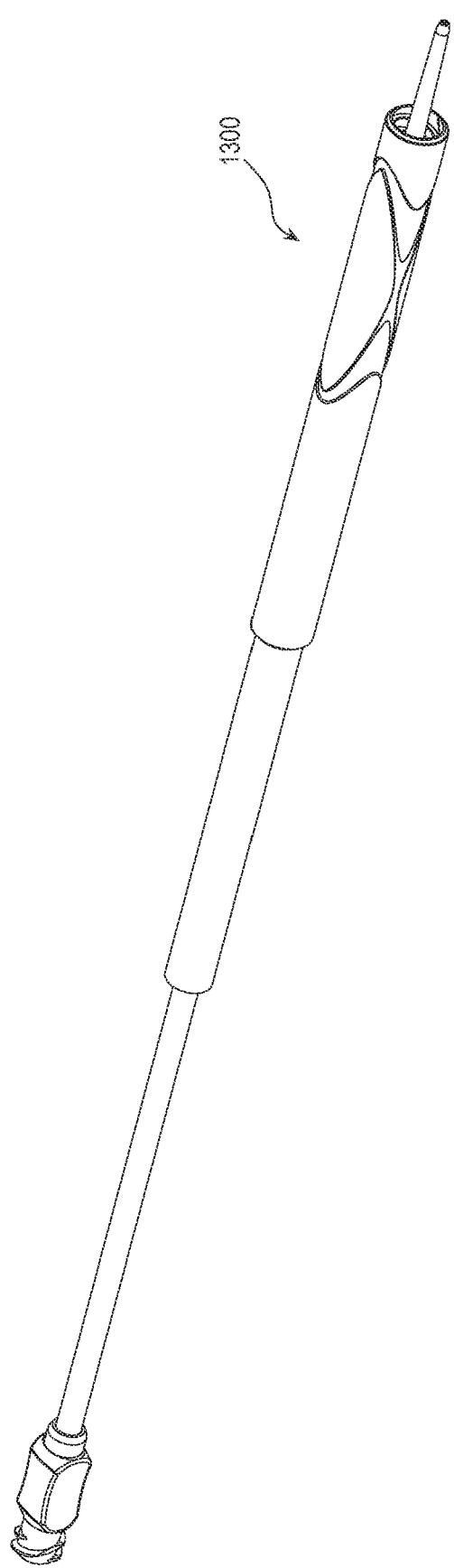
FIG. 35 is a perspective view of another embodiment of an access system configured to be coupled with embodiments of a base catheter system, with the access system being shown in a retracted or undeployed state.
Figure 36:
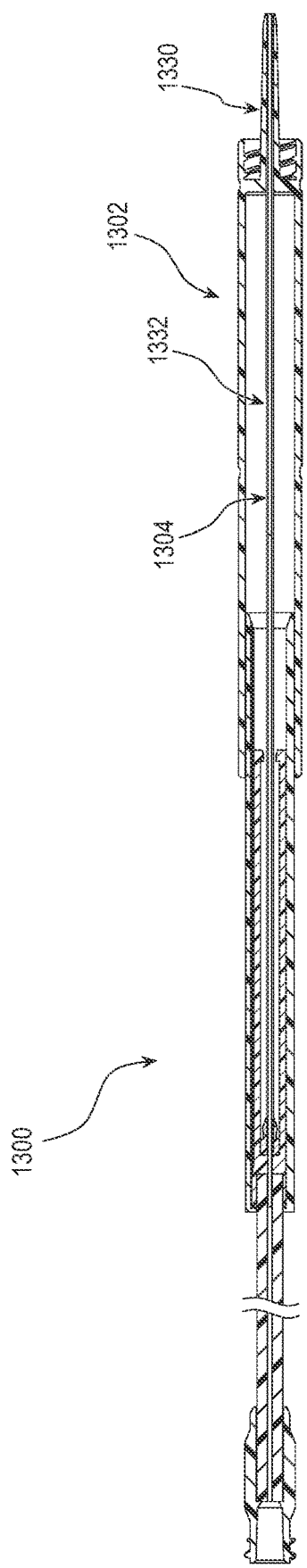
FIG. 36 is a cross-sectional view of the access system of FIG. 35 in the retracted state.

FIG. 35 is a perspective view of the access system 1300 in a retracted or undeployed state. As noted, in some embodiments, the access system 1300 can be particularly well-suited for use with open intravenous catheter systems, and may further be well-suited for use with extension sets coupled with such open intravenous catheter systems. The movable reinforcement tube 1332 can be said to support the cannula 1304 along at least a portion of a length of the extension set, such as the extension set 1150, and/or through a length of a catheter hub to which the extension set is coupled, such as the catheter hub 1106. FIG. 36 is a cross-sectional view of the access system 1300 in the retracted state.

Figure 37A:
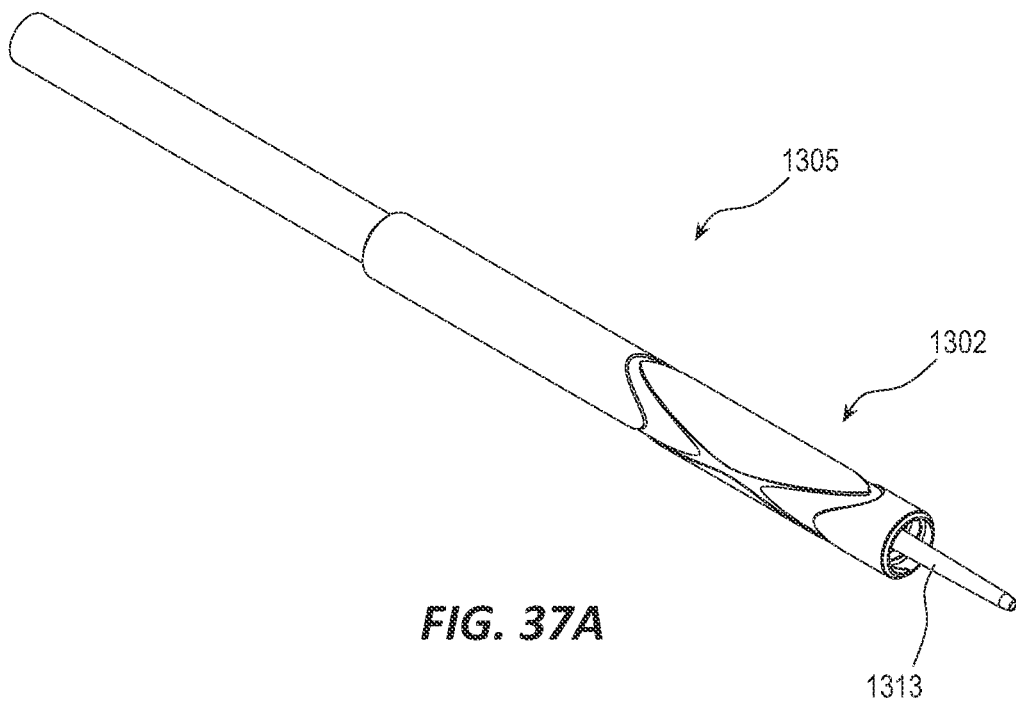
FIG. 37A is a perspective view of an embodiment of a housing that is compatible with the access system of FIG. 35.
Figure 37B:
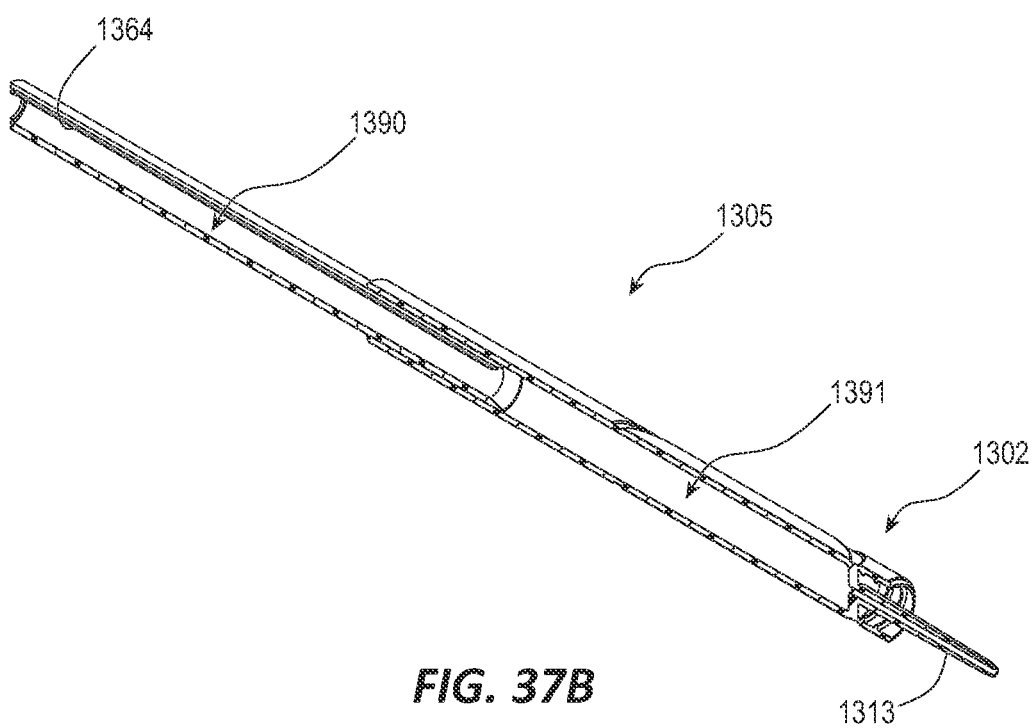
FIG. 37B is a perspective cross-sectional view of the housing of FIG. 37A.

FIG. 37A is a perspective view of an embodiment of the connector 1302, which includes a housing 1305 that is compatible with the access system 1300. FIG. 37B is a perspective cross-sectional view of the housing of FIG. 37A. The housing 1305 can define a proximal chamber 1390 and a distal chamber 1391. The distal chamber 1391 can have a larger inner diameter than does the proximal chamber 1390. As discussed below, the proximal chamber 1390 can be narrower so as to define a restricted region, whereas the distal chamber 1391 can be relatively larger to define an expanded region. In the illustrated embodiment, the proximal chamber 1390 includes a track 1364, similar to the anti-rotational track 1064 discussed previously.

The housing 1305 can include a distal protrusion 1313 similar to like numbered elements above. As discussed further below, the distal protrusion or projection 1313 can cooperate with or support a reinforcing member 1330 (see FIG. 36). The distal projection 1313 can be fixed relative to the connector 1302. For example, the distal projection 1313 may be integrally formed with at least a distal end tube of the housing 1305. The distal projection 1313 may define an inner diameter that is slightly larger than an outer diameter of the reinforcing tube 1332. The reinforcing tube 1332 may be sized to slide through the distal projection 1313. The distal projection 1313 may be viewed as a component of the reinforcing member 1330. For example, the reinforcing member 1330 can include both the distal projection 1313 and the reinforcing cannula 1332. In various embodiments, at least a portion of the reinforcing member 1330 is fixed relative to the housing 1305. In various embodiments, at least a portion of the reinforcing member 1330 is movable relative to the connector housing 1305.

Figure 38A:
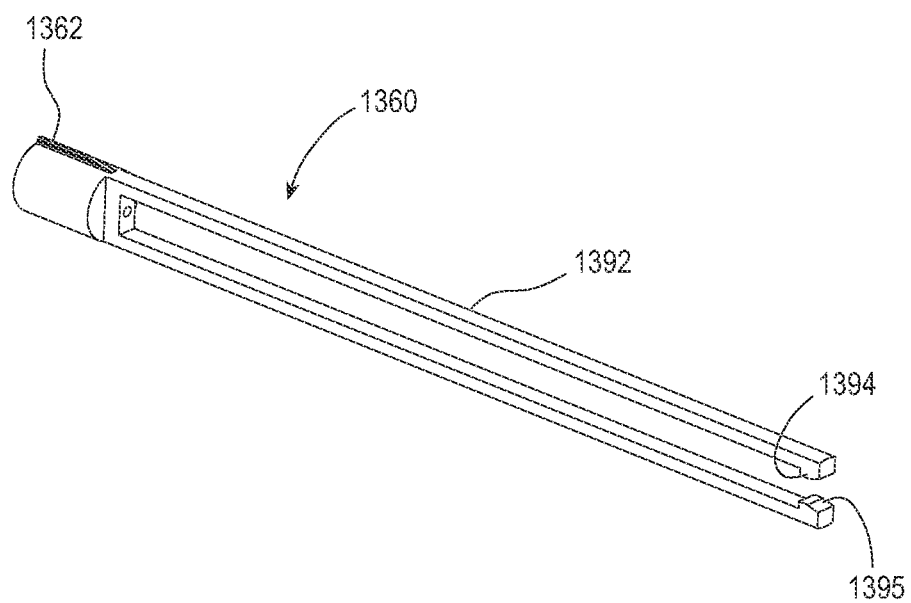
FIG. 38A is a perspective view of an embodiment of a follower that is compatible with the access system of FIG. 35, the follower including a selective engagement feature.
Figure 38B:
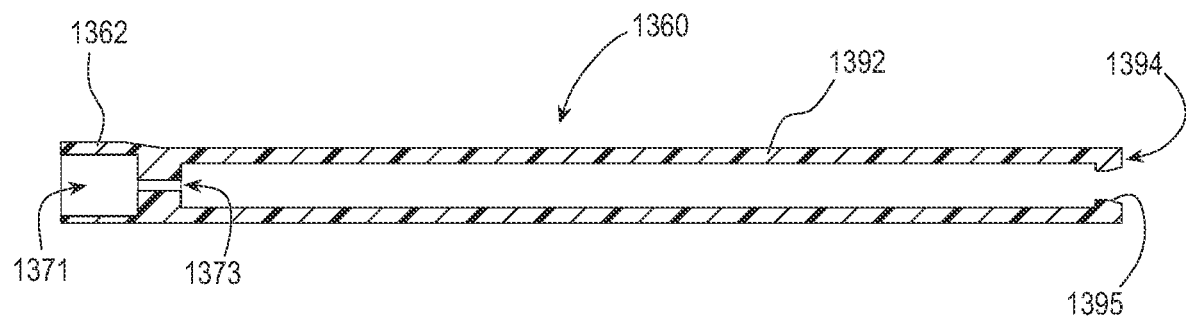
FIG. 38B is a cross-sectional view of the follower of FIG. 38A.

FIG. 38A is a perspective view of an embodiment of a follower 1360 that is compatible with the access system 1300. The follower 1360 can include a selective engagement feature that can engage with or disengage from the reinforcing cannula 1332. FIG. 38B is a cross-sectional view of the follower 1360. The follower 1360 includes a selective engagement feature, by which the follower 1360 can selectively engage and selectively disengage from the reinforcing cannula 1332. In particular, the follower 1360 includes a plurality of engagement arms 1392 having distal ends configured to interface with a catch 1393 attached to the reinforcing cannula 1332 (see FIG. 42). In particular, the engagement arms 1392 can each include an engagement protrusion 1394 that is configured to interface with the catch 1393 in manners such as described below. In the illustrated embodiment, each engagement protrusion 1394 includes an engagement face 1395. The engagement face 1395 may be a ramped or angled surface. Each engagement face 1395 may be angled away from a central longitudinal axis of the follower 1360, in a proximal-to-distal direction.

The follower 1360 can include an anti-rotation protrusion 1362, which can resemble the protrusion 1062 discussed above. The anti-rotation protrusion 1362 may be configured to interface with the track 1364 of the housing 1305 in manners such as previously described. The follower 1360 may further include a proximal cavity 1371 and an opening 1373, which may be similar to the proximal cavity 1071 and the opening 1073 described above.

Figure 39A:
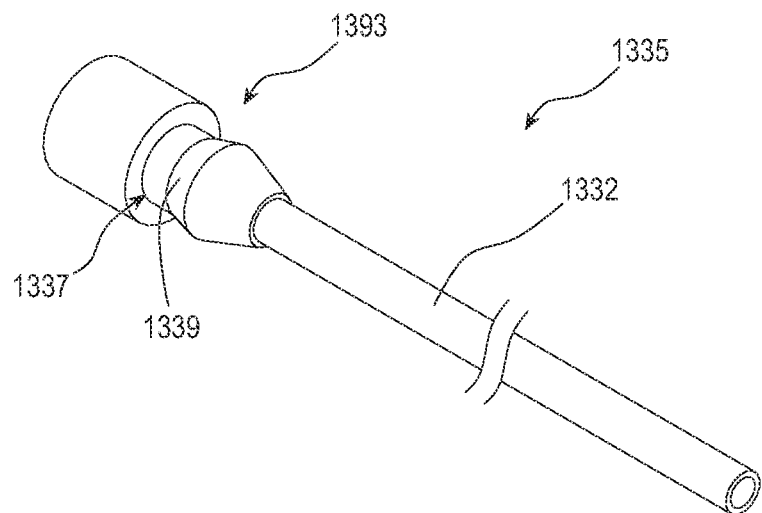
FIG. 39A is a perspective view of an embodiment of a reinforcing tube assembly that includes a reinforcing tube and a catch.
Figure 39B:
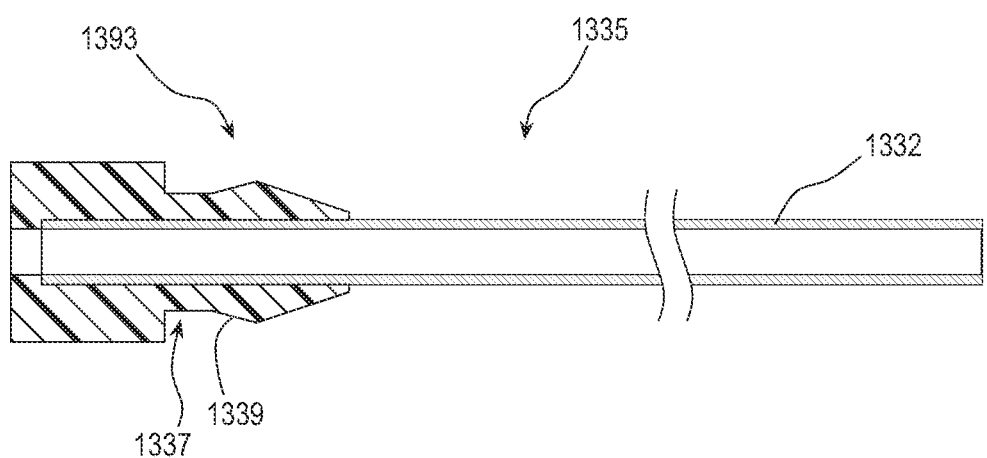
FIG. 39B is a cross-sectional view of the reinforcing tube assembly of FIG. 39A.

FIG. 39A is a perspective view of an embodiment of a reinforcement shuttle 1335 that includes the reinforcing tube 1332 and the catch 1393. FIG. 39B is a cross-sectional view of the reinforcement shuttle 1335.

The catch 1393 can be fixedly secured to a proximal end of the reinforcement tube 1332. The catch 1393 can define a recess 1337 that is sized to receive the engagement protrusions 1394 of the engagement arms 1392. In the illustrated embodiment, the recess 1337 is formed as an annular depression have a cross-sectional profile that is complementary to a profile of each engagement protrusion 1394. The recess 1337 can include an engagement face 1339 that is configured to make contact with the engagement faces 1395 of the engagement protrusions 1394. The engagement face 1339 may be a ramped or angled surface. In particular, the engagement face 1339 can be angled away from a central longitudinal axis of the reinforcement shuttle 1335, in a proximal-to-distal direction. The ramped engagement faces 1339, 1395 of the catch 1393 and the arms 1392 may be referred to as a ramped interface.

Figure 40:
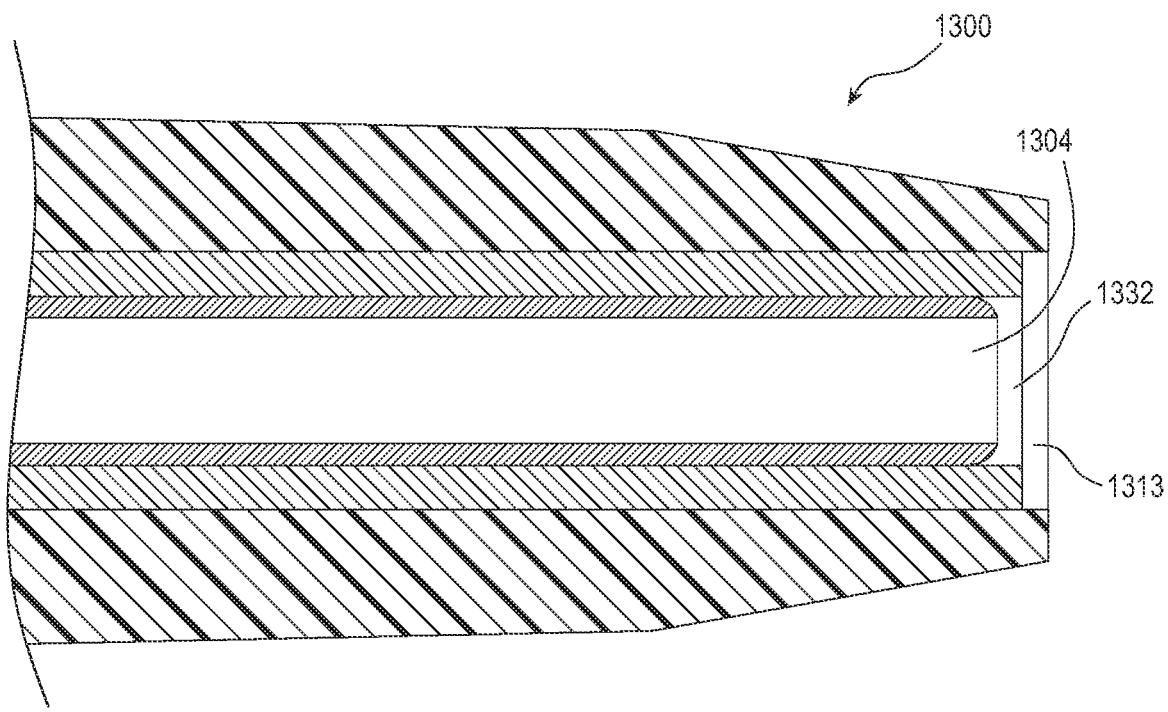
FIG. 40 is a cross-sectional view of a distal end of the access system of FIG. 35 when in the retracted state of FIGS. 35 and 36.

FIG. 40 is a cross-sectional view of a distal end of the access system 1300 when in the retracted state. In the illustrated embodiment, when in this operational state, a distal tip of the cannula 1304 is recessed relative to a distal tip of the reinforcement cannula 1332, which is recessed relative to a distal tip of the distal projection 1313.

Figure 41:
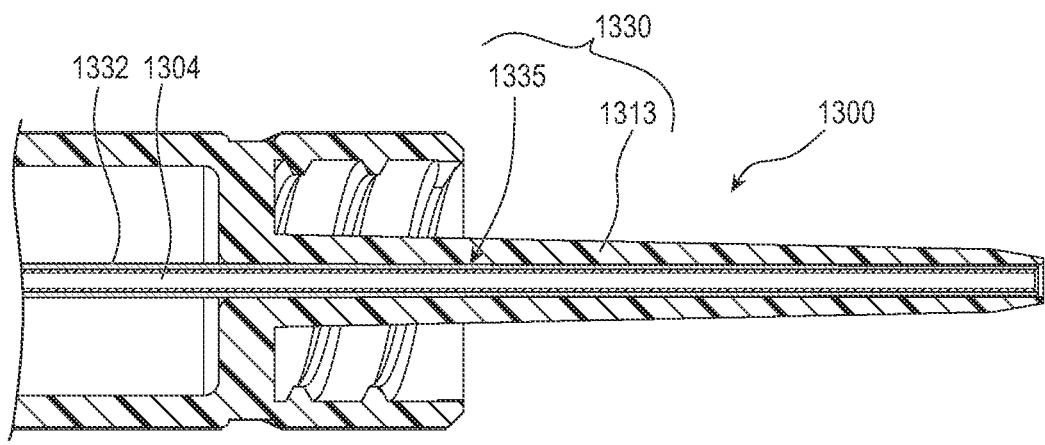
FIG. 41 is a cross-sectional view of a distal region of the access system of FIG. 35 when in the retracted state.

FIG. 41 is a cross-sectional view of a larger distal region of the access system 1300 when in the retracted state. As shown, both the distal projection 1313 and the reinforcement shuttle 1335, which includes the reinforcement cannula 1332, can be components of the reinforcement member 1300. These components cooperate to reinforce the cannula 1304 as it is advanced from the retracted position, in manners such as discussed hereafter.

Figure 42:
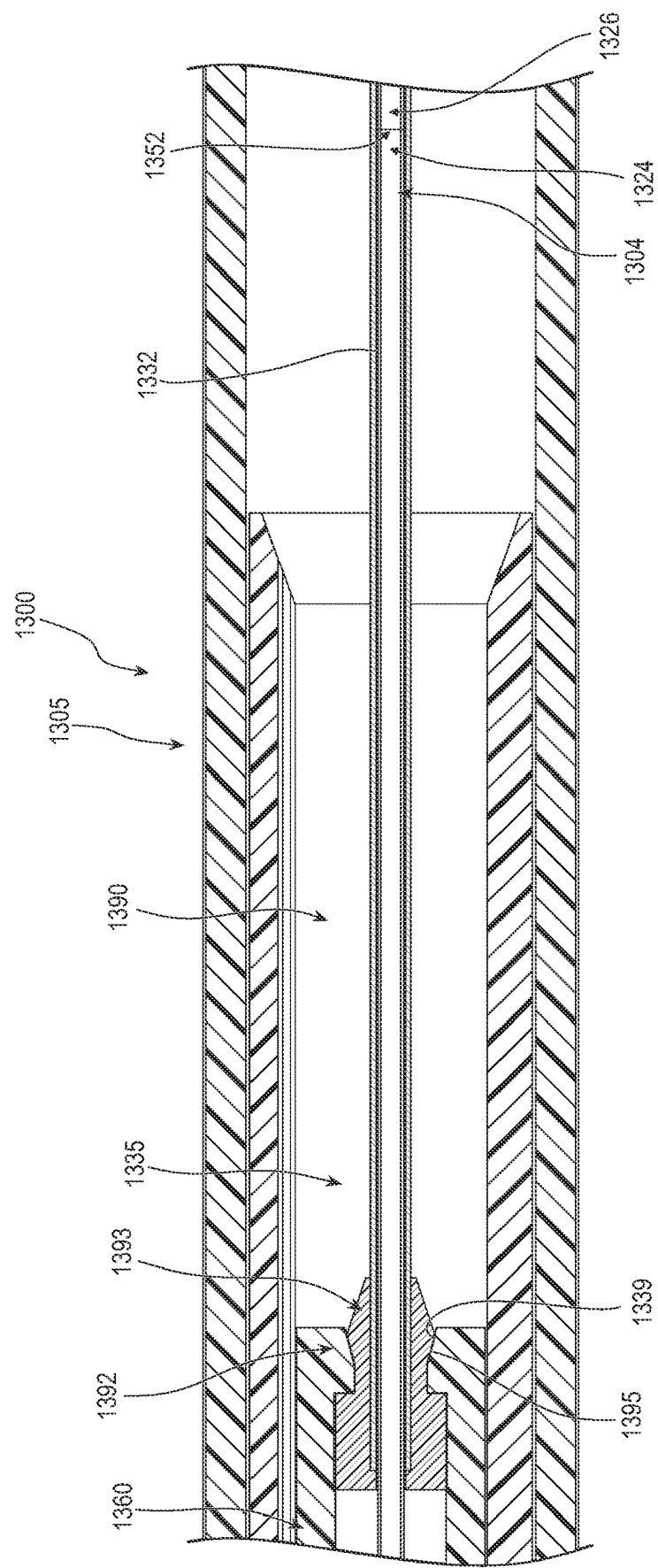
FIG. 42 is a cross-sectional view of an intermediate region of the access system of FIG. 35 when in the retracted state.

FIG. 42 is a cross-sectional view of an intermediate region of the access system 1300 when in the retracted state. As can be seen in this view, the cannula 1304 can include a distal segment 1326 and a medial segment 1324, which can resemble like-named and numbered features discussed elsewhere herein. For example, in some embodiments, the distal segment 1326 can be formed of a polymeric tube (e.g., of polyimide). In some embodiments, the medial segment 1324 includes a proximal extension of the polymeric tube, and further includes a rigid tubular support member (e.g., of metallic construction) that encompasses the polymeric tube. In other embodiments, the medial segment 1324 comprises a rigid tube (e.g., formed of metal) that includes a distal tip that abuts a distal tip of the polymeric tube; the abutting ends of the tubes may be joined in any suitable fashion, such as via an overlying heat shrink tube. Other suitable arrangements are contemplated. The distal and medial segments 1326, 1324 can meet at an interface 1352, which is positioned within the reinforcement tube 1332 in the illustrated retracted state of the access system 1300.

In the illustrated retracted state (also depicted in FIG. 45), the catch 1393 and the distal ends of the arms 1392 of the follower 1360, which are coupled to the catch 1393, can be positioned within the proximal chamber 1390 of the housing 1305. The narrow inner sidewall of the housing 1305 that defines the proximal chamber 1390 can constrain the arms 1392 so as to maintain the arms 1392 in a coupled state with the catch 1393. In particular, the proximal chamber 1390 can be sized to maintain the angled faces 1395, 1339 of the arms 1392 and the catch 1335, respectively, engaged with each other. As further discussed below, this engagement of the angled faces may permit the arms 1392 of the follower 1360 to urge the catch 1393 distally as the cannula 1304, to which the follower 1360 is attached, is advanced distally.

In some embodiments, the arms 1392 may be resiliently biased outwardly, or away from the central longitudinal axis, so as to spring outwardly when no longer constrained within the proximal chamber 1390. In other embodiments, the arms 1392 may be devoid of a bias. The arms 1392 may be sufficiently flexible to be capable of being urged outwardly by the interaction of the angled faces 1395, 1339 when distal advancement of the reinforcement shuttle 1335 is inhibited and when the arms 1392 are not constrained within the proximal chamber 1390, as further discussed below.

Figure 43:
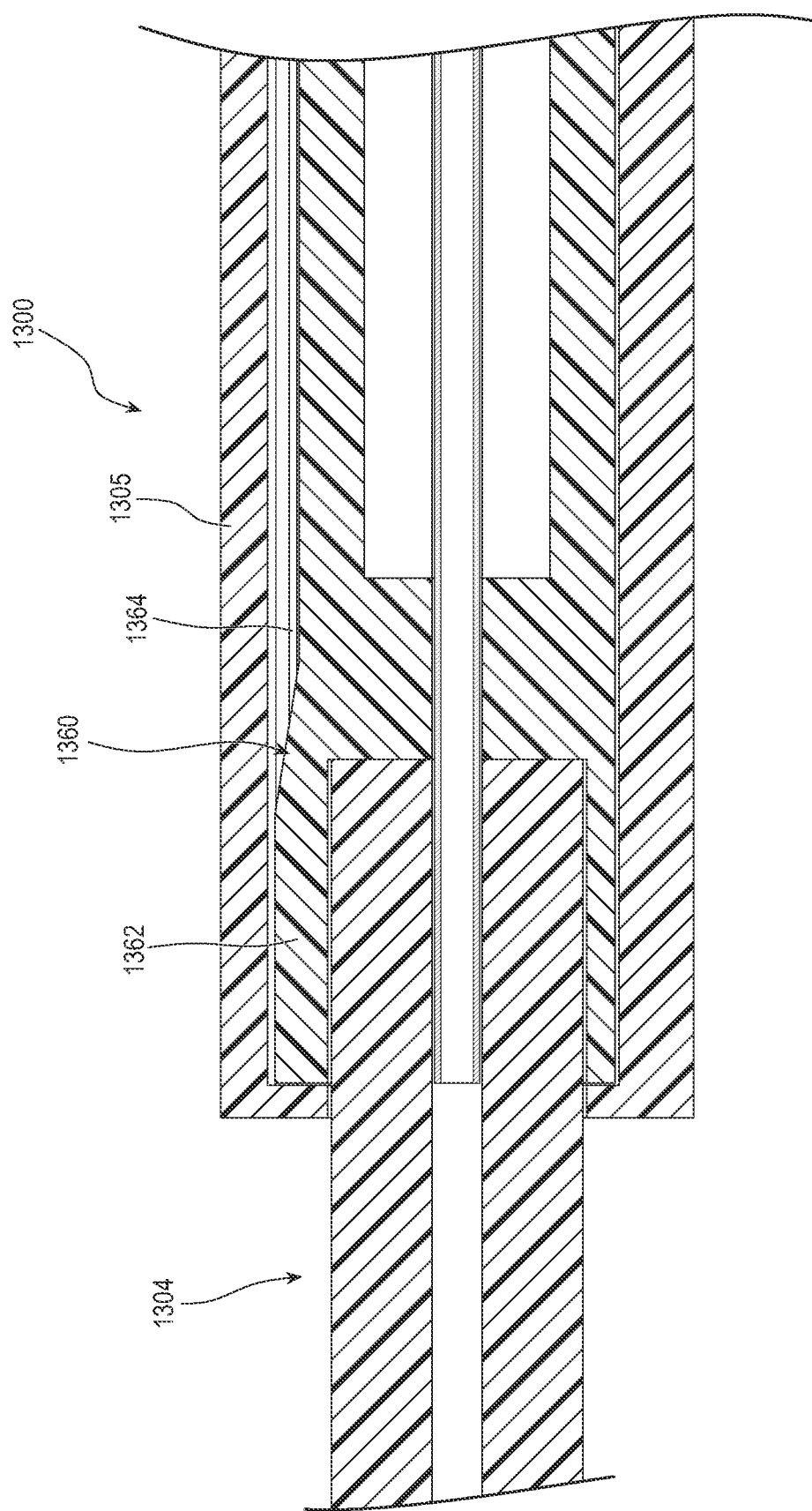
FIG. 43 is a cross-sectional view of a generally proximal portion of the access system of FIG. 35 when in the retracted state.

FIG. 43 is a cross-sectional view of a generally proximal portion of the access system 1300 when in the retracted state. The follower 1360 can be positioned at a proximal end of the housing 1305. The anti-rotation protrusion 1362 can be positioned within the track 1364 of the housing 1305. Further details of the cannula 1304, which can resemble other cannulas previously discussed, are also shown.

Figure 44:
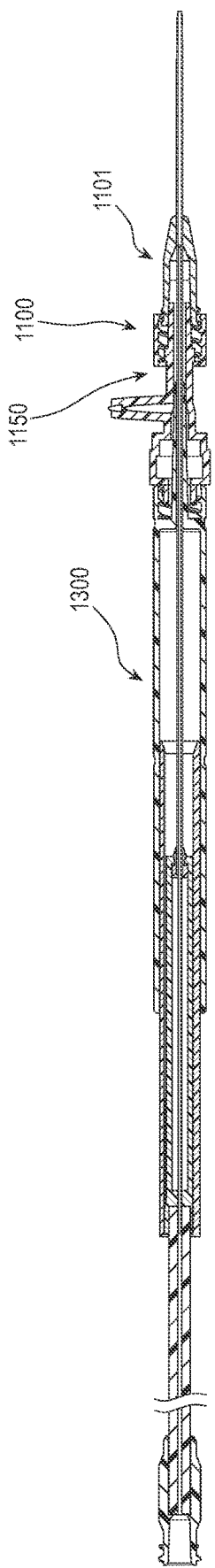
FIG. 44 is a cross-sectional view of the access system of FIG. 35 coupled with an embodiment of a base catheter assembly, such as the base catheter assembly of FIG. 24, while the access system of FIG. 35 is in the retracted state.

FIG. 44 is a cross-sectional view of the access system 1300 coupled with an embodiment of a base catheter assembly 1100 while the access system 1300 is in the retracted state. The base catheter assembly 1100 includes the open intravenous catheter 1101 and the extension set 1150 that is coupled thereto, in manners such as previously described with respect to FIGS. 24 and 25.

Figure 45:
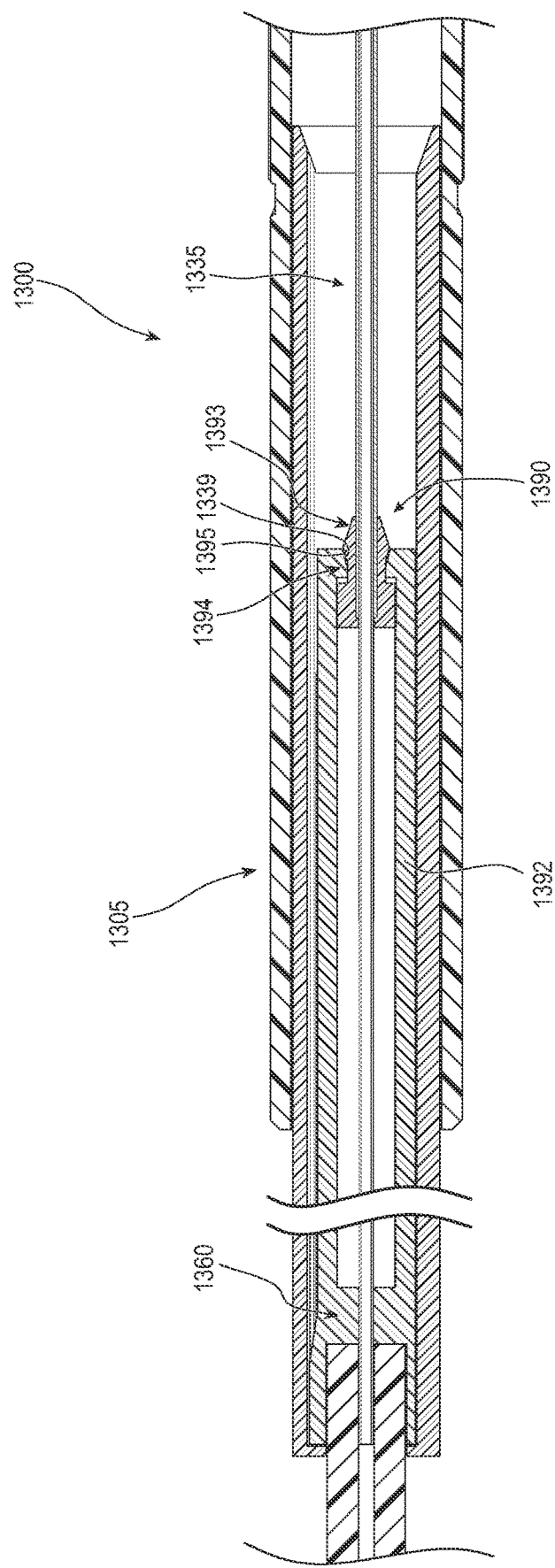
FIG. 45 is a cross-sectional view of a generally intermediate region of the access system of FIG. 35 while in the retracted configuration depicted in FIG. 44.
Figure 46:
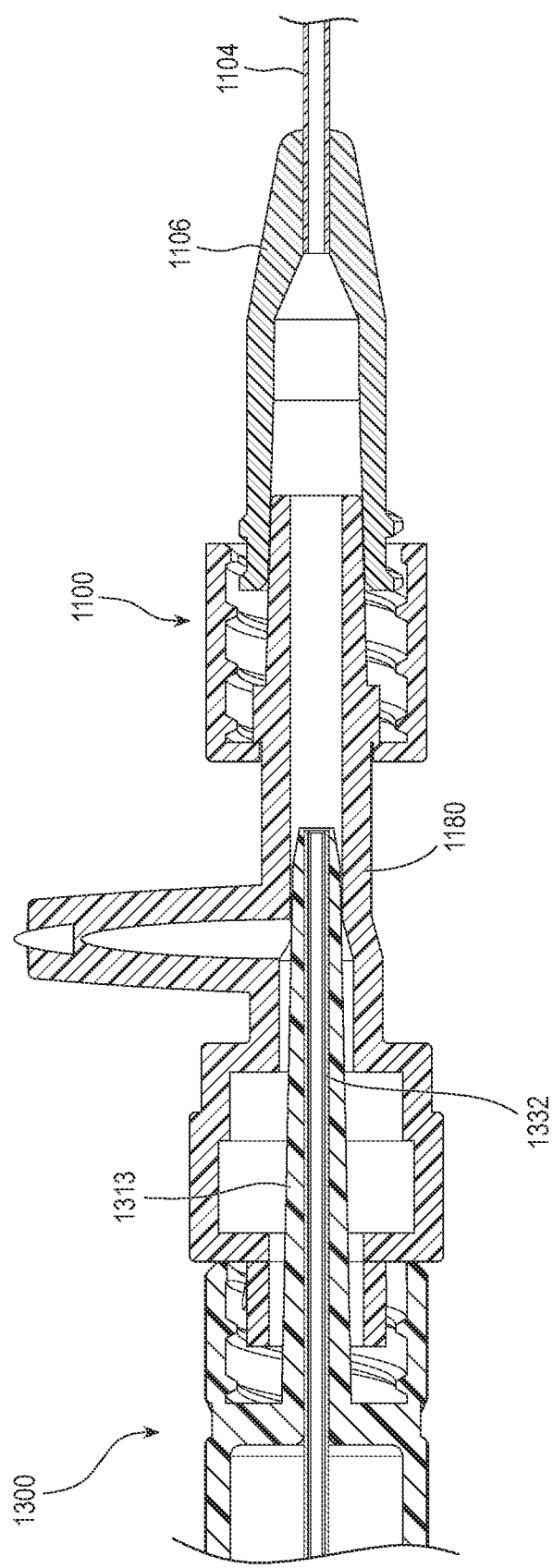
FIG. 46 is a cross-sectional view of a distal portion of the access system of FIG. 35 and a proximal portion of the catheter assembly while the access system is in the retracted configuration depicted in FIG. 44.

FIG. 45 is a cross-sectional view of a generally intermediate region of the access system 1300 while in the coupled and retracted configuration depicted in FIG. 44. FIG. 46 is a cross-sectional view of a distal portion of the access system 1300 while in the coupled and retracted state, which further depicts a proximal portion of the catheter assembly 1100. As shown in FIG. 46, the distal projection 1313 can extend a significant distance within the hub 1180. However, as previously discussed, a larger diameter region extends between the distal tip of the distal projection 1313 and the proximal tip of the catheter tube 1104 within the hubs 1180, 1106. This is the region that is bridged by the reinforcement tube 1332 as the access system 1300 is deployed, as further discussed below.

Figure 47:
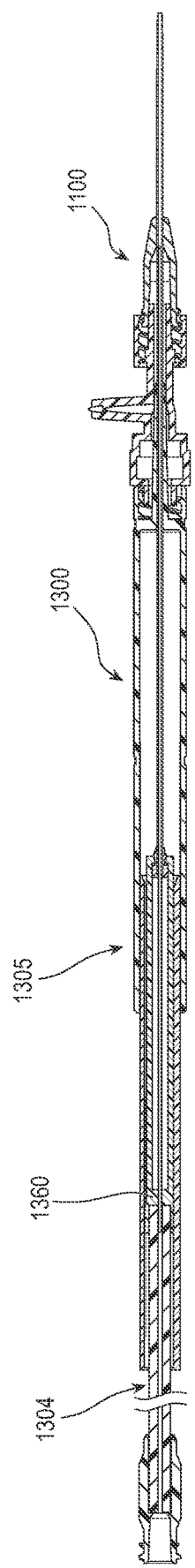
FIG. 47 is a cross-sectional view of the access system of FIG. 35 coupled with the base catheter assembly while in a partially deployed state, or stated otherwise, while in an intermediate stage of deployment.

FIG. 47 is a cross-sectional view of the access system 1300 coupled with the base catheter assembly 1100 while in a partially deployed state, or stated otherwise, while in an intermediate stage or state of deployment. The cannula 1304 has been advanced distally through a first distance, which in turn, has advanced the follower 1360 distally through the housing 1305 by the same distance.

Figure 48:
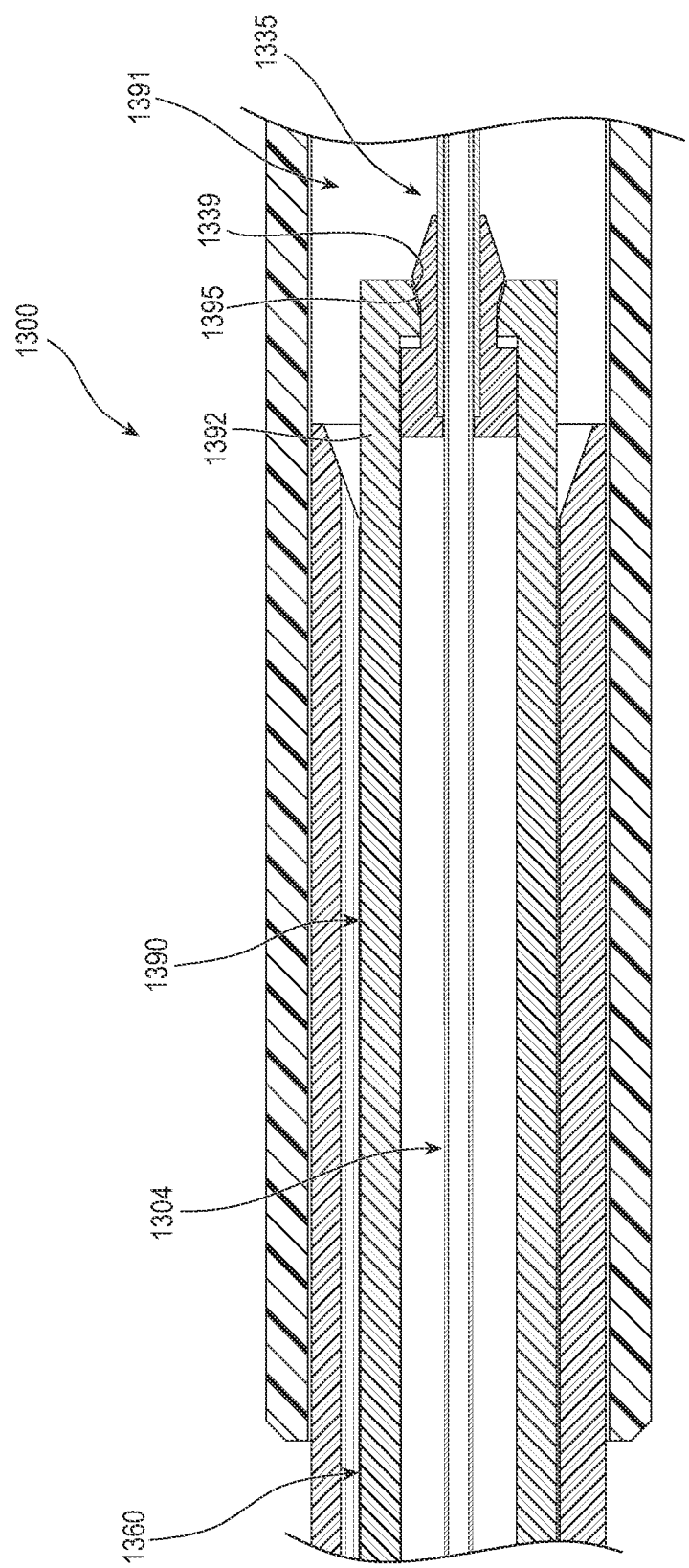
FIG. 48 is a cross-sectional view of an intermediate region of the access system of FIG. 35 while in the intermediate deployment configuration depicted in FIG. 47.

FIG. 48 is a cross-sectional view of an intermediate region of the access system 1300 while in the partially deployed state. In being advanced to the illustrated orientation, the arms 1392 have been and remain in a low-profile state, as constrained by the proximal chamber 1390. This maintains contact between the ramped surfaces 1395, 1339. The ramped surfaces 1395 pushes against the ramped surface 1339 to advance the reinforcement shuttle 1335 distally in unison with distal advancement of the follower 1360 and the cannula 1304.

As shown, the distal ends of the arms 1392 have advanced distally past the end of the proximal chamber 1390 of the housing 1305 and have entered the enlarged cavity of the distal chamber 1391. In the illustrated embodiment, the arms 1392 are not resiliently outwardly biased, and thus do not automatically expand to an enlarged state when no longer constrained in a low-profile orientation. A substantial proximal length of the arms 1392 remains positioned within the proximal chamber 1390 in the constrained state, such that the distal tips of the arms 1392 will generally remain in the low-profile state, even when in the enlarged distal chamber 1391, unless and until they are urged outwardly. Stated otherwise, the distal ends of the arms 1392 are at a position within the distal chamber 1391 at which they may be allowed to be urged radially our laterally outwardly to an expanded profile.

Figure 49:
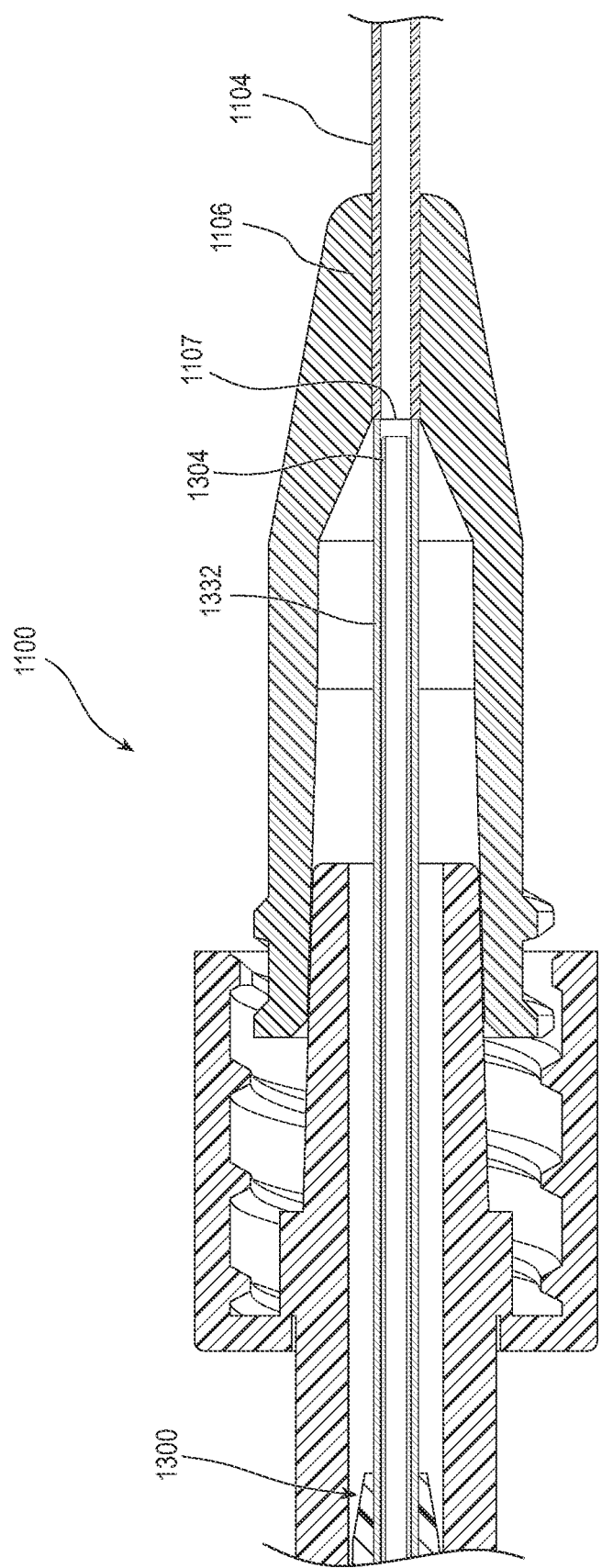
FIG. 49 is a cross-sectional view of a distal end of the access system of FIG. 35 and a proximal portion of the base catheter assembly while the access system is in the intermediate deployment configuration depicted in FIG. 47.

FIG. 49 is a cross-sectional view of a distal end of the access system 1300 and a proximal portion of the base catheter assembly 1100 while the access system 1300 is in the partially deployed state. At this point, a distal tip of the reinforcement tube 1332 has come into contact with the proximal tip 1107 of the catheter tube 1104. This contact can prevent further distal advancement of the reinforcement tube 1332. In the illustrated configuration, the distal end of the cannula 1304 remains within the reinforcement tube 1332 until there is relative movement between the follower 1360 and the reinforcement shuttle 1335 (FIG. 48).

Figure 50:
FIG. 50 is a cross-sectional view of the access system of FIG. 35 coupled with the base catheter assembly while in a fully deployed state.
Figure 51:
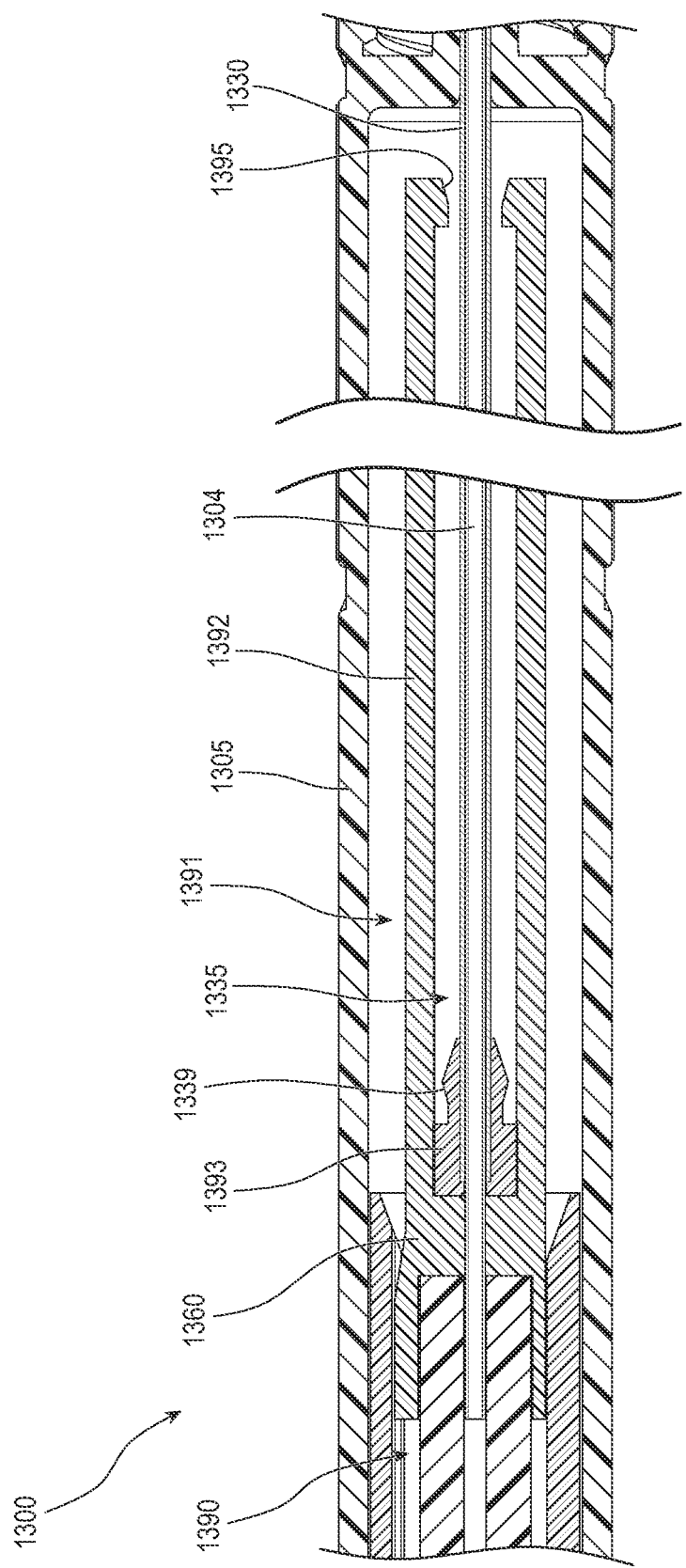
FIG. 51 is a cross-sectional view of an intermediate region of the access system of FIG. 35 while in the fully deployed state depicted in FIG. 50.

FIG. 50 is a cross-sectional view of the access system 1300 coupled with the base catheter assembly 1100 while in fully deployed state. FIG. 51 is a cross-sectional view of an intermediate region of the access system 1300 while in the fully deployed state. In reaching this state, the reinforcement shuttle 1335 remains in the same configuration depicted in FIGS. 47-49. That is, the distal tip of the reinforcement tube 1330 remains abutted against the proximal tip 1107 of the catheter tube1104 (FIG. 49). Note that in other embodiments, the reinforcement tube 1330 may additionally or alternatively be sized to abut against an inner surface of the catheter hub 1106 (FIG. 49). As the cannula 1304 is advanced distally relative to the orientation shown in FIGS. 47-49, the follower 1360 moves distally in unison with the cannula 1304, to which it is attached. The reinforcement tube 1104 and the catch 1393 that is attached thereto remain in a fixed position relative to the housing 1305 due to interference between the reinforcement cannula 1332 and the catheter tube 1104. The ramped or angled surfaces 1395 of the arms 1392 press against the ramped or angled surface 1339 of the immobilized catch 1393. The angled surfaces 1395 interact with the angled surface 1339 to urge the distal ends of the arms 1392 outwardly. The distal chamber 1391 of the housing 1305 provides sufficient clearance to permit the deflected ends of the arms 1392 to pass over the catch 1393 and resiliently return to the straightened state shown in FIG. 51. As the cannula 1304 is further advanced distally, the follower 1360 moves in unison with the cannula 1304 and the arms 1392 of the follower 1360 pass over or by or beside the outer surface of the catch 1393.

In various embodiments, various parameters may be adjusted to permit the arms 1392 to disengage from and move distally relative to the catch 1393 in manners such as just described. For example, in some embodiments, a stiffness of the arms 1392 may be selected to ensure that disengagement only occurs once threshold level of resistance to distal movement of the reinforcement tube 1332 is experienced. A relative orientation of the proximal and distal chambers 1390, 1391 of the housing 1305 may also or alternatively be adjusted. In various embodiments, the access system 1300 may be configured for use with a variety of different base catheter systems (with and/or without extension sets) that define a variety of different lengths through which the reinforcement tube 1332 passes before encountering resistance to forward advancement. Certain embodiments may permit the arms 1392 to remain engaged with the catch 1393 until resistance is met at any of these various lengths and to thereafter disengage from the catch 1393.

Figure 52:
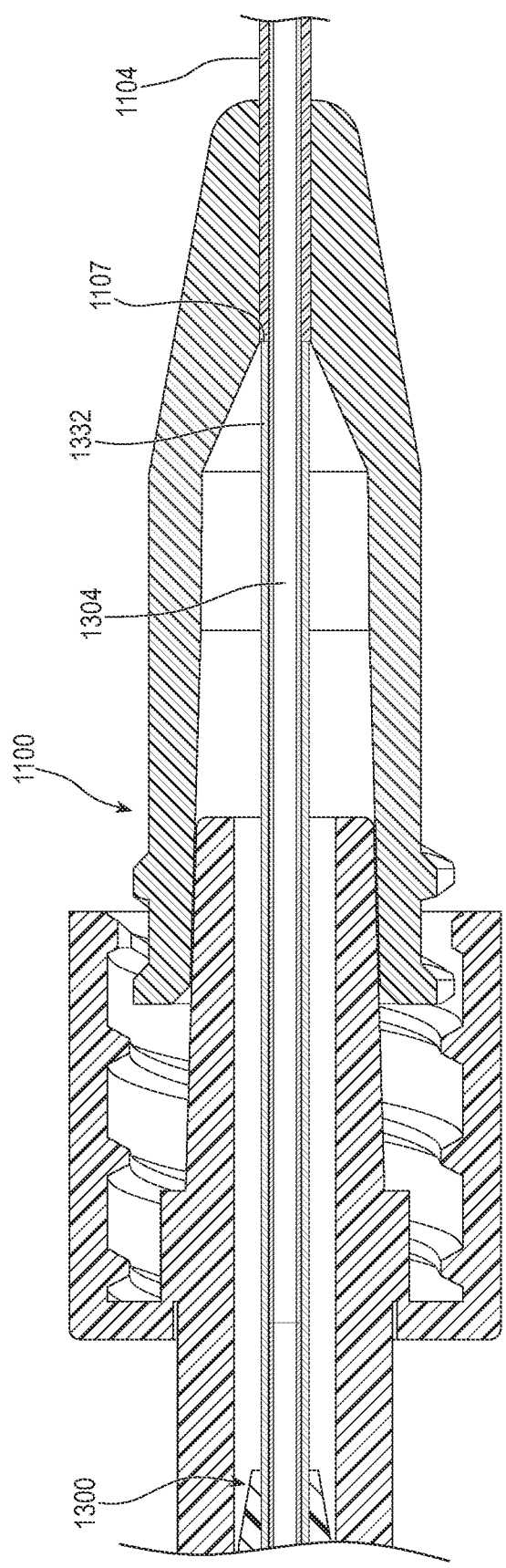
FIG. 52 is a cross-sectional view of a generally distal portion of the access system of FIG. 35 and a proximal portion of the base catheter assembly while the access system is in the fully deployed state depicted in FIG. 50.

FIG. 52 is a cross-sectional view of a generally distal portion of the access system 1300 and a proximal portion of the base catheter assembly 1100 while the access system is in the fully deployed state. As shown, the distal tip of the reinforcement cannula 1332 remains engaged with and immobilized by the proximal tip 1107 of the catheter tube 1104 throughout distal advancement of the cannula 1304 past the intermediate position depicted in FIGS. 47-49. The cannula 1304 passes through the immobilized reinforcement cannula 1332 and is reinforced thereby in the event that resistance to distal movement of the cannula 1304 is encountered, such as at a bend or kink in the catheter tube 1304.

Figure 53:
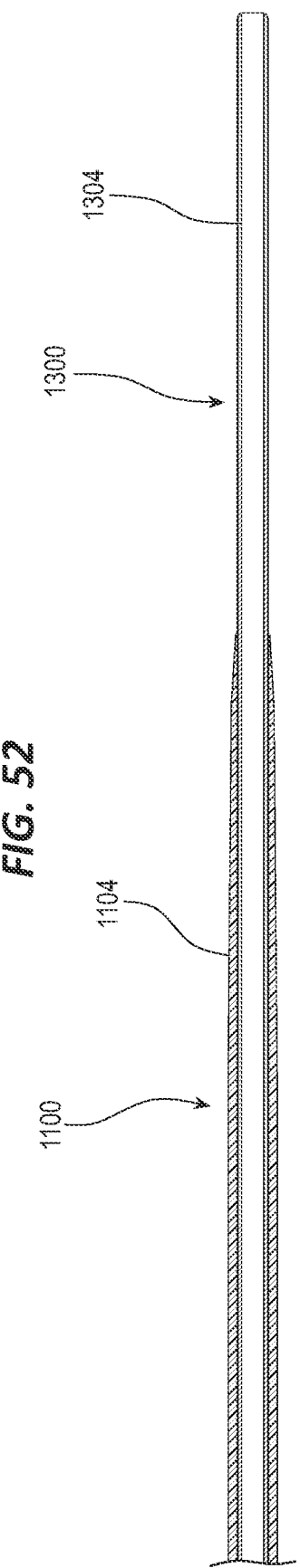
FIG. 53 is a cross-sectional view of distal ends of the access system of FIG. 35 and of the base catheter assembly while the access system is in the fully deployed state depicted in FIG. 50.

FIG. 53 is a cross-sectional view of distal ends of the access system 1300 and the base catheter assembly 1100 while the access system 1300 is in the fully deployed state. In the illustrated embodiment, the cannula 1304 extends past the distal tip of the catheter tube 1104.

Figure 54:
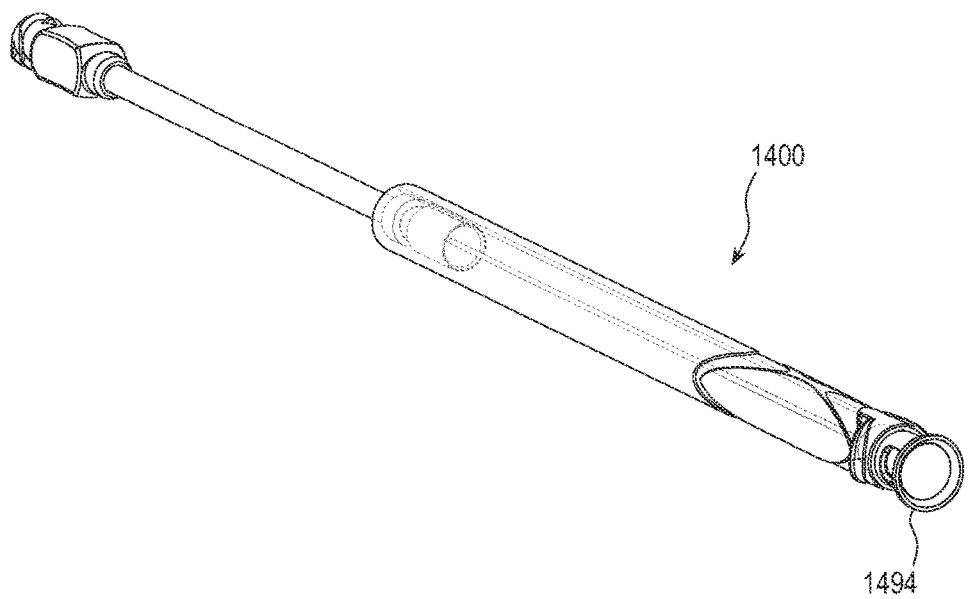
FIG. 54 is a perspective view of another embodiment of an access system in a retracted state.
Figure 55:
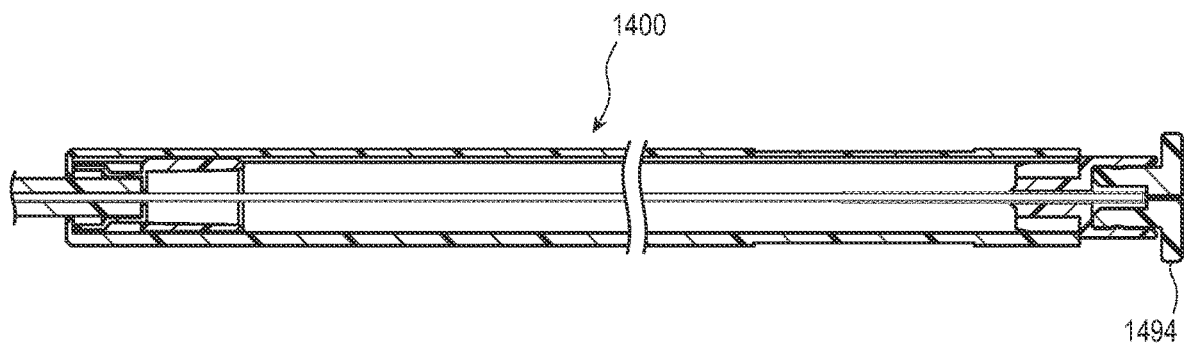
FIG. 55 is a cross-sectional view of the access system of FIG. 54 in the retracted state.

FIG. 54 is a perspective view of another embodiment of an access system 1400, and FIG. 55 is a cross-sectional view of the access system 1400. The access system 1400 is shown in both drawings in a retracted state. The access system 1400 includes a removable sterility cap 1494 that is coupled to a connector 1402. The cap 1494 can be included with the packaged access system 1400 and removed prior to use. The illustrated connector 1402 includes a snap-fit arrangement, such as previously disclosed, for example, with respect to the access system 1200.

The access system 1400 may resemble the access system 1200 in many respects, and may be particularly suitable for use with a closed intravenous catheter system. As discussed above, the cannula 1204 of the embodiment of the access system 1200 illustrated in FIGS. 30-34 includes two abutting tubes that are joined by heat-shrink tubing. However, other cannula configurations are disclosed with respect to the access system 1200, including a cannula that includes a continuous polymeric tube and a support tube that encompasses at least an intermediate region of the polymeric tube. The cannula 1204 of the access system 1400 is of the latter configuration.

Figure 56B:
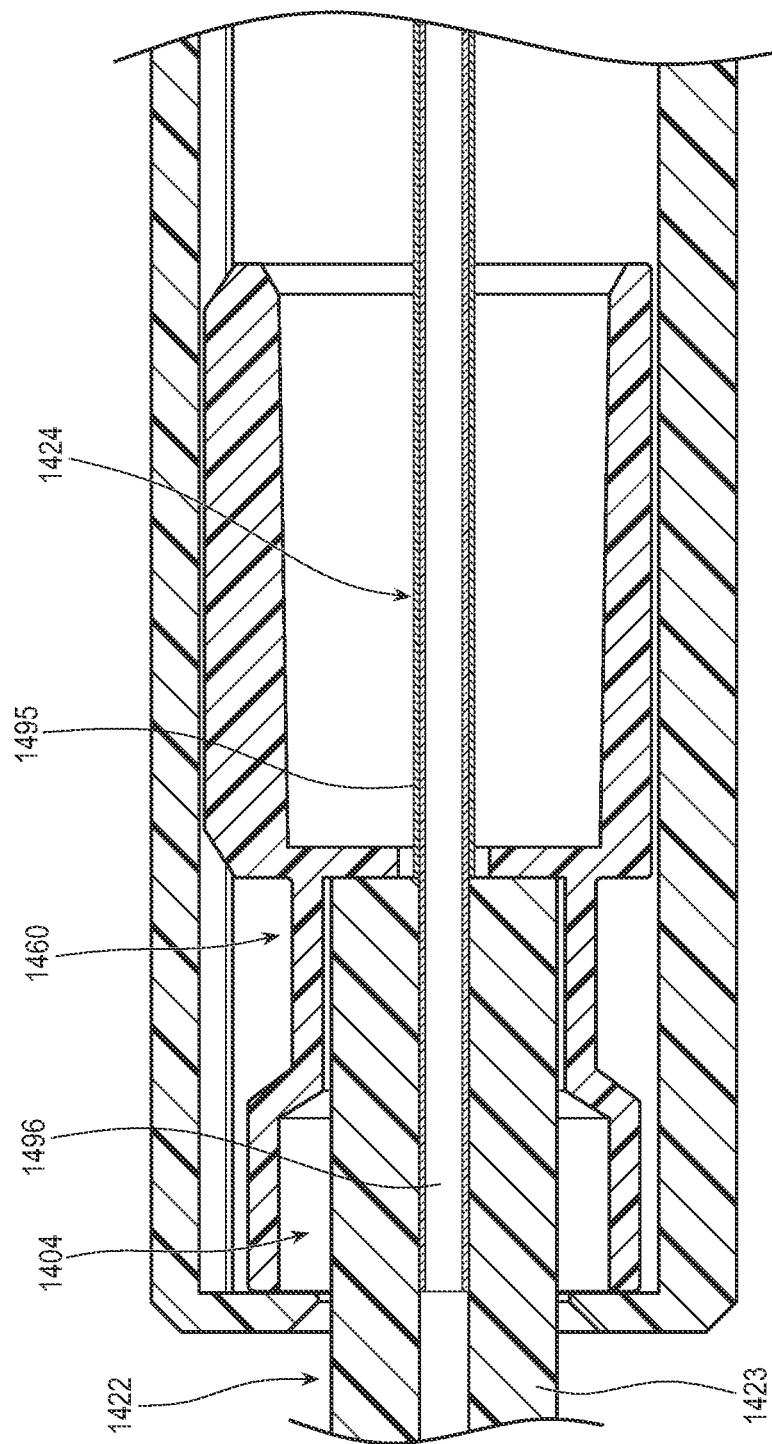
FIG. 56B is an enlarged cross-sectional view of a proximal region of the access system of FIG. 54 in the retracted state.

With reference to FIGS. 56A and 56B, the cannula 1404 can include a proximal segment 1422, a medial segment 1424, and a distal segment 1426. The cannula 1404 includes a central tube 1496 that defines the distal segment 1426. The central tube 1496 extends continuously through the medial segment 1424. A proximal end of the central tube 1496 is positioned in a portion of the proximal segment 1422. The proximal segment 1422 further includes a proximal tube 1422 of any suitable form, such as described previously herein. The central tube 1496 may be coupled with the proximal tube 1422 in any suitable manner, such as by a press fit, adhesive, etc. At least the proximal tube 1422 may be fixedly secured to a follower 1460.

The central tube 1496 may be formed of any suitable material, such as disclosed with respect to other embodiments (e.g., a polymeric material). The central tube 1496 may be flexible. Embodiments of the central tube 1496 can be laterally flexible while having sufficient columnar or axial strength or rigidity to navigate or negotiate tortuous paths through a catheter tube and/or sufficient radial strength to remain patent when within such tortuous paths. The medial segment 1424 can further include a support tube 1495 that encompasses, encircles, sheathes, covers, overlays, etc. an intermediate portion of the central tube 1496. The support tube 1495 may be relatively rigid, as previously discussed. In some embodiments, the support tube 1495 may be metallic, such as a stainless steel hypotube. In some embodiments, the support tube 1495 is fixedly secured to at least a proximal end of the central tube 1496. In some embodiments, the support tube 1495 is adhered or otherwise secured to the central tube 1496 only at a proximal end of the support tube 1495. In other embodiments, the support tube 1495 may be adhered or otherwise secured to the central tube 1496 along substantially an entire length of the support tube 1495. Other arrangements are contemplated.

The support tube 1495 may have an inner diameter that is only slightly, narrowly, marginally, or minimally larger than; is approximately the same as; conforms or substantially conforms with; and/or substantially inhibits, limits, and/or prevents lateral movements of an outer diameter of the central tube 1496. The support tube 1495 can be in a fixed longitudinal relationship with the central tube 1496 so as to move in unison therewith, while preventing lateral movement of the central tube 1496 within a lumen of the support tube 1495 that otherwise would bend, kink, and/or buckle the central tube 1496. In various embodiments, the inner diameter of the support tube 1495 is no greater than 5, 10, 15, 20, 25, or 30 percent larger than the outer diameter of the central tube 1496.

With reference to FIG. 56A, a distal tip or distal edge of the support tube 1495 can correspond to a distal terminus 1450 of the medial segment 1424. Although the central tube 1496 may extend continuously through the distal terminus 1450, the medial and distal segments 1424, 1426 may still be said to meet at an interface 1452 at the distal terminus 1450 of the medial segment 1424.

As with other embodiments disclosed herein, in some embodiments, the interface 1452 may be positioned within a reinforcement tube 1432 when the cannula 1404 is in the retracted state, as shown in FIG. 56A. As the cannula is advanced distally, the support tube 1495 moves in tandem with the central tube 1496 that it encompasses and slides distally within the reinforcement tube 1432.

In some instances, the access system 1400 can be particularly well suited for use with closed catheter systems. The access system 1400 may be coupled and used with the closed catheter system 700 in a manner such as described above with respect to the access system 1200 in FIGS. 33 and 34.

Figure 57:
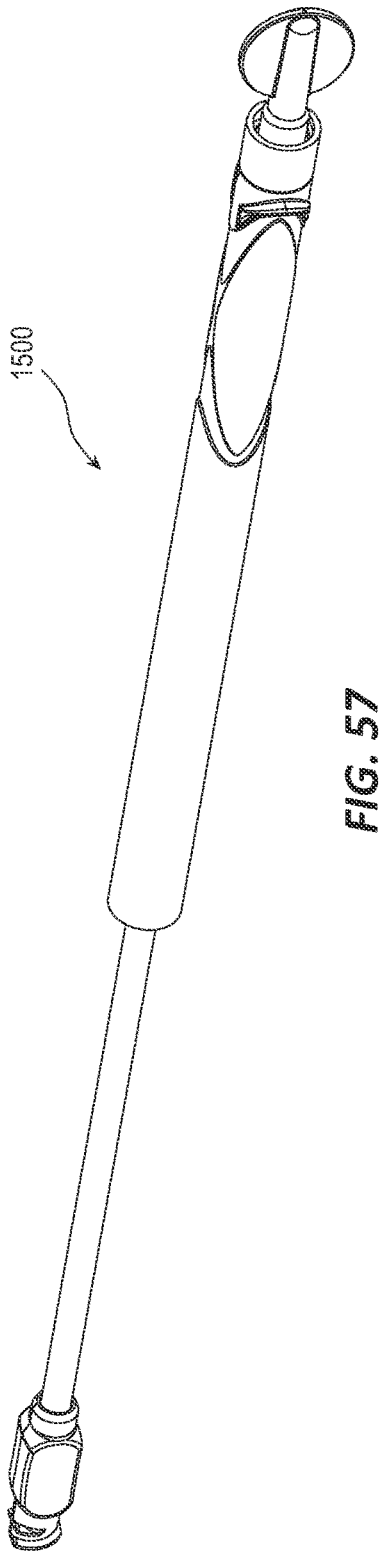
FIG. 57 is a perspective view of another embodiment of an access system in a retracted state.
Figure 58:
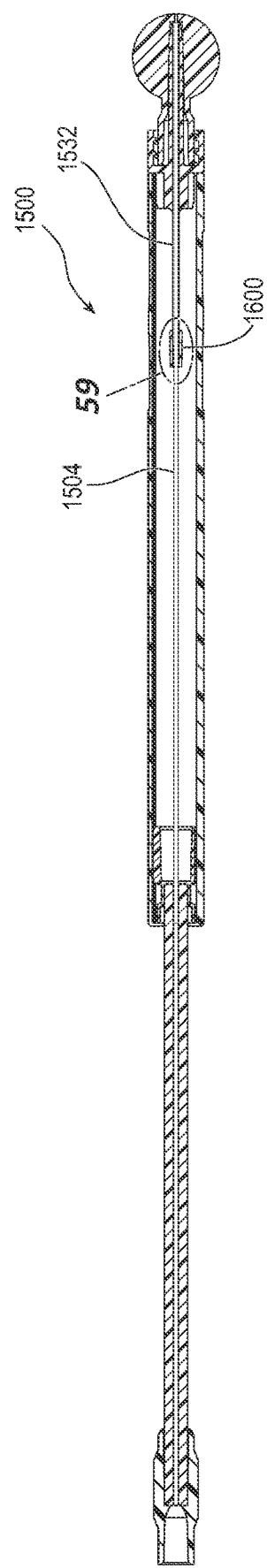
FIG. 58 is a cross-sectional view of the access system of FIG. 57.

FIGS. 57 and 58 depict another embodiment of an access system 1500. In some embodiments, the access system 1500 can be particularly well suited for use with an open catheter system, whether with or without an extension set. The access system 1500 can include a cannula 1504 that is substantially the same as the cannula 1404 just discussed with respect to the access system 1400. In particular, the cannula 1404 can include a central tube and a support member that encompasses the central tube. Other arrangements for the cannula 1504, including those discussed elsewhere herein, are also contemplated.

The access system 1500 can further include a sealing member 1600 coupled with a reinforcement tube 1532 and the cannula 1504. An open catheter system may not include a sealing member or valve that could seal against the cannula 1504 during use. The sealing member 1600 can prevent blood that might pass proximally through an annular space between the reinforcement tube 1532 and the cannula 1504 from egressing from a proximal end of the reinforcement tube 1532 and into a housing of the access system 1500.

Figure 59:
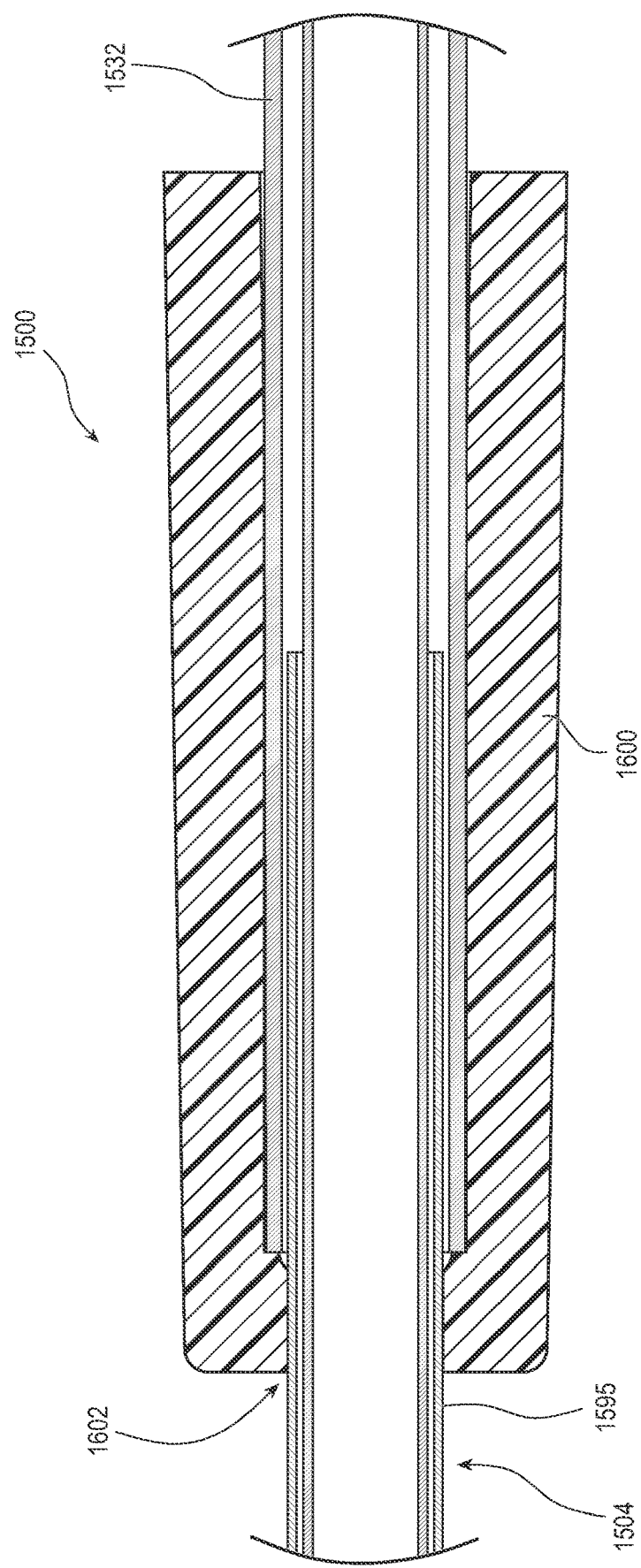
FIG. 59 is an enlarged cross-sectional view of the access system of FIG. 57 taken along the view line 59 in FIG. 58 in which an embodiment of a sealing member positioned at a proximal end of a reinforcement tube is shown.

FIG. 59 provides a more detailed view of in internal portion of the access assembly 1500 that includes the sealing member 1600. The sealing member 1600 can be fixedly secured to a proximal end of the reinforcement tube 1532. The proximal end of the sealing member can include a proximal opening 1602 through which a support tube 1595 of the cannula 1504 passes. The sealing member 1600 can form a static seal with the reinforcement tube 1532 and can form a dynamic seal with the support tube 1595. Stated otherwise, the sealing member 1600 can be in a fixed relation relative to the reinforcement tube 1532, yet can permit movement of the support tube 1595 relative thereto, while the sealing member 1600 maintains a fluid tight seal with each of the reinforcement tube 1532 and the support tube 1595. The sealing member 1600 can prevent blood from egressing from the support tube 1595 and through the proximal opening 1602.

Figure 60:
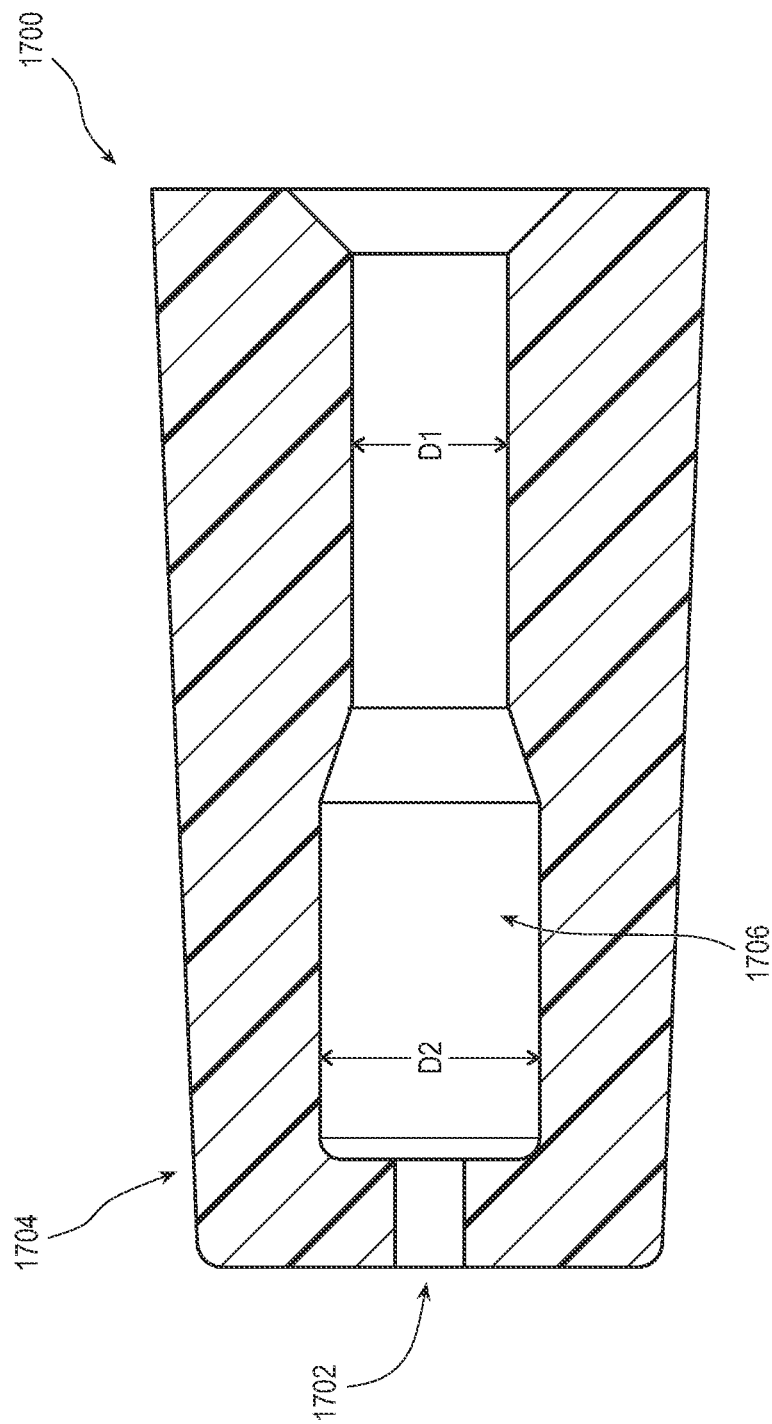
FIG. 60 is a cross-sectional view of another embodiment of a sealing member compatible with the access system of FIG. 57.

FIG. 60 depicts another embodiment of a sealing member 1700, which can resemble the sealing member 1600 in many respects. The sealing member 1700 includes a proximal opening 1702 and a strain-relief region 1704 at a proximal end of the sealing member 1700. In particular, a distal end of an internal cavity 1706 defined by the sealing member 1700 can have a reduced diameter D1 at which the sealing member 1700 tightly grips the reinforcing member 1532 and forms a static, fluid-tight seal therewith. A proximal end of the internal cavity 1704 can have an undercut or expanded region defining an expanded diameter D2. In the expanded proximal region, the sealing member 1700 may be recessed or spaced from an external surface of the reinforcement member 1532 when the access system 1500 is fully assembled. This can, in some instances, permit readier movement of the support tube 1595 through the proximal end of the sealing member 1700 as the support tube 1595 is moved through the proximal opening 1702, thus maintaining a secure, dynamic, fluid-tight seal between the sealing member 1700 and the support tube 1595. The expanded diameter can permit readier flexion of the proximal end of the sealing member 1700.

Figure 61:
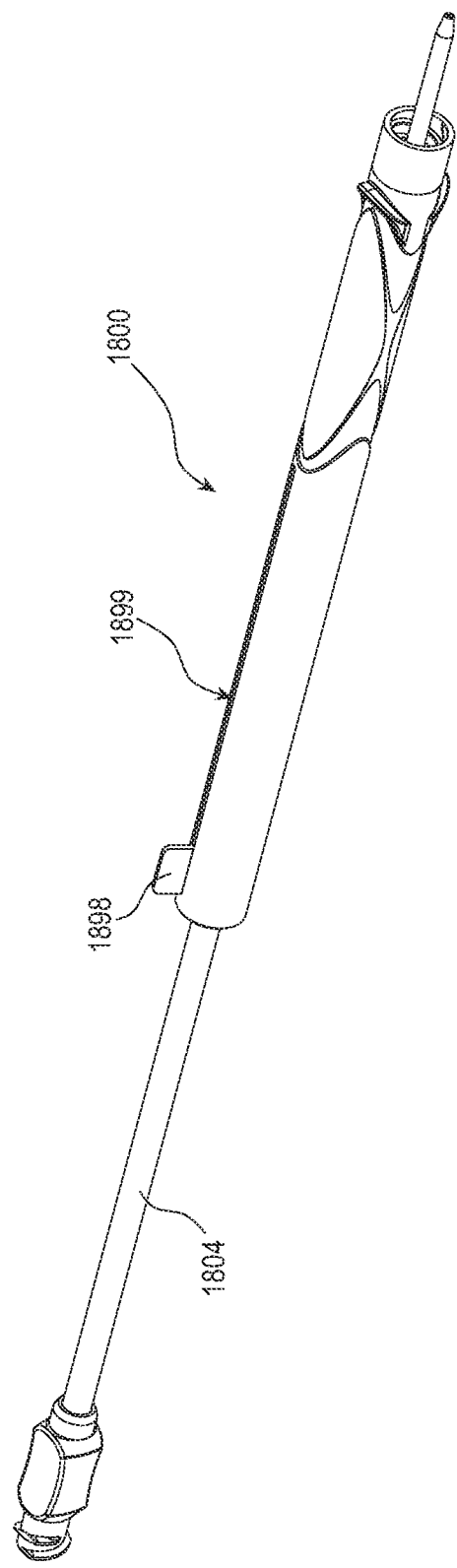
FIG. 61 is a perspective view of another embodiment of an access system in a retracted state.
Figure 62:
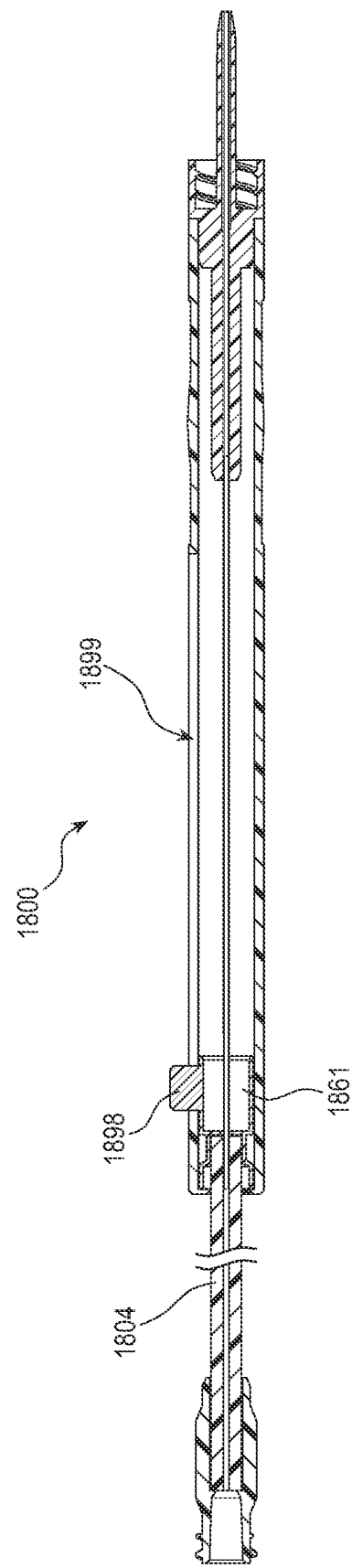
FIG. 62 is a cross-sectional view of the access system of FIG. 61 in the retracted state.

FIG. 61 is a perspective view of another embodiment of an access system 1800 in a retracted state. FIG. 62 is a cross-sectional view of the access system 1800 in the retracted state. The access system 1800 includes a tab 1898 that extends through a longitudinal track 1899 in the housing element. The tab 1898 is attached to an internal coupler 1861, that can resemble previously described followers in general configuration, but can differ significantly therefrom in its connection to the externally positioned tab 1898. The internal coupler 1861 may alternatively be referred to as a follower, although it differs from other followers herein described in at least one significant respect. Whereas the other followers move solely in response to forces applied to the cannula, the internal coupler 1861 may additionally move in response to forces applied to the tab 1898. Regardless, the internal coupler 1861 does not instigate or otherwise cause movement of a cannula 1804 to which it is attached. Movements of the internal coupler 1861 are purely passive and in response to either movement of the cannula 1804 or movement of the tab 1898. The internal coupler 1861 can be connected with portions of a cannula 1804, such that the cannula 1804 can be moved in response to movement of the tab 1898. The tab 1898 can be used to move the internal coupler 1861 forwardly and rearwardly along the designated track 1898 and thereby advance and retract the cannula 1804.

Figure 63:
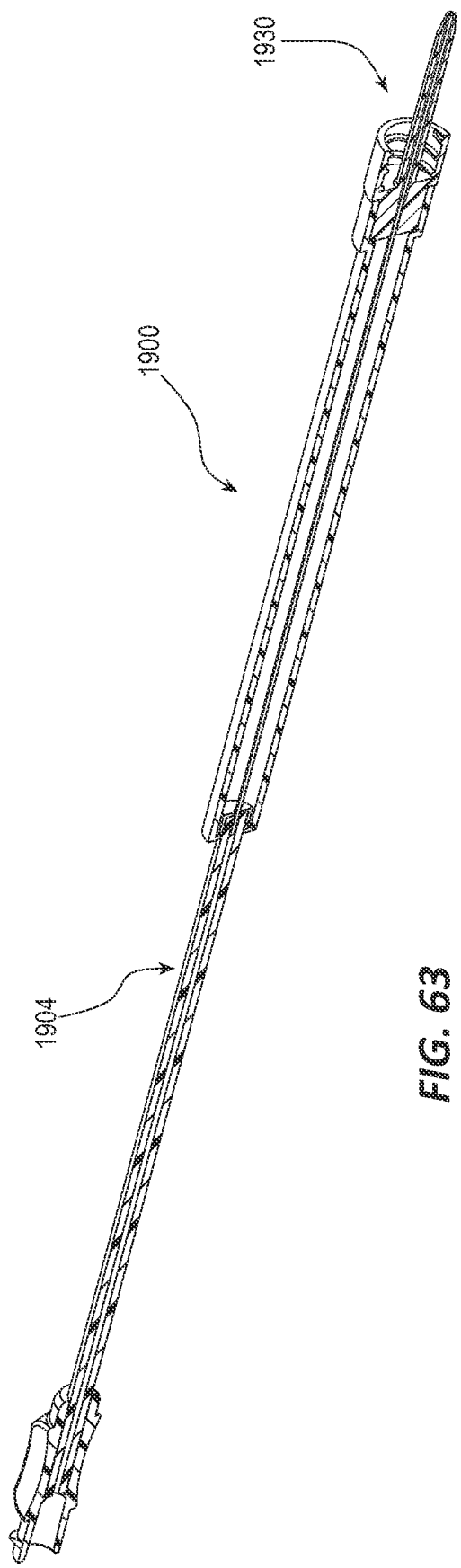
FIG. 63 is a perspective cross-sectional view of another embodiment of an access system.
Figure 64:
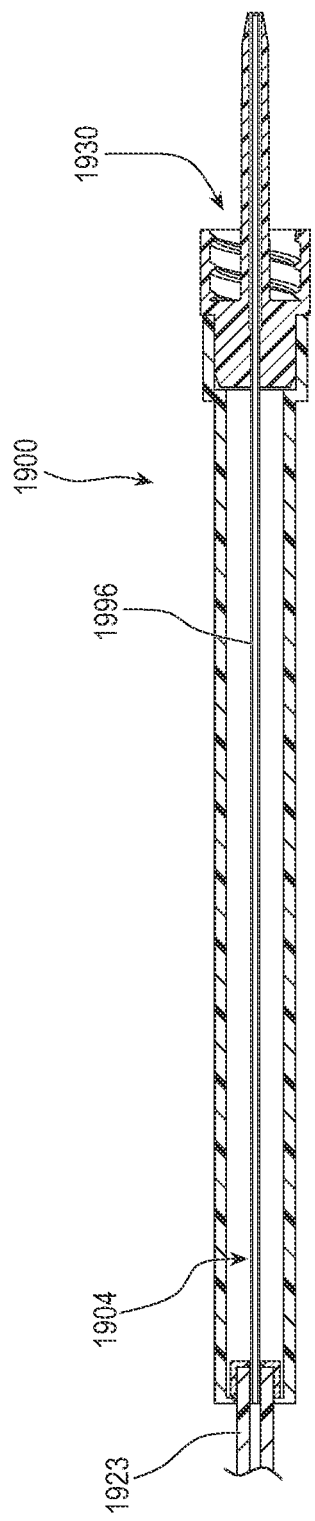
FIG. 64 is a cross-sectional view of a generally distal portion of the access system of FIG. 63.

FIG. 63 is a perspective cross-sectional view of another embodiment of an access system 1900 that includes a deployable cannula 1904. FIG. 64 is a cross-sectional view of a generally distal portion of the access system 1900. The cannula 1904 includes a unitary central tube 1996 (e.g., formed of a polymeric material) without any support tube attached thereto. The central tube 1996 is attached at its proximal end to a proximal 1923. The access system 1900 includes a reinforcement member 1930 at a distal end thereof that is defined by a connection member 1970.

Methods of using embodiments of access systems are discussed above. Certain methods can include placing a base catheter system in the vasculature of a patient. Other or further methods can include coupling an access system with a pre-placed base catheter system. In certain embodiments, the base catheter system may be placed in one or more of a dorsal arch of a hand, a forearm, or an antecubital fossa position on a patient. Various embodiments disclosed herein are capable for use with pre-placed base catheter systems that have been placed at any of these regions. For example, the access systems may include supported cannula that are capable of use with base catheter tubes that may define significantly tortuous paths.

In some instances, the base catheter system may be placed on the patient in a typical fashion that does not involve the use of special spacing or orientation apparatus. For example, some embodiments of access systems may be used with base catheter systems that have been taped down to the skin of the patient or secured to the skin of the patient with a standard flat dressing. There may be no spacing element present, such as a wedge-shaped device configured to provide an entry angle for the access system. That is, the access systems may be usable through a tortuous region defined by a base catheter system that is taped or otherwise secured directly to the skin of the patient.

EXAMPLES

The present paragraph recites 322 illustrative examples of systems, kits, and methods that correspond with various embodiments of the foregoing written description and/or the illustrative drawings. In these examples, the terminology "Example X to Example Y" means Example X through Example Y, and thus includes the endpoints of the recited range of examples.

Example 1

An Access System Comprising:
- a connector configured to couple with a catheter assembly that comprises a catheter tube configured to be positioned in a blood vessel of a patient;
- a reinforcement member coupled with the connector; and
- a cannula movable relative to the reinforcement member from a retracted position in which at least a portion of the cannula is within the reinforcement member to an advanced position, the cannula comprising:
  - a first segment at a distal end of the cannula that defines a distal tip of the cannula; and
  - a second segment that is relatively stiffer than the first segment and extends proximally from the first segment, the second segment comprising a distal terminus that is configured to be within the reinforcement member when the distal tip of the cannula is first positioned distal of and external to the reinforcement member as the cannula is transitioned from the retracted position to the advanced position,
- wherein, when the connector and the catheter assembly are in a coupled state, at least a portion of the first segment of the cannula is configured to be advanced through at least a portion of the catheter tube as the cannula is transitioned from the retracted position to the advanced position.

Example 2

The access system of Example 1, wherein the catheter assembly is configured to be preplaced in the patient such that the catheter tube is positioned in the blood vessel of the patient prior to coupling of the connector of the access system with the catheter assembly.

Example 3

The access system of Example 1 or Example 2, wherein, when the catheter tube of the catheter assembly is positioned in the blood vessel of the patient and when the connector of the access system and the catheter assembly are in the coupled state, advancement of the cannula to the advanced position enables fluid communication directly between the cannula and the blood vessel.

Example 4

The access system of any one of Example 1 to Example 3, wherein when the cannula is in the advanced position, the distal tip of the cannula extends distally past a distal tip of the catheter tube.

Example 5

The access system of any one of Example 1 to Example 3, wherein when the cannula is in the advanced position, the distal tip of the cannula is positioned within the catheter tube at or proximate to a distal tip of the catheter tube.

Example 6

The access system of any one of Example 1 to Example 5, wherein when the cannula is in the advanced position, said at least a portion of the cannula is positioned outside of and distal to a distal tip of the reinforcement member.

Example 7

The access system of any one of Example 1 to Example 6, wherein the second segment of the cannula is relatively harder than the first segment of the cannula.

Example 8

The access system of any one of Example 1 to Example 7, wherein the second segment of the cannula comprises a flexible and/or polymeric tube and a support member that is stiffer than and encompasses at least a portion of the flexible and/or polymeric tube.

Example 9

The access system of Example 8, wherein at least a distal end of the support member is encompassed by the reinforcement member when the cannula is in the retracted position.

Example 10

The access system of Example 8 or Example 9, wherein at least an intermediate portion of the flexible and/or polymeric tube that continuously extends along at least a portion of each of the first and second segments is encompassed by one or more of the reinforcement member and the support member along a full length of the intermediate portion when the cannula is in the retracted position.

Example 11

The access system of any one of Example 8 to Example 10, wherein the support member advances distally through the reinforcement member throughout movement of the cannula from the retracted position to the advanced position.

Example 12

The access system of any one of Example 8 to Example 11, wherein the distal terminus comprises a distal tip of the support member.

Example 13

The access system of any one of Example 8 to Example 12, wherein the flexible and/or polymeric tube fits snugly within the support member.

Example 14

The access system of any one of Example 8 to Example 13, wherein the support member is fixed relative to the flexible and/or polymeric tube.

Example 15

The access system of Example 14, wherein the support member is adhered to the flexible and/or polymeric tube.

Example 16

The access system of any one of Example 8 to Example 15, wherein the flexible and/or polymeric tube extends through a full length of the support member.

Example 17

The access system of any one of Example 8 to Example 16, wherein the support member extends along a full length of the second segment.

Example 18

The access system of any one of Example 8 to Example 17, wherein the cannula further comprises a third segment that extends proximally from the second segment.

Example 19

The access system of Example 18, wherein the third segment comprises a proximal tube having an outer diameter that is larger than an outer diameter of the flexible and/or polymeric tube.

Example 20

The access system of Example 18 or Example 19, wherein the flexible and/or polymeric tube is fixedly secured to the proximal tube.

Example 21

The access system of any one of Example 18 to Example 20, further comprising a follower attached to each of the second and third segments.

Example 22

The access system of any one of Example 8 to Example 20, wherein the first segment comprises a portion of the flexible and/or polymeric tube.

Example 23

The access system of Example 22, wherein the first segment is formed exclusively from the flexible and/or polymeric tube.

Example 24

The access system of Example 22, wherein the flexible and/or polymeric tube is formed of a unitary piece of material that extends continuously from the first segment to the second segment.

Example 25

The access system of any one of Example 8 to Example 24, wherein the flexible and/or polymeric tube is formed of polyimide.

Example 26

The access system of any one of Example 8 to Example 25, wherein the support member comprises a support tube that circumscribes an outer surface of the flexible and/or polymeric tube.

Example 27

The access system of Example 26, wherein the support tube comprises a metallic material

Example 28

The access system of Example 27, wherein the support tube is formed of stainless steel.

Example 29

The access system of any one of Example 8 to Example 28, wherein the support member is sized to slide through at least a portion of the reinforcement member as the cannula is transitioned from the retracted position to the advanced position.

Example 30

The access system of any one of Example 8 to Example 29, further comprising a sealing member coupled to each of the reinforcement member and the support member so as to form a fluid-tight seal to prevent ingress of fluid into or egress of fluid from a space between the reinforcement member and the support member.

Example 31

The access system of Example 30, wherein the sealing member is fixedly secured to the reinforcement member and the support member is movable relative to the sealing member.

Example 32

The access system of Example 30 or Example 31, wherein the sealing member is attached to a proximal end of the reinforcement member.

Example 33

The access system of any one of Example 30 to Example 32 wherein the sealing member encompasses a proximal tip of the reinforcement member.

Example 34

The access system of any one of Example 8 to Example 33, wherein the reinforcement member defines a lumen that defines an inner diameter that is no greater than 20 percent larger than an outer diameter of the support member.

Example 35

The access system of any one of Example 8 to Example 34, wherein the support member prevents kinking of the flexible and/or polymeric tube when the first segment encounters force resistive to distal advancement of the distal tip of the cannula by preventing lateral movement of the flexible and/or polymeric tube within the support member in an amount that otherwise would be sufficient to kink the flexible and/or polymeric tube.

Example 36

The access system of any one of Example 1 to Example 7, wherein the first segment comprises a first tube that comprises a first end face, the second segment comprises a second tube that comprises a second end face, and the first and second end faces abut one another at an interface positioned at the distal terminus of the second segment.

Example 37

The access system of Example 36, wherein each of the first and second end faces is transversely oriented relative to a longitudinal axis of the cannula.

Example 38

The access system of Example 36 or Example 37, wherein the second tube is stiffer than the first tube.

Example 39

The access system of Example 38, wherein the second tube is formed of a metallic material Example 40

The access system of Example 39, wherein the second tube is formed of stainless steel.

Example 41

The access system of any one of Example 36 to Example 40, wherein the first tube is formed of a polymeric material.

Example 42

The access system of any one of Example 36 to Example 41, further comprising a tie layer extending over the interface and at least a portion of each of the first and second tubes of the first and second segments, respectively, to attach the first and second tubes together or to reinforce an attachment between the first and second tubes.

Example 43

The access system of Example 42, wherein an outer diameter of the first tube and an outer diameter of the second tube are substantially identical in at least a region of the cannula that includes the interface.

Example 44

The access system of Example 42 or Example 43, wherein an outer diameter of the tie layer is substantially constant along a transition region that includes a proximal end of the first segment, the interface, and a distal end of the second segment.

Example 45

The access system any one of Example 42 to Example 44, wherein the tie layer comprises a tubular member that defines a thickness that is no less than five times smaller than a thickness of the first tube.

Example 46

The access system of any one of Example 42 to Example 45, wherein the tie layer comprises a tube formed of heat shrinkable material.

Example 47

The access system of any one of Example 42 to Example 46, wherein a hardness of the tie layer is less than a hardness of the first segment.

Example 48

The access system of any one of Example 42 to Example 47, wherein a distal tip of the tie layer is proximally spaced from the distal tip of the cannula, and wherein the distal tip of the tie layer is configured to contact an internal surface of the catheter tube to delimit proximal movement of the cannula relative to the catheter tube.

Example 49

The access system of any one of Example 42 to Example 48, wherein a distal tip of the tie layer is proximally spaced from the distal tip of the cannula, and wherein the distal tip of the tie layer is configured to contact an internal surface of the catheter tube to provide tactile feedback to a user regarding a position of the cannula relative to the catheter tube.

Example 50

The access system of any one of Example 1 to Example 49, wherein the reinforcement member prevents kinking of the first segment when the first segment encounters force resistive to distal advancement of the distal tip of the cannula by preventing lateral movement of the first segment within the reinforcement member in an amount that otherwise would be sufficient to kink the first segment.

Example 51

The access system of any one of Example 1 to Example 50, wherein an inner diameter of the first segment is no greater than an inner diameter of the second segment.

Example 52

The access system of any one of Example 1 to Example 50, wherein an inner diameter of the first segment and an inner diameter of the second segment are substantially identical in at least a region of the cannula that includes the terminus.

Example 53

The access system of any one of Example 1 to Example 52, wherein the reinforcement member defines a lumen that defines an inner diameter that is no greater than 20 percent larger than an outer diameter of the first segment of the cannula.

Example 54

The access system of Example 53, wherein the inner diameter of the lumen is constant along a tubular region that extends along at least a portion of a full length of the reinforcement member.

Example 55

The access system of Example 54, wherein the tubular region extends to a distal tip of the reinforcement member.

Example 56

The access system of Example 54 or Example 55, wherein the tubular region extends along at least a majority of the full length of the reinforcement member.

Example 57

The access system of any one of Example 1 to Example 56, wherein the reinforcement member comprises a stainless steel tube.

Example 58

The access system of Example 57, wherein the reinforcement member further comprises a polymeric material overmolded onto the stainless steel tube.

Example 59

The access system of any one of Example 1 to Example 56, wherein the connector and the reinforcement member are integrally formed of a unitary piece of material.

Example 60

The access system of Example 59, wherein the unitary piece of material is polymeric.

Example 61

The access system of any one of Example 1 to Example 60, wherein the first segment is shorter than the reinforcement member.

Example 62

The access system of any one of Example 1 to Example 60, wherein the first segment is longer than the reinforcement member.

Example 63

The access system of any one of Example 1 to Example 62, wherein the distal tip of the cannula is positioned within the reinforcement member when the cannula is in the retracted position, such that the distal tip of the cannula is first positioned distal of and external to the reinforcement member only after the cannula has been moved from the retracted position.

Example 64

The access system of any one of Example 1 to Example 62, wherein the distal tip of the cannula is first positioned distal of and external to the reinforcement member when the cannula is in the retracted position.

Example 65

The access system of any one of Example 1 to Example 64, wherein the distal terminus of the second segment of the cannula is within the reinforcement member when the cannula is in the retracted position.

Example 66

The access system of any one of Example 1 to Example 65, wherein the distal terminus of the second segment of the cannula is distal to a distal edge of the reinforcement member when the cannula is in the advanced position.

Example 67

The access system of any one of Example 1 to Example 66, wherein the catheter assembly comprises an extension set that comprises a hub, wherein the distal terminus of the second segment of the cannula is positioned within the hub when the cannula is in the advanced position.

Example 68

The access system of any one of Example 1 to Example 66, wherein the catheter assembly comprises a catheter hub coupled to the catheter tube, wherein the distal terminus of the second segment of the cannula is positioned within the catheter hub when the cannula is in the advanced position.

Example 69

The access system of any one of Example 1 to Example 65, wherein the distal terminus of the second segment of the cannula is within the reinforcement member when the cannula is in the advanced position.

Example 70

The access system of any one of Example 1 to Example 65, wherein the distal terminus of the second segment of the cannula is within the reinforcement member throughout movement of the cannula from the retracted position to the advanced position.

Example 71

The access system of any one of Example 1 to Example 70, further comprising a sheath coupled to the connector, wherein the cannula extends through at least a portion of the sheath, the cannula being movable relative to the sheath from the retracted position to the advanced position.

Example 72

The access system of Example 71, wherein at least a portion of the sheath and at least a portion of the connector are integrally formed of a unitary piece of material.

Example 73

The access system of Example 71 or Example 72, wherein, when the cannula is in each of the retracted and advanced positions, at least some portion of the cannula is positioned within the sheath.

Example 74

The access system of any one of Example 71 to Example 73, wherein at least some portion of the cannula is positioned within the sheath throughout movement of the cannula from the retracted position to the advanced position.

Example 75

The access system of any one of Example 71 to Example 74, wherein the sheath comprises a tube having a proximal end and a distal end, and wherein the cannula extends through at least the proximal end of the sheath when in the retracted position and extends through at least the distal end of the sheath when in the advanced position.

Example 76

The access system of any one of Example 71 to Example 75, further comprising a follower fixedly attached to the cannula and positioned within the sheath, wherein the follower moves in unison with the cannula as the cannula is moved from the retracted position to the advanced position.

Example 77

The access system of Example 76, wherein the follower cooperates with the sheath to delimit proximal movement of the cannula relative to the sheath.

Example 78

The access system of Example 76 or Example 77, wherein the follower and the sheath comprise a rotational alignment mechanism by which a rotational orientation of the cannula is maintained relative to the sheath.

Example 79

The access system of Example 78, wherein the rotational alignment mechanism comprises a protrusion positioned within a groove, wherein the sheath defines one of the protrusion and the groove and the follower defines the other of the protrusion and the groove.

Example 80

The access system of any one of Example 76 to Example 79, wherein: the reinforcement member comprises a reinforcing tube that is movable relative to the connector;
the follower is coupled to the reinforcing tube while the cannula is in the retracted position such that the follower and the reinforcing tube move distally in tandem with the cannula throughout movement of the cannula from the retracted position to an intermediate position that is proximal of the advanced position; and
the follower is configured to decouple from the reinforcing tube as the cannula is moved distally past the intermediate position.

Example 81

The access system of Example 80, wherein when the follower decouples from the reinforcing tube, the follower and the cannula are permitted to move distally relative to the reinforcing tube while the reinforcing tube remains fixed relative to the connector.

Example 82

The access system of Example 80 or Example 81, further comprising a catch fixedly attached to the reinforcing tube, wherein the follower comprises a plurality of arms that grasp the catch throughout movement of the cannula from the retracted position to the intermediate position and release the catch as the cannula is moved distally past the intermediate position.

Example 83

The access system of Example 82, wherein:
the sheath comprises a first chamber that defines a first diameter and a second chamber positioned distal of the first chamber that defines a second diameter larger than the first diameter;
the first chamber of the sheath is sized to constrain at least distal ends of the plurality of arms from flexing outwardly while the distal ends are positioned in the first chamber such that the arms engage the catch while in the first chamber; and
the second chamber of the sheath is sized to permit the distal ends of the plurality of arms to flex outwardly to disengage from the catch and to move distally past the catch.

Example 84

The access system of Example 83, wherein a proximal end of the second chamber is proximal of the intermediate position.

Example 85

The access system of Example 83 or Example 84, wherein the plurality of arms are outwardly biased such that the distal ends of the plurality of arms automatically flex outwardly and disengage from the catch when advanced through the second chamber of the sheath.

Example 86

The access system of Example 83 or Example 84, wherein the plurality of arms and the catch comprise a ramped interface that causes the distal ends of the plurality of arms to flex outwardly and disengage from the catch when positioned in the second chamber of the sheath and when the reinforcing tube encounters increased resistance to distal movement as the cannula is advanced toward the advanced position.

Example 87

The access system of any one of Example 71 to Example 86, further comprising an actuator attached to the cannula, wherein at least a portion of the actuator is accessible external to the sheath so as to be manipulated to move the cannula between the advanced and retracted positions.

Example 88

The access system of Example 87, wherein the sheath comprises a longitudinally extending track, and wherein a portion of the actuator extends through the track.

Example 89

The access system of any one of Example 71 to Example 88, wherein the cannula is moved from the retracted position to the advanced position by directly contacting the cannula.

Example 90

The access system of any one of Example 1 to Example 89, wherein the connector comprises a threaded region that is configured to cooperate with a complementary portion of the catheter assembly to securely couple the connector with the catheter assembly.

Example 91

The access system of any one of Example 1 to Example 89, wherein the connector comprises at least two flaps that are configured to cooperate with a portion of the catheter assembly to securely snap the connector onto the catheter assembly.

Example 92

The access system of any one of Example 1 to Example 91, wherein the cannula comprises a further connector at a proximal end thereof for connecting the cannula to a fluid transfer device.

Example 93

The access system of Example 92, wherein the fluid transfer device comprises a blood collection unit.

Example 94

The access system of Example 92 of Example 93, wherein the further connector comprises a luer fitting.

Example 95

The access system of any one of Example 1 to Example 94, wherein the cannula is further movable from the advanced position to the retracted position.

Example 96

The access system of any one of Example 1 to Example 95, wherein when the cannula is in the advanced position, a length of the cannula extends through the reinforcement member.

Example 97

The access system of Example 96, wherein the second segment of the cannula defines at least a portion of the length of the cannula that extends through the reinforcement member when the cannula is in the advanced position.

Example 98

The access system of any one of Example 1 to Example 97, wherein:

the catheter assembly comprises a septum; and
a distal tip of the reinforcement member is configured to be positioned proximal to the septum when the connector is attached to the catheter assembly.

Example 99

The access system of any one of Example 1 to Example 97, wherein:

the catheter assembly comprises a septum;
the reinforcement member comprises a projection that extends distally from a surface of the connector; and
at least a portion of the projection of the reinforcement member is configured to extend through the septum of the catheter assembly when the connector is attached to the catheter assembly.

Example 100

The access system of Example 99, wherein the septum comprises an opening that is in an unsealed state prior to insertion of the projection of the reinforcement member through the septum.

Example 101

The access system of Example 100, wherein the projection of the reinforcement member is configured to be inserted through the opening of the septum.

Example 102

The access system of any one of Example 99 to Example 101, wherein the projection extends distally past a distal end of the connector.

Example 103

The access system of any one of Example 99 to Example 101, wherein the projection is proximally recessed relative to a distal end of the connector.

Example 104

The access system of any one of Example 99 to Example 104, wherein the catheter assembly further comprises a valve positioned distal to the septum.

Example 105

The access system of Example 104, wherein, when the connector is coupled with the catheter assembly, no portion of the reinforcement member extends through the valve.

Example 106

The access system of Example 104 or Example 105, wherein, when the connector is coupled with the catheter assembly, a distal tip of the reinforcement member is at or proximally spaced from a proximal surface of the valve.

Example 107

The access system of any one of Example 104 to Example 106, wherein, when the connector is coupled with the catheter assembly, a portion of the reinforcement member extends through the septum.

Example 108

The access system of any one of Example 104 to Example 107, wherein, when the connector is coupled with the catheter assembly, the reinforcement member aims the cannula toward a sealable opening of the valve such that the distal tip of the cannula is advanced through the sealable opening of the valve as the cannula is moved from the retracted position to the advanced position.

Example 109

The access system of Example 108, wherein the sealable opening is substantially centered relative to the valve, and wherein, when the connector is coupled with the catheter assembly, the reinforcement member is substantially centered so as to be aligned with the sealable opening.

Example 110

The access system of any one of Example 104 to Example 109, wherein, when the cannula is in the advanced position, at least a portion of the second segment of the cannula extends through the valve.

Example 111

The access system of Example 110, wherein, when the cannula is in the advanced position, the distal terminus of the second segment of the cannula is distal to the valve.

Example 112

The access system of any one of Example 99 to Example 111, wherein the catheter assembly further comprises a removable piercing member that extends through the septum and through the catheter tube to assist in positioning the catheter tube in the blood vessel of the patient, and wherein the piercing member is configured to be removed from the catheter assembly prior to coupling the connector of the access system with the catheter assembly.

Example 113

The access system of Example 112, wherein the removable piercing member further extends through the valve when extending through the septum and through the catheter tube.

Example 114

The access system of any one of Example 1 to Example 97, wherein the catheter assembly is a closed intravenous catheter system.

Example 115

The access system of Example 114, wherein the closed intravenous catheter system comprises an integrated side port through which fluid may be transferred to or from the catheter tube.

Example 116

The access system of any one of Example 1 to Example 97, wherein the catheter assembly is an open intravenous catheter system.

Example 117

The access system of any one of Example 1 to Example 116, wherein an entirety of the reinforcement member is external to the catheter tube when the connector is coupled with the catheter assembly.

Example 118

The access system of Example 117, wherein the entirety of the reinforcement member remains external to the catheter tube throughout movement of the cannula from the retracted position to the advanced position.

Example 119

The access system of any one of Example 1 to Example 118, wherein a distal tip of the reinforcement member is proximal to a proximal tip the catheter tube when the connector is coupled with the catheter assembly.

Example 120

The access system of Example 119, wherein the distal tip of the reinforcement member remains proximal to the proximal tip of the catheter tube throughout movement of the cannula from the retracted position to the advanced position.

Example 121

The access system of Example 1, wherein the reinforcement member is fixed relative to the connector.

Example 122

The access system of Example 1, wherein the reinforcement member comprises a first metallic hypotube, and wherein the second segment comprises a second metallic hypotube sized to translate within the first metallic hypotube.

Example 123

The access system of Example 122, wherein each of the first and second segments is at least partially defined by a unitary polymeric tube, and wherein the second metallic hypotube encompasses a portion of the polymeric tube.

Example 124

The access system of Example 122 or Example 123, wherein a distal tip of the second metallic hypotube defines the distal terminus of the second segment.

Example 125

The access system of any one of Example 1 to Example 124, further comprising the catheter assembly.

Example 126

A kit comprising:
    an access system according to any one of Example 1 to Example 125; and
    instructions for using the kit, the instructions comprising directions to:
        couple the connector to the catheter assembly while the catheter tube of the catheter assembly is positioned in the blood vessel of the patient; and advance the cannula from the retracted position to the advanced position.

Example 127

The kit of Example 126, wherein the instructions for using the kit further comprise directions to:
  couple a fluid transfer device to the cannula; and
  draw blood from the blood vessel through the cannula and into the fluid transfer device.

Example 128

A method of using the access system of any one of Example 1 to Example 125, the method comprising:
  coupling the connector to the catheter assembly while the catheter tube of the catheter assembly is positioned in the blood vessel of the patient; and
  advancing the cannula from the retracted position to the advanced position.

Example 129

An Access System Comprising:
  a connector configured to couple with a catheter assembly that comprises a catheter tube configured to be positioned in a blood vessel of a patient;
  a reinforcement member coupled with the connector; and
  a cannula movable relative to the reinforcement member from a retracted position in which at least a portion of the cannula is within the reinforcement member to an advanced position, the cannula comprising:
    a flexible and/or polymeric tube that defines a distal tip; and
    a support tube that is stiffer than and encompasses a portion of the flexible and/or polymeric tube, the support tube defining a distal edge that is configured to be within the reinforcement member when the distal tip of the flexible and/or polymeric tube is first positioned distal of and external to the reinforcement member as the cannula is transitioned from the retracted position to the advanced position,
  wherein, when the connector and the catheter assembly are in a coupled state, at least a portion of the flexible and/or polymeric tube is configured to be advanced through at least a portion of the catheter tube as the cannula is transitioned from the retracted position to the advanced position. By flexible and/or polymeric tube, it is meant that in some embodiments, the cannula comprises a flexible tube (whether or not the tube is polymeric), while in other or further embodiments, the cannula comprises a polymeric tube, which can have properties such as described in the present disclosure.

Example 130

An Access System Comprising:
  a connector configured to couple with a catheter assembly that comprises a catheter tube configured to be positioned in a blood vessel of a patient;
  a reinforcement member coupled with the connector; and
  a cannula movable relative to the reinforcement member from a retracted position in which at least a portion of the cannula is within the reinforcement member to an advanced position, the cannula comprising:
    a flexible and/or polymeric tube that defines a distal tip; and
    a support tube that encompasses a portion of the flexible and/or polymeric tube, the support tube being in a fixed relationship with the flexible and/or polymeric tube so as to move in unison with the flexible and/or polymeric tube as the cannula is transitioned from the retracted position to the advanced position,
  wherein, when the connector and the catheter assembly are in a coupled state, at least a portion of the flexible and/or polymeric tube is configured to be advanced through at least a portion of the catheter tube as the cannula is transitioned from the retracted position to the advanced position.

Example 131

An Access System Comprising:
  a connector configured to couple with a catheter assembly that comprises a catheter tube configured to be positioned in a blood vessel of a patient;
  a reinforcement member coupled with the connector; and
  a cannula movable relative to the reinforcement member from a retracted position in which at least a portion of the cannula is within the reinforcement member to an advanced position, the cannula comprising:
    a flexible and/or polymeric tube that defines a distal tip; and
    a support tube that encompasses a portion of the flexible and/or polymeric tube, the support tube defining a distal edge that is proximally spaced from the distal tip of the flexible and/or polymeric tube,
  wherein, when the connector and the catheter assembly are in a coupled state, at least a portion of the flexible and/or polymeric tube is configured to be advanced through at least a portion of the catheter tube as the cannula is transitioned from the retracted position to the advanced position.

Example 132

The access system of any one of Example 129 to Example 131, wherein, at each stage throughout movement of the cannula from the retracted position to the advanced position, at least some portion of the support tube is positioned within the reinforcement member.

Example 133

The access system of any one of Example 129 to Example 132, wherein the flexible and/or polymeric tube comprises polyimide.

Example 134

The access system of any one of Example 129 to Example 133, wherein the distal edge of the support tube is configured to extend distally past a distal tip of the reinforcement member when the cannula is in the advanced position.

Example 135

The access system of any one of Example 129 to Example 134, wherein the distal tip of the flexible and/or polymeric tube is positioned within the reinforcement member when the cannula is in the retracted position, such that the distal tip of the flexible and/or polymeric tube is first positioned distal of and external to the reinforcement member only after the cannula has been moved from the retracted position.

Example 136

The access system of any one of Example 129 to Example 134, wherein the distal tip of the flexible and/or polymeric tube is first positioned distal of and external to the reinforcement member when the cannula is in the retracted position.

Example 137

The access system of any one of Example 129 to Example 136, wherein the distal edge of the support tube is within the reinforcement member when the cannula is in the retracted position.

Example 138

The access system of any one of Example 129 to Example 137, wherein the distal edge of the support tube is distal to a distal edge of the reinforcement member when the cannula is in the advanced position.

Example 139

The access system of any one of Example 129 to Example 138, wherein the catheter assembly comprises an extension set that comprises a hub, wherein the distal edge of the support tube is positioned within the hub when the cannula is in the advanced position.

Example 140

The access system of any one of Example 129 to Example 138, wherein the catheter assembly comprises a catheter hub coupled to the catheter tube, wherein the distal edge of the support tube is positioned within the catheter hub when the cannula is in the advanced position.

Example 141

The access system of any one of Example 129 to Example 137, wherein the distal edge of the support tube is within the reinforcement member when the cannula is in the advanced position.

Example 142

The access system of Example 129 or Example 141, wherein the distal edge of the support tube is within the reinforcement member throughout movement of the cannula from the retracted position to the advanced position.

Example 143

The access system of any one of Example 129 to Example 142, further comprising a sheath coupled to the connector, wherein the cannula extends through at least a portion of the sheath, the cannula being movable relative to the sheath from the retracted position to the advanced position.

Example 144

The access system of Example 143, wherein at least a portion of the sheath and at least a portion of the connector are integrally formed of a unitary piece of material.

Example 145

The access system of Example 143 or Example 144, wherein, when the cannula is in each of the retracted and advanced positions, at least some portion of the cannula is positioned within the sheath.

Example 146

The access system of any one of Example 143 to Example 145, wherein at least some portion of the cannula is positioned within the sheath throughout movement of the cannula from the retracted position to the advanced position.

Example 147

The access system of any one of Example 143 to Example 146, wherein the sheath comprises a tube having a proximal end and a distal end, and wherein the cannula extends through at least the proximal end of the sheath when in the retracted position and extends through at least the distal end of the sheath when in the advanced position.

Example 148

The access system of any one of Example 143 to Example 147, further comprising a follower fixedly attached to the cannula and positioned within the sheath, wherein the follower moves in unison with the cannula as the cannula is moved from the retracted position to the advanced position.

Example 149

The access system of Example 148, wherein the follower cooperates with the sheath to delimit proximal movement of the cannula relative to the sheath.

Example 150

The access system of Example 148 or Example 149, wherein the follower and the sheath comprise a rotational alignment mechanism by which a rotational orientation of the cannula is maintained relative to the sheath.

Example 151

The access system of Example 150, wherein the rotational alignment mechanism comprises a protrusion positioned within a groove, wherein the sheath defines one of the protrusion and the groove and the follower defines the other of the protrusion and the groove.

Example 152

The access system of any one of Example 129 to Example 151, wherein:
　the catheter assembly comprises a septum; and
　a distal tip of the reinforcement member is configured to be positioned proximal to the septum when the connector is attached to the catheter assembly.

Example 153

The access system of any one of Example 129 to Example 151, wherein:
　the catheter assembly comprises a septum;

the reinforcement member comprises a projection that extends distally from a surface of the connector; and at least a portion of the projection of the reinforcement member is configured to extend through the septum of the catheter assembly when the connector is attached to the catheter assembly.

Example 154

The access system of Example 153, wherein the septum comprises a sealable region that provides a fluid-tight seal prior to insertion of the projection of the reinforcement member through the sealable region.

Example 155

The access system of Example 153, wherein the septum comprises an opening that is in an unsealed state prior to insertion of the projection of the reinforcement member through the septum.

Example 156

The access system of Example 155, wherein the projection of the reinforcement member is configured to be inserted through the opening of the septum.

Example 157

The access system of any one of Example 153 to Example 156, wherein the projection extends distally past a distal end of the connector.

Example 158

The access system of any one of Example 153 to Example 156, wherein the projection is proximally recessed relative to a distal end of the connector.

Example 159

The access system of any one of Example 153 to Example 158, wherein the catheter assembly further comprises a valve positioned distal to the septum.

Example 160

The access system of Example 159, wherein, when the connector is coupled with the catheter assembly, no portion of the reinforcement member extends through the valve.

Example 161

The access system of Example 159 or Example 160, wherein, when the connector is coupled with the catheter assembly, a distal tip of the reinforcement member is at or proximally spaced from a proximal surface of the valve.

Example 162

The access system of any one of Example 159 to Example 161, wherein, when the connector is coupled with the catheter assembly, a portion of the reinforcement member extends through the septum.

Example 163

The access system of any one of Example 159 to Example 162, wherein, when the connector is coupled with the catheter assembly, the reinforcement member aims the cannula toward a sealable opening of the valve such that the distal tip of the flexible and/or polymeric tube is advanced through the sealable opening of the valve as the cannula is moved from the retracted position to the advanced position.

Example 164

The access system of Example 163, wherein the sealable opening is substantially centered relative to the valve, and wherein, when the connector is coupled with the catheter assembly, the reinforcement member is substantially centered so as to be aligned with the sealable opening.

Example 165

The access system of any one of Example 153 to Example 164, wherein the catheter assembly further comprises a removable piercing member that extends through the septum and through the catheter tube to assist in positioning the catheter tube in the blood vessel of the patient, and wherein the piercing member is configured to be removed from the catheter assembly prior to coupling the connector of the access system with the catheter assembly.

Example 166

The access system of any one of Example 159 to Example 165, wherein the removable piercing member further extends through the valve when extending through the septum and through the catheter tube.

Example 167

The access system of any one of Example 129 to Example 166, wherein the catheter assembly is a closed intravenous catheter system.

Example 168

The access system of Example 167, wherein the closed intravenous catheter system comprises an integrated side port through which fluid may be transferred to or from the catheter tube.

Example 169

The access system of any one of Example 129 to Example 166, wherein the catheter assembly is an open intravenous catheter system.

Example 170

The access system of any one of Example 129 to Example 169, further comprising a sealing member coupled to each of the reinforcement member and the support tube so as to form a fluid-tight seal to prevent ingress of fluid into or egress of fluid from a space between the reinforcement member and the support tube.

Example 171

The access system of Example 170, wherein the sealing member is fixedly secured to the reinforcement member and the support tube is movable relative to the sealing member.

Example 172

The access system of Example 170 or Example 171, wherein the sealing member is attached to a proximal end of the reinforcement member.

Example 173

The access system of any one of Example 170 to Example 172 wherein the sealing member encompasses a proximal tip of the reinforcement member.

Example 174

The access system of any one of Example 129 to Example 173, further comprising the catheter assembly.

Example 175

A kit comprising:
 an access system according to any one of Example 129 to Example 174; and
 instructions for using the kit, the instructions comprising directions to:
  couple the connector to the catheter assembly while the catheter tube of the catheter assembly is positioned in the blood vessel of the patient; and
  advance the cannula from the retracted position to the advanced position.

Example 176

The kit of Example 175, wherein the instructions for using the kit further comprise directions to:
 couple a fluid transfer device to the cannula; and
 draw blood from the blood vessel through the cannula and into the fluid transfer device.

Example 177

A method of using the access system of any one of Example 129 to Example 174, the method comprising:
 coupling the connector to the catheter assembly when the catheter tube of the catheter assembly is positioned in the blood vessel of the patient; and
 advancing the cannula from the retracted position to the advanced position.

Example 178

An Access System Comprising:
 a connector configured to couple with a closed intravenous catheter system that comprises a valve and a catheter tube that is configured to be positioned in a blood vessel of a patient;
 a reinforcement member coupled with the connector such that when the connector is coupled with the closed intravenous catheter system, a distal tip of the reinforcement member is at or proximally spaced from a proximal surface of the valve; and
 a cannula movable relative to the reinforcement member from a retracted position to an advanced position,
  wherein, when the connector and the closed intravenous catheter system are in a coupled state, at least a portion of the cannula is configured to be advanced through the valve and through at least a portion of the catheter tube as the cannula is transitioned from the retracted position to the advanced position.

Example 179

An Access System Comprising:
 a connector configured to couple with a closed intravenous catheter system that comprises a valve and a catheter tube that is configured to be positioned in a blood vessel of a patient;
 a reinforcement member coupled with the connector such that when the connector is coupled with the closed intravenous catheter system, no portion of the reinforcement member is in contact with the valve; and
 a cannula movable relative to the reinforcement member from a retracted position to an advanced position,
  wherein, when the connector and the closed intravenous catheter system are in a coupled state, at least a portion of the cannula is configured to be advanced through the valve and through at least a portion of the catheter tube as the cannula is transitioned from the retracted position to the advanced position.

Example 180

An Access System Comprising:
 a connector configured to couple with a closed intravenous catheter system that comprises a valve and a catheter tube that is configured to be positioned in a blood vessel of a patient;
 a reinforcement member coupled with the connector such that when the connector is coupled with the closed intravenous catheter system, no portion of the reinforcement member extends through the valve; and a cannula movable relative to the reinforcement member from a retracted position to an advanced position,
  wherein, when the connector and the closed intravenous catheter system are in a coupled state, at least a portion of the cannula is configured to be advanced through the valve and through at least a portion of the catheter tube as the cannula is transitioned from the retracted position to the advanced position.

Example 181

The access system of any one of Example 178 to Example 180, wherein the closed intravenous catheter system is configured to be preplaced in the patient such that the catheter tube is positioned in the blood vessel of the patient prior to coupling of the connector of the access system with the closed intravenous catheter system.

Example 182

The access system of any one of Example 178 to Example 181, wherein, when the catheter tube of the closed intravenous catheter system is positioned in the blood vessel of the patient and when the connector of the access system and the closed intravenous catheter system are in the coupled state, advancement of the cannula to the advanced position enables fluid communication directly between the cannula and the blood vessel.

Example 183

The access system of any one of Example 178 to Example 182, wherein when the cannula is in the advanced position, a distal tip of the cannula extends distally past a distal tip of the catheter tube.

Example 184

The access system of any one of Example 178 to Example 182, wherein when the cannula is in the advanced position, a distal tip of the cannula is positioned within the catheter tube at or proximate to a distal tip of the catheter tube.

Example 185

The access system of any one of Example 178 to Example 184, wherein when the cannula is in the advanced position, at least a portion of the cannula is positioned outside of and distal to a distal tip of the reinforcement member.

Example 186

The access system of any one of Example 178 to Example 185, wherein the cannula comprises a first segment at a distal end thereof and a second segment that extends proximally from the first segment and is relatively stiffer than the first segment.

Example 187

The access system of Example 186, wherein the second segment of the cannula comprises a flexible and/or polymeric tube and a support member that encompasses at least a portion of the flexible and/or polymeric tube.

Example 188

The access system of Example 187, wherein the support member is in a fixed relation relative to the flexible and/or polymeric tube so as to move in unison therewith.

Example 189

The access system of Example 187 or Example 188, wherein at least a distal end of the support member is encompassed by the reinforcement member when the cannula is in the retracted position.

Example 190

The access system of any one of Example 187 to Example 189, wherein at least an intermediate portion of the flexible and/or polymeric tube that continuously extends along at least a portion of each of the first and second segments is encompassed by one or more of the reinforcement member and the support member along a full length of the intermediate portion.

Example 191

The access system of any one of Example 187 to Example 190, wherein the support member advances distally through the reinforcement member throughout movement of the cannula from the retracted position to the advanced position.

Example 192

The access system of any one of Example 187 to Example 191, wherein a distal tip of the support member corresponds with a distal terminus of the second segment.

Example 193

The access system of any one of Example 187 to Example 192, wherein the flexible and/or polymeric tube fits snugly within the support member.

Example 194

The access system of any one of Example 187 to Example 193, wherein the support member is fixedly secured to the flexible and/or polymeric tube.

Example 195

The access system of Example 194, wherein the support member is adhered to the flexible and/or polymeric tube.

Example 196

The access system of any one of Example 187 to Example 195, wherein the flexible and/or polymeric tube extends through a full length of the support member.

Example 197

The access system of any one of Example 187 to Example 196, wherein the support member extends along a full length of the second segment.

Example 198

The access system of any one of Example 187 to Example 197, wherein:
  the cannula further comprises a third segment that extends proximally from the second segment;
  the third segment comprises a proximal tube having an outer diameter that is larger than an outer diameter of the flexible and/or polymeric tube; and
  the flexible and/or polymeric tube is fixedly secured to the proximal tube.

Example 199

The access system of any one of Example 187 to Example 198, wherein the first segment comprises a portion of the flexible and/or polymeric tube.

Example 200

The access system of Example 199, wherein the first segment is formed exclusively from the flexible and/or polymeric tube.

Example 201

The access system of Example 199, wherein the flexible and/or polymeric tube is formed of a unitary piece of material that extends continuously from the first segment to the second segment.

Example 202

The access system of any one of Example 187 to Example 201, wherein the flexible and/or polymeric tube is formed of polyimide.

Example 203

The access system of any one of Example 187 to Example 202, wherein the support member comprises a support tube that circumscribes an outer surface of the flexible and/or polymeric tube.

Example 204

The access system of Example 203, wherein the support tube is formed of stainless steel.

Example 205

The access system of any one of Example 187 to Example 204, wherein the support member is sized to slide through at least a portion of the reinforcement member as the cannula is transitioned from the retracted position to the advanced position.

Example 206

The access system of any one of Example 187 to Example 205, wherein the reinforcement member defines a lumen that defines an inner diameter that is no greater than 20 percent larger than an outer diameter of the support member.

Example 207

The access system of any one of Example 187 to Example 206, wherein the support member prevents kinking of the flexible and/or polymeric tube when the first segment encounters force resistive to distal advancement of the distal tip of the cannula by preventing lateral movement of the flexible and/or polymeric tube within the support member in an amount that otherwise would be sufficient to kink the flexible and/or polymeric tube.

Example 208

The access system of Example 186, wherein the first segment comprises a first tube that comprises a first end face, the second segment comprises a second tube that comprises a second end face, and the first and second end faces abut one another at an interface positioned at the distal terminus of the second segment.

Example 209

The access system of Example 208, wherein each of the first and second end faces is transversely oriented relative to a longitudinal axis of the cannula.

Example 210

The access system of Example 208 or Example 209, wherein the second tube is formed of stainless steel.

Example 211

The access system of any one of Example 208 to Example 210, wherein the first tube is formed of a polymeric material.

Example 212

The access system of any one of Example 208 to Example 211, further comprising a tie layer extending over the interface and at least a portion of each of the first and second tubes of the first and second segments, respectively, to attach the first and second tubes together or to reinforce an attachment between the first and second tubes.

Example 213

The access system of Example 212, wherein an outer diameter of the first tube and an outer diameter of the second tube are substantially identical in at least a region of the cannula that includes the interface.

Example 214

The access system of Example 212 or Example 213, wherein an outer diameter of the tie layer is substantially constant along a transition region that includes a proximal end of the first segment, the interface, and a distal end of the second segment.

Example 215

The access system any one of Example 212 to Example 214, wherein the tie layer comprises a tubular member that defines a thickness that is no less than 20 times smaller than a thickness of the first tube.

Example 216

The access system of any one of Example 212 to Example 215, wherein the tie layer comprises a tube formed of heat shrinkable material.

Example 217

The access system of any one of Example 212 to Example 216, wherein a hardness of the tie layer is less than a hardness of the first segment.

Example 218

The access system of any one of Example 212 to Example 217, wherein a distal tip of the tie layer is proximally spaced from the distal tip of the cannula, and wherein the distal tip of the tie layer is configured to contact an internal surface of the catheter tube to delimit proximal movement of the cannula relative to the catheter tube.

Example 219

The access system of any one of Example 212 to Example 218, wherein a distal tip of the tie layer is proximally spaced from the distal tip of the cannula, and wherein the distal tip of the tie layer is configured to contact an internal surface of the catheter tube to provide tactile feedback to a user regarding a position of the cannula relative to the catheter tube.

Example 220

The access system of any one of Example 178 to Example 219, wherein the reinforcement member prevents kinking of the cannula when the cannula encounters force resistive to distal advancement of a distal tip of the cannula by preventing lateral movement of the cannula within the reinforcement member in an amount that otherwise would be sufficient to kink the cannula.

Example 221

The access system of any one of Example 178 to Example 220, wherein the reinforcement member defines a lumen that defines an inner diameter that is no greater than 20 percent larger than an outer diameter of a distal portion of the cannula.

Example 222

The access system of Example 221, wherein the inner diameter of the lumen is constant along a tubular region that extends along at least a majority of a full length of the reinforcement member.

Example 223

The access system of any one of Example 178 to Example 222, wherein a distal tip of the cannula is positioned within the reinforcement member when the cannula is in the retracted position, such that the distal tip of the cannula is first positioned distal of and external to the reinforcement member only after the cannula has been moved from the retracted position.

Example 224

The access system of any one of Example 178 to Example 222, wherein a distal tip of the cannula is first positioned distal of and external to the reinforcement member when the cannula is in the retracted position.

Example 225

The access system of any one of Example 178 to Example 224, wherein the cannula comprises a first distal segment that is relatively softer than a second segment that is proximally adjacent to the first segment, and wherein the second segment comprises a distal terminus that is within the reinforcement member when the cannula is in the retracted position.

Example 226

The access system of any one of Example 178 to Example 225, wherein the distal terminus of the second segment of the cannula is within the reinforcement member when the cannula is in the advanced position.

Example 227

The access system of Example 225 or Example 226, wherein the distal terminus of the second segment of the cannula is within the reinforcement member throughout movement of the cannula from the retracted position to the advanced position.

Example 228

The access system of any one of Example 178 to Example 225, wherein the distal terminus of the second segment of the cannula is distal to a distal tip of the reinforcement member when the cannula is in the advanced position.

Example 229

The access system of any one of Example 178 to Example 227, further comprising a sheath coupled to the connector, wherein the cannula extends through at least a portion of the sheath, the cannula being movable relative to the sheath from the retracted position to the advanced position.

Example 230

The access system of Example 229, wherein at least a portion of the sheath and at least a portion of the connector are integrally formed of a unitary piece of material.

Example 231

The access system of Example 229 or Example 230, wherein, when the cannula is in each of the retracted and advanced positions, at least some portion of the cannula is positioned within the sheath.

Example 232

The access system of any one of Example 229 to Example 231, wherein at least some portion of the cannula is positioned within the sheath throughout movement of the cannula from the retracted position to the advanced position.

Example 233

The access system of any one of Example 229 to Example 232, wherein the sheath comprises a tube having a proximal end and a distal end, and wherein the cannula extends through at least the proximal end of the sheath when in the retracted position and extends through at least the distal end of the sheath when in the advanced position.

Example 234

The access system of any one of Example 229 to Example 233, further comprising a follower fixedly attached to the cannula and positioned within the sheath, wherein the follower moves in unison with the cannula as the cannula is moved from the retracted position to the advanced position.

Example 235

The access system of Example 234, wherein the follower cooperates with the sheath to delimit proximal movement of the cannula relative to the sheath.

Example 236

The access system of Example 234 or Example 235, wherein the follower and the sheath comprise a rotational alignment mechanism by which a rotational orientation of the cannula is maintained relative to the sheath.

Example 237

The access system of Example 236, wherein the rotational alignment mechanism comprises a protrusion positioned within a groove, wherein the sheath defines one of the protrusion and the groove and the follower defines the other of the protrusion and the groove.

Example 238

The access system of any one of Example 229 to Example 237, further comprising an actuator attached to the cannula, wherein at least a portion of the actuator is accessible external to the sheath so as to be manipulated to move the cannula between the advanced and retracted positions

Example 239

The access system of Example 238, wherein the sheath comprises a longitudinally extending track, and wherein a portion of the actuator extends through the track.

Example 240

The access system of any one of Example 229 to Example 239, wherein the cannula is devoid of an actuator.

Example 241

The access system of any one of Example 229 to Example 240, wherein the cannula is moved from the retracted position to the advanced position by directly contacting the cannula.

Example 242

The access system of any one of Example 178 to Example 241, wherein the connector comprises a snap-fit arrangement that is configured to snap onto a hub of the closed intravenous catheter system to securely couple the connector to the closed intravenous catheter system.

Example 243

The access system of Example 242, wherein the snap-fit arrangement comprises two or more flexible flaps that are configured to selectively attach to the hub of the closed intravenous catheter system.

Example 244

The access system of any one of Example 178 to Example 243, wherein:
the closed intravenous catheter system further comprises a septum spaced from the valve; and
a distal tip of the reinforcement member is configured to be positioned proximal to the septum when the connector is attached to the closed intravenous catheter system.

Example 245

The access system of any one of Example 178 to Example 243, wherein:
the closed intravenous catheter system comprises a septum spaced from the valve;
the reinforcement member comprises a projection that extends distally from a surface of the connector; and
at least a portion of the projection of the reinforcement member is configured to extend through the septum of the closed intravenous catheter system when the connector is attached to the closed intravenous catheter system.

Example 246

The access system of Example 245, wherein the septum comprises an opening that is in an unsealed state prior to insertion of the projection of the reinforcement member through the septum.

Example 247

The access system of Example 246, wherein the projection of the reinforcement member is configured to be inserted through the opening of the septum.

Example 248

The access system of any one of Example 245 to Example 247, wherein the projection extends distally past a distal end of the connector.

Example 249

The access system of any one of Example 245 to Example 247, wherein the projection is proximally recessed relative to a distal end of the connector.

Example 250

The access system of any one of Example 178 to Example 249, wherein, when the connector is coupled with the closed intravenous catheter system, the reinforcement member aims the cannula toward a sealable opening of the valve such that the distal tip of the cannula is advanced through the sealable opening of the valve as the cannula is moved from the retracted position to the advanced position.

Example 251

The access system of Example 250, wherein the sealable opening is substantially centered relative to the valve, and wherein, when the connector is coupled with the closed intravenous catheter system, the reinforcement member is substantially centered so as to be aligned with the sealable opening.

Example 252

The access system of any one of Example 178 to Example 251, wherein the closed intravenous catheter system further comprises a removable piercing member that extends through the valve and through the catheter tube to assist in positioning the catheter tube in the blood vessel of the patient, and wherein the piercing member is configured to be removed from the closed intravenous catheter system prior to coupling the connector of the access system with the closed intravenous catheter system.

Example 253

The access system of any one of Example 178 to Example 252, wherein the closed intravenous catheter system comprises an integrated side port through which fluid may be transferred to or from the catheter tube.

Example 254

The access system of Example 253, wherein the side port comprises an extension tube and a further connector attached to a proximal end of the extension tube.

Example 255

The access system of Example 254, wherein no portion of the cannula passes through the extension tube as the cannula moves between the retracted position and the advanced position.

Example 256

The access system of any one of Example 178 to Example 255, wherein the closed intravenous catheter system comprises a hub that defines a cavity, and wherein the valve is positioned within the cavity.

Example 257

The access system of Example 256, further comprising a septum positioned at a proximal end of the cavity and spaced from the valve.

Example 258

The access system of Example 257, wherein the septum defines a permanent opening and the valve defines a sealable opening that are aligned with a longitudinal axis that extends through the catheter tube.

Example 259

The access system of Example 258, wherein the closed intravenous catheter system further comprises a piercing member that extends through the openings of the septum and the valve and further extends through the catheter tube, and wherein the piercing member is configured to be removed from the catheter tube, the valve, and the septum prior to coupling of the connector with the closed intravenous line.

Example 260

The access system of Example 258 or Example 259, wherein a distal tip of the cannula is advanced substantially rectilinearly through the septum, the valve, and into the catheter tube as the cannula is transitioned from the retracted position toward the advanced position.

Example 261

The access system of any one of Example 257 to Example 260, wherein the reinforcement member extends through the septum when the connector is coupled with the closed intravenous catheter system.

Example 262

The access system of any one of Example 178 to Example 261, wherein the cannula comprises a first segment at a distal end thereof and a second segment that extends proximally from the first segment, wherein the second segment is stiffer than the first segment.

Example 263

The access system of Example 262, wherein at least a portion of the second segment extends through the valve when the cannula is in the advanced position.

Example 264

The access system of Example 262 or Example 263, wherein the second segment comprises a rigid tube that encompasses a flexible tube.

Example 265

The access system of Example 264, wherein the rigid tube is formed of a metallic material and wherein the flexible tube is formed of a polymeric material.

Example 266

The access system of any one of Example 178 to Example 265, further comprising the closed intravenous catheter system.

Example 267

A kit comprising:
  an access system according to any one of Example 178 to Example 266; and
  instructions for using the kit, the instructions comprising directions to:
    couple the connector to the closed intravenous catheter system while the catheter tube of the closed intravenous catheter system is positioned in the blood vessel of the patient; and
    advance the cannula from the retracted position to the advanced position.

Example 268

The kit of Example 267, wherein the instructions for using the kit further comprise directions to:
  couple a fluid transfer device to the cannula; and
  draw blood from the blood vessel through the cannula and into the fluid transfer device.

Example 269

A method of using the access system of any one of Example 178 to Example 266, the method comprising:
  coupling the connector to the closed intravenous catheter system while the catheter tube of the closed intravenous catheter system is positioned in the blood vessel of the patient; and
  advancing the cannula from the retracted position to the advanced position.

Example 270

An Access System Comprising:
  a connector configured to couple with an implement port of a catheter assembly that is configured to transition from an insertion configuration to an access configuration, the catheter assembly comprising:
    a hub comprising the implement port, an access port, and a cavity, the implement port being configured to permit a piercing implement to extend therethrough when the catheter assembly is in the insertion configuration;

a catheter tube coupled to the hub, the catheter tube defining a first lumen in fluid communication with the cavity, the first lumen being configured to receive at least a portion of the piercing implement therein when the catheter assembly is in the insertion configuration, the catheter tube being configured for insertion in a blood vessel of a patient;

an extension tube coupled to the access port of the hub, the extension tube defining a second lumen in fluid communication with the cavity; and a valve coupled to the hub, the valve being configured to be in an open state when the piercing implement extends therethrough while the catheter assembly is in the insertion configuration, the valve further being configured to transition to a closed state to prevent fluid communication between the cavity and the implement port upon removal of the piercing implement from the sealing member;

a cannula coupled to the connector and configured to be moved relative to the connector from a retracted position to an advanced position, the cannula being sized to extend through at least a portion of the catheter tube when in the advanced position to provide access to blood within the blood vessel when the catheter tube is within the blood vessel; and a reinforcement member sized to permit a portion of the cannula to be advanced therethrough as the cannula is advanced from the retracted position to the advanced position, wherein the reinforcement member satisfies one or more of the following conditions when the connector is coupled with the implement port of the catheter assembly:

a distal tip of the reinforcement member is positioned at a proximal face of the valve without being embedded in the valve;

the distal tip of the reinforcement member is spaced proximally from the proximal face of the valve;

no portion of the reinforcement member is in contact with the valve; or no portion of the reinforcement member extends through the valve.

Example 271

The access system of Example 270, wherein the cannula comprises a polymeric tube and a rigid support member that encompasses a portion of the polymeric tube, and wherein the support member is sized such that at least a portion of the support member passes through the reinforcement member as the cannula is moved to the advanced position.

Example 272

The access system of Example 270 or Example 271, further comprising the catheter assembly.

Example 273

The access system of any one of Example 270 to Example 272, wherein the catheter assembly further comprises the piercing implement.

Example 274

The access system of any one of Example 270 to Example 273, wherein the piercing implement comprises a needle.

Example 275

An Access System Comprising:

a connector configured to couple with a catheter assembly that comprises a catheter tube configured to be positioned in a blood vessel of a patient;

a cannula movable relative to the connector from a retracted position to an intermediate position and from the intermediate position to an advanced position, the cannula comprising a distal tip; and a reinforcement tube that encompasses at least the distal tip of the cannula and is releasably connected to the cannula so as to move in tandem with the cannula throughout movement of the cannula from the retracted position to the intermediate position, the reinforcement tube and the cannula being configured to disconnect from each other at the intermediate position to permit the cannula to advance distally through the reinforcement tube as the cannula is transitioned from the intermediate position to the advanced position.

Example 276

The access system of Example 275, wherein, when the connector and the catheter assembly are in a coupled state, at least the distal tip of the cannula is configured to be advanced through at least a portion of the catheter tube as the cannula is moved to the advanced position.

Example 277

The access system of Example 275 or Example 276, wherein the reinforcement tube becomes substantially stationary relative to the connector when the cannula passes through the intermediate position.

Example 278

The access system of Example 277, wherein the reinforcement tube remains substantially stationary relative to the connector as the cannula transitions from the intermediate position to the advanced position.

Example 279

The access system of any one of Example 275 to Example 278, further comprising an arm attached to the cannula and a catch attached to the reinforcing tube, wherein the arm engages the catch throughout movement of the cannula from the retracted position to the intermediate position and disengages from the catch as the cannula is moved distally past the intermediate position.

Example 280

The access system of Example 279, further comprising a sheath that comprises a first chamber defining a first diameter and a second chamber positioned distal of the first chamber and defining a second diameter larger than the first diameter, wherein the first chamber of the sheath is sized to constrain at least a distal end of the arm from flexing outwardly while positioned in the first chamber such that the arm engages the catch while in the first chamber, and wherein the second chamber of the sheath is sized to permit the distal end of the arm to flex outwardly to disengage from the catch and to move distally past the catch.

Example 281

The access system of Example 280, wherein a proximal end of the second chamber is proximal of the intermediate position.

Example 282

The access system of Example 280 or Example 281, wherein the arm is outwardly biased such that the distal end of the arm automatically flexes outwardly and disengages from the catch when advanced through the second chamber of the sheath.

Example 283

The access system of Example 280 or Example 281, wherein the arm and the catch comprise a ramped interface that causes the distal end of the arm to flex outwardly and disengage from the catch when positioned in the second chamber of the sheath and when the reinforcing tube encounters increased resistance to distal movement as the cannula is advanced toward the advanced position.

Example 284

An Access System Comprising:
  a connector configured to couple with a catheter assembly that includes a catheter tube preplaced into a blood vessel of a patient; and
  a cannula movable relative to the connector from a retracted state to a deployed state, the cannula comprising at least a distal portion that is configured to be advanced through at least a portion of the catheter tube as the cannula is transitioned from the retracted state to the advanced state, the cannula comprising:
    a first segment at a distal end of the cannula;
    a second segment attached to the first segment at an interface, the first segment being relatively softer than the second segment; and
    a tie layer extending over the interface and at least a portion of each of the first and second segments to attach the first and second segments together or to reinforce an attachment between the first and second segments.

Example 285

The access system of Example 284, wherein the second segment comprises a metal tube.

Example 286

The access system of Example 284 or Example 285, wherein a distal tip of the tie layer is proximally spaced from the distal tip of the cannula, and wherein the distal tip of the tie layer is configured to contact an internal surface of the catheter tube to delimit proximal movement of the cannula relative to the catheter tube.

Example 287

The access system of any one of Example 284 or Example 286, wherein a distal tip of the tie layer is proximally spaced from the distal tip of the cannula, and wherein the distal tip of the tie layer is configured to contact an internal surface of the catheter tube to provide tactile feedback to a user regarding a position of the cannula relative to the catheter tube.

Example 288

The access system of any one of Example 284 or Example 288, further comprising the catheter assembly.

Example 289

A method comprising:
  coupling an access system that comprises a reinforcement member and a movable cannula with a preplaced closed catheter system that comprises a valve and a catheter tube that is positioned within a blood vessel of a patient, said coupling comprising securing the access system to the preplaced closed catheter system such that at least one of the following conditions is satisfied:
    a distal tip of the reinforcement member is fixed at a position that is at a proximal end of the valve;
    the distal tip of the reinforcement member is fixed at a position that is proximally recessed from a proximal end of the valve;
    no portion of the reinforcement member is in contact with the valve; or
    no portion of the reinforcement member extends through the valve; and
  advancing the cannula of the access system from a position inside the reinforcement member through the valve of the closed catheter system and through at least a portion of the catheter tube.

Example 290

The method of Example 289, wherein the closed catheter system comprises a valve assembly that includes the valve and further includes a septum positioned proximal to the valve.

Example 291

The method of Example 290, wherein said coupling comprises advancing the distal tip of the reinforcement member of the access system through the septum before the distal tip is fixed at the position that is at or proximally recessed from a proximal end of the valve.

Example 292

The method of any one of Example 289 to Example 291, wherein the reinforcement member comprises a tube.

Example 293

The method of any one of Example 289 to Example 292, wherein said coupling is achieved without making any contact between the reinforcement member and the valve.

Example 294

The method of any one of Example 289 to Example 293, wherein said coupling is achieved without advancing any portion of the reinforcement member into or through the valve.

Example 295

The method of any one of Example 289 to Example 294, wherein the valve of the closed catheter system comprises a closable opening that is configured to permit a piercing element to extend therethrough during insertion of the catheter tube into the blood vessel of the patient, wherein the sealable region is in a self-sealed state with the piercing element having been removed therefrom during said coupling, and wherein said advancing the cannula comprises advancing the cannula through the closable opening of the valve.

Example 296

The method of any one of Example 289 to Example 295, wherein said advancing the cannula is achieved without advancing the distal tip of the reinforcement member distally past the proximal end of the valve.

Example 297

The method of any one of Example 289 to Example 296, wherein said advancing the cannula is achieved without contacting the reinforcement member to the valve.

Example 298

The method of any one of Example 289 to Example 297, wherein said advancing the cannula is achieved without extending the reinforcement member through any portion of the valve.

Example 299

The method of any one of Example 289 to Example 298, wherein the closed catheter system further comprises a hub coupled with the catheter tube at a first port of the hub, wherein an extension tube is coupled with a second port of the hub, and wherein a third port of the hub comprises the valve.

Example 300

The method of Example 299, wherein said coupling the access system with the preplaced closed catheter system comprises coupling a connector of the access system with the third port of the hub.

Example 301

The method of Example 299 or Example 300, wherein said advancing the cannula comprises advancing a distal portion of the cannula through the third port of the hub then through the first port of the hub and into the catheter tube.

Example 302

The method of any one of Example 299 to Example 301, wherein the hub of the preplaced closed catheter system is secured directly to the skin of the patient.

Example 303

The method of Example 302, wherein said coupling and said advancing are achieved without moving the hub of the preplaced catheter system relative to the skin of the patient.

Example 304

The method of Example 302 or Example 303, wherein the hub of the preplaced closed catheter system is positioned flat against the skin of the patient without any other element (e.g., wedge-shaped or otherwise) being present between the hub and the skin of the patient.

Example 305

The method of any one of Example 302 to Example 304, wherein a portion of the catheter tube is positioned within an insertion site that extends through the skin of the patient, and wherein said coupling and said advancing are achieved without contacting an external surface of one or more of the hub or the catheter tube to adjust a position of the portion of the catheter tube that extends through the insertion site.

Example 306

The method of any one of Example 289 to Example 305, wherein the access system further comprises an additional connector at a proximal end of the cannula, and wherein the method further comprises:
coupling a fluid collection device to the additional connector; and
after said advancing the cannula of the access system, drawing blood through the cannula into the fluid collection device.

Example 307

The method of Example 306, further comprising, after said drawing blood, retracting the cannula of the access system from the catheter tube.

Example 308

The method of Example 307, further comprising, after said retracting the cannula, decoupling the access system from the preplaced closed catheter system.

Example 309

The method of Example 307 or Example 308, further comprising, after said retracting the cannula, power injecting fluid into the patient via the preplaced closed catheter system.

Example 310

The method of any one of Example 289 to Example 309, wherein the catheter tube of the preplaced closed catheter system is inserted into a vein of the patient at any one of a dorsal arch of a hand, a forearm, or an antecubital fossa position.

Example 311

An Access System Comprising:
a connector configured to couple with a catheter assembly that includes a catheter tube preplaced into a blood vessel of a patient;
a reinforcement tube fixedly secured to the connector; and
a cannula movable relative to the connector from a retracted state to a deployed state, the cannula comprising:
a distal segment that comprises at least a portion of a flexible and/or polymeric tube; and
a medial segment that extends proximally from the distal segment, the medial segment comprising a metal tube sized to pass through the reinforcement tube, wherein, when the cannula is in the retracted state, a distal tip of the medial segment is positioned within the reinforcement tube.

Example 312

The access system of Example 311, wherein the reinforcement tube is metallic.

Example 313

The access system of Example 312, wherein the reinforcement tube comprises stainless steel.

Example 314

The access system of any one of Example 311 to Example 313, wherein at least a portion of the metal tube of the medial segment is positioned within the reinforcement tube throughout movement of the cannula from the retracted state to the deployed state.

Example 315

The access system of any one of Example 311 to Example 314, wherein a portion of the metal tube of the medial segment extends distally beyond a distal tip of the reinforcement tube when the cannula is in the deployed state.

Example 316

The access system of any one of Example 311 to Example 315, wherein the flexible and/or polymeric tube of the distal segment comprises at least one of polyimide, polyamide, PEEK, and polyurethane.

Example 317

The access system of any one of Example 311 to Example 316, wherein the distal segment is configured to extend through the catheter tube such that at least a distal end of the distal segment extends distally beyond a distal tip of the catheter tube when the cannula is in the deployed state.

Example 318

The access system of any one of Example 311 to Example 317, wherein the metal tube of the medial segment and the flexible and/or polymeric tube of the distal segment are joined together via heat shrink tubing.

Example 319

The access system of any one of Example 311 to Example 317, wherein the flexible and/or polymeric tube is longer than the first segment of the cannula, wherein the distal segment comprises a first portion of the flexible and/or polymeric tube, and wherein the medial segment comprises a second portion of the flexible and/or polymeric tube that extends continuously and proximally from the first portion of the flexible and/or polymeric tube.

Example 320

The access system of Example 319, wherein the metal tube of the medial segment encompasses the second portion of the flexible and/or polymeric tube.

Example 321

The access system of Example 320, wherein the metal tube of the medial segment comprises an inner tubular surface that approximates an outer tubular surface of the second portion of the flexible and/or polymeric tube to thereby support the second portion of the flexible and/or polymeric tube.

Example 322

The access system of Example 320 or Example 321, wherein the metal tube of the medial segment prevents one or more of bending, buckling, or kinking of the second portion of the flexible and/or polymeric tube when the flexible and/or polymeric tube encounters proximally directed resistive forces as the cannula is advanced from the retracted state to the deployed state.

Any suitable combination of the various features of the various embodiments and examples disclosed herein is contemplated. The term "coupled to" can mean connected to in any suitable fashion, whether that coupling is direct or indirect. Separate components may be coupled to each other. Moreover, in some instances, where separately identified components are integrally formed from a unitary piece of material, or stated otherwise, are included together in a monolithic element, those elements may also be said to be coupled to one another.

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any one of claims [x] through the immediately preceding claim," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C.

§ 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. An access system comprising:
a connector configured to couple with a catheter assembly that comprises a catheter tube configured to be positioned in a blood vessel of a patient;
a reinforcement member fixedly secured to the connector; and
a cannula movable relative to the reinforcement member from a retracted position in which at least a portion of the cannula is within the reinforcement member to an advanced position, the cannula comprising:
a polymeric tube that defines a distal tip; and
a support tube that encompasses a portion of and is stiffer than the polymeric tube, the support tube defining an inner diameter that is marginally larger than an outer diameter of the polymeric tube so as to prevent kinking of the polymeric tube, the support tube being in a fixed relationship with the polymeric tube so as to move in unison therewith, the support tube defining a distal edge that is proximally spaced from the distal tip of the polymeric tube and that is configured to be within the reinforcement member when the distal tip of the polymeric tube is first positioned distal of and external to the reinforcement member as the cannula is transitioned from the retracted position to the advanced position,
wherein, when the connector and the catheter assembly are in a coupled state, at least a portion of the polymeric tube that extends distally beyond the distal edge of the support tube is configured to be advanced through at least a portion of the catheter tube as the cannula is transitioned from the retracted position to the advanced position.

2. The access system of claim 1, wherein the inner diameter of the support tube is larger than the outer diameter of the polymeric tube by no greater than 30 percent.

3. The access system of claim 1, wherein, at each stage throughout movement of the cannula from the retracted position to the advanced position, at least some portion of the support tube is positioned within the reinforcement member.

4. The access system of claim 1, wherein, wherein the distal edge of the support tube is configured to extend distally past a distal tip of the reinforcement member when the cannula is in the advanced position.

5. The access system of claim 1, wherein the distal edge of the support tube is within the reinforcement member when the cannula is in the retracted position.

6. The access system of claim 1, wherein the distal edge of the support tube is distal to a distal tip of the reinforcement member when the cannula is in the advanced position.

7. The access system of claim 1, further comprising a sheath coupled to the connector, wherein the cannula extends through at least a portion of the sheath, the cannula being movable relative to the sheath from the retracted position to the advanced position.

8. The access system of claim 1, further comprising the catheter assembly.

9. The access system of claim 8, wherein the catheter assembly comprises a valve.

10. The access system of claim 9, wherein, when the connector is coupled with the catheter assembly, no portion of the reinforcement member extends through the valve.

11. The access system of claim 9, wherein, when the connector is coupled with the catheter assembly, a distal tip of the reinforcement member is at or proximally spaced from a proximal surface of the valve.

12. The access system of claim 9, wherein, when the connector is coupled with the catheter assembly, the reinforcement member aims the cannula toward a sealable opening of the valve such that the distal tip of the polymeric tube is advanced through the sealable opening of the valve as the cannula is moved from the retracted position to the advanced position.

13. The access system of claim 12, wherein the sealable opening is substantially centered relative to the valve, and wherein, when the connector is coupled with the catheter assembly, the reinforcement member is substantially centered so as to be aligned with the sealable opening.

14. The access system of claim 1, wherein the catheter assembly further comprises a removable piercing member that extends through the valve and through the catheter tube to assist in positioning the catheter tube in the blood vessel of the patient, and wherein the piercing member is configured to be removed from the catheter assembly prior to coupling the connector of the access system with the catheter assembly.

15. The access system of claim 1, wherein the catheter assembly is one of a closed intravenous catheter system and an open intravenous catheter system.

16. The access system of claim 1, further comprising a sealing member coupled to each of the reinforcement member and the support tube so as to form a fluid-tight seal to prevent egress of fluid from a space between the support tube and the reinforcement member.

17. The access system of claim 16, wherein the sealing member is fixedly secured to the reinforcement member and the support tube is movable relative to the sealing member.

18. A kit comprising:
the access system of claim 1; and
instructions for using the kit, the instructions comprising directions to:
couple the connector to the catheter assembly while the catheter tube of the catheter assembly is positioned in the blood vessel of the patient; and
advance the cannula from the retracted position to the advanced position.

19. The kit of claim 18, wherein the instructions for using the kit further comprise directions to:
couple a fluid transfer device to the cannula; and
draw blood from the blood vessel through the cannula and into the fluid transfer device.

20. A method of using the access system of claim 1, the method comprising:
coupling the connector to the catheter assembly when the catheter tube of the catheter assembly is positioned in the blood vessel of the patient; and
advancing the cannula from the retracted position to the advanced position.

* * * * *